(12) United States Patent
Hlavinka

(10) Patent No.: US 9,056,930 B2
(45) Date of Patent: *Jun. 16, 2015

(54) CATALYST COMPOSITIONS CONTAINING TRANSITION METAL COMPLEXES WITH THIOLATE LIGANDS

(71) Applicant: Chevron Phillips Chemical Company LP, The Woodlands, TX (US)

(72) Inventor: Mark L. Hlavinka, Bartlesville, OK (US)

(73) Assignee: Chevron Phillips Chemical Company LP, The Woodlands, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 14/093,809

(22) Filed: Dec. 2, 2013

(65) Prior Publication Data

US 2014/0094577 A1  Apr. 3, 2014

Related U.S. Application Data

(63) Continuation of application No. 13/042,807, filed on Mar. 8, 2011, now Pat. No. 8,618,229.

(51) Int. Cl.

| C08F 4/64 | (2006.01) |
|---|---|
| C08F 4/76 | (2006.01) |
| B01J 31/00 | (2006.01) |
| C08F 110/02 | (2006.01) |
| C07F 9/00 | (2006.01) |
| C07F 15/02 | (2006.01) |
| C07F 5/00 | (2006.01) |
| C07F 7/00 | (2006.01) |
| C07F 7/08 | (2006.01) |
| C07F 13/00 | (2006.01) |
| C08F 4/60 | (2006.01) |

(52) U.S. Cl.
CPC ........... *C08F 110/02* (2013.01); *C08F 4/60141* (2013.01); *C07F 9/00* (2013.01); *C07F 15/02* (2013.01); *C07F 15/025* (2013.01); *C07F 5/003* (2013.01); *C07F 7/006* (2013.01); *C07F 7/0818* (2013.01); *C07F 9/005* (2013.01); *C07F 13/005* (2013.01)

(58) Field of Classification Search
CPC .................................................. C08F 4/60141
USPC .............. 526/161, 172, 160, 170, 169, 169.1, 526/164, 148, 151, 153, 134; 556/51, 57, 556/42; 502/103

See application file for complete search history.

(56) References Cited

U.S. PATENT DOCUMENTS

| 3,242,099 A | 3/1966 | Manyik et al. |
|---|---|---|
| 3,248,179 A | 4/1966 | Norwood |
| 4,060,480 A | 11/1977 | Reed et al. |
| 4,452,910 A | 6/1984 | Hopkins et al. |
| 4,501,885 A | 2/1985 | Sherk et al. |
| 4,588,790 A | 5/1986 | Jenkins, III |
| 4,794,096 A | 12/1988 | Ewen |
| 4,808,561 A | 2/1989 | Welborn |
| 5,352,749 A | 10/1994 | DeChellis |
| 5,376,611 A | 12/1994 | Shveima |
| 5,436,304 A | 7/1995 | Griffin et al. |
| 5,455,314 A | 10/1995 | Burns et al. |
| 5,565,175 A | 10/1996 | Hottovy et al. |
| 5,575,979 A | 11/1996 | Hanson |
| 5,576,259 A | 11/1996 | Hasegawa et al. |
| 5,739,220 A | 4/1998 | Shamshoum et al. |
| 5,807,938 A | 9/1998 | Kaneko et al. |
| 5,919,983 A | 7/1999 | Rosen et al. |
| 6,107,230 A | 8/2000 | McDaniel et al. |
| 6,165,929 A | 12/2000 | McDaniel et al. |
| 6,239,235 B1 | 5/2001 | Hottovy et al. |
| 6,262,191 B1 | 7/2001 | Hottovy et al. |
| 6,294,494 B1 | 9/2001 | McDaniel et al. |
| 6,300,271 B1 | 10/2001 | McDaniel et al. |
| 6,316,553 B1 | 11/2001 | McDaniel et al. |
| 6,355,594 B1 | 3/2002 | McDaniel et al. |
| 6,376,415 B1 | 4/2002 | McDaniel et al. |
| 6,388,017 B1 | 5/2002 | McDaniel et al. |
| 6,391,816 B1 | 5/2002 | McDaniel et al. |
| 6,395,666 B1 | 5/2002 | McDaniel et al. |
| 6,524,987 B1 | 2/2003 | Collins et al. |
| 6,548,441 B1 | 4/2003 | McDaniel et al. |
| 6,548,442 B1 | 4/2003 | McDaniel et al. |
| 6,576,583 B1 | 6/2003 | McDaniel et al. |
| 6,613,712 B1 | 9/2003 | McDaniel et al. |
| 6,632,894 B1 | 10/2003 | McDaniel et al. |
| 6,667,274 B1 | 12/2003 | Hawley et al. |
| 6,750,302 B1 | 6/2004 | McDaniel et al. |
| 6,833,415 B2 | 12/2004 | Kendrick et al. |
| 7,247,594 B2 | 7/2007 | Jayaratne et al. |
| 7,884,163 B2 | 2/2011 | McDaniel et al. |

(Continued)

FOREIGN PATENT DOCUMENTS

EP  0 606 125 A2  7/1994

OTHER PUBLICATIONS

Gómez-Benitez et al., Inorg. Chim. Acta, 2007, 360, 2128-2138.*
Pérez-Lourido et al., Inorg. Chim. Acta, 2003, 356, 193-202.*
Hahn et al. Inorg. Chem. 1995, 34, 6562-6564.*
Hawley's Condensed Chemical Dictionary, 11th Ed., John Wiley & Sons, 1995, 3 pages.
Cotton et al., Advanced Inorganic Chemistry, 6th Ed., Wiley-Interscience, 1999, 4 pages.
Pinnavaia, "Intercalated Clay Catalysts," Science, 1983, 220(4595), pp. 365-371.
Thomas, "Sheet Silicate Intercalates: New Agents for Unusual Chemical Conversions," Intercalation Chemistry (S. Whittington and A. Jacobson, eds.), Academic Press, Inc. Ch. 3, 1972, pp. 55-99.

(Continued)

*Primary Examiner* — Rip A Lee

(74) *Attorney, Agent, or Firm* — Merchant & Gould

(57) ABSTRACT

The present invention discloses catalyst compositions employing transition metal complexes with a thiolate ligand. Methods for making these transition metal complexes and for using such compounds in catalyst compositions for the polymerization of olefins also are provided.

23 Claims, 17 Drawing Sheets

(56) References Cited

U.S. PATENT DOCUMENTS

| | | |
|---|---|---|
| 8,618,229 B2 | 12/2013 | Hlavinka |
| 2004/0059070 A1 | 3/2004 | Whitte et al. |
| 2009/0240010 A1 | 9/2009 | McDaniel et al. |
| 2010/0076167 A1 | 3/2010 | McDaniel et al. |
| 2011/0092357 A1 | 4/2011 | McDaniel et al. |
| 2012/0232235 A1 | 9/2012 | Hlavinka |

OTHER PUBLICATIONS

Block et al., "o-Lithiothiophenol equivalents. Generation, reactions and applications in synthesis of hindered thiolate ligands," J. Am. Chem. Soc., 1989, 111(2), pp. 658-665.

Carmalt et al., "Reactivity of tetrakisdimethylamido-titanium(IV) and -zirconium(IV) with thiols," New J. Chem., 2005, 29, pp. 620-624.

Chen et al., "Bis(imidodithiodiphosphinato) Titanium and Zirconium Complexes: Synthesis, Characterization, and Their Catalytic Activity in the Polymerization of α-Olefins," Organometallics, 2009, 28, pp. 2391-2400.

Cornman et al., "Oxidation of a Vanadium (V)-Dithiolate Complex to a Vanadium (V)-$\eta^2$,$\eta^2$-Disulfenate Complex," J. Am. Chem. Soc., 1997, 119, pp. 5986-5987.

Coucouvanis et al., "Zirconium—Sulfur Chemistry. Synthesis and Structural Characterization of the $Zr_3S_3(^tBuS)_2(BH_4)_4(THF)_2$, $Zr_3(S)(^tBuS)_{10}$, and $(mg(THF)_6)[Zr_2(SPh)_{7.2}(CH2Ph)_{1.8}]_2$•3THF Clusters. Activation and Cleavage of the C—S Bond in Zirconium-Coordinated Alkanethiolate Ligands," Inorg. Chem., 1994, 33, pp. 3645-3655.

Femec et al, "Influence of π-Donation on N-Methyl Group Exchange in Zirconocene N,N-Dimethyldithiocarbamates and N,N-Dimethylthiocarbamates," Inorg. Chem., 1989, 28, pp. 2789-2796.

Figuly et al., "Directed ortho-lithiation of lithium thiophenolate. New methodology for the preparation of ortho-substituted thiophenols and related compounds," J. Am. Chem. Soc., 1989, 111(2), pp. 654-658.

Gibson et al., "Advances in Non-Metallocene Olefin Polymerization Catalysis," Chem. Rev. 2003, 103, pp. 283-315.

Hanh et al., "Synthesis and Molecular Structure of a Pentacoordinated Nickel(II) Complex with a Mixed $S_2N_3$ Coordination Sphere," Inorg. Chem. 1995, 34, pp. 6562-6564.

Janas et al., "Synthesis and molecular structure of vanadium(III) dithiolate complexes: a new class of alkene polymerization catalysts," Chem. Commun., 1999, pp. 1015-1016.

Jia et al., "Syntheses, Reactions, and Ethylene Polymerization of Titanium Complexes with [N, O, S] Ligands," Organometallics, 2009, 229, 28, pp. 1872-1877.

Nanda et al., "The First Oxovanadium(V)-Thiolate Complex, [VO(SCH$_2$CH$_2$)$_3$N]," Inorganic Chemistry, 1996, 35(1), 2 pages.

Alvarado-Rodriguez et al., "Study of the DSb (D = O, S) transannular interaction in Sb-monohalogenated dibenzostibocines—an experimental and theoretical study," European Journal of Inorganic Chemistry, 2003, Issue 19, pp. 3554-3562.

Sellman et al., "Highly soluble sulfur-rich [Ni(L) (siS3)] complexes containing the new ligand bis(2-mercapto-3-trimethylsilylphenyl) sulfide (2-) (siS32-)," European Journal of Inorganic Chemistry, 2002, 8, pp. 2138-2146.

Sellman et al., "Transition Metal Complexes with Sulfur Ligands, 138 Synthesis, Structures, and Reactions of Sulfur-Rich Nickel and Platinum Complexes with [MS3] and [MNS2] Cores," European Journal of Inorganic Chemistry, 1999, Issue 10, pp. 1715-1725.

Stephan et al., "Early transition metal thiolates," Coordination Chemistry Reviews, 1996, 147, pp. 147-208.

Takashima et al., "Syntheses of group 4 transition metal complexes bearing 2-pyridinethiolate ligands and their catalytic activities for ethylene polymerization," Polymer, 2006, 47, pp. 5762-5774.

Li, et al., Coordination Copolymerization of Severely Encumbered Isoalkenes with Ethylene: Enhanced Enchainment Mediated by Binuclear Catalysts and Cocatalysts, JACS Articles, 2005, 127, 14756-14768.

Modern Plastics Encyclopedia '96, Mid-Nov. 1995 Issue, vol. 72, No. 12, 3 pages.

Film Extrusion Manual—Process, Materials, Properties, TAPPI Press, 1992, pp. ix-xxiii.

International Search Report PCT/US2012/028219, dated Jun. 26, 2012, 6 pages.

Masahiro Yuki, et al., "Preparation of Thiolate-Bridged Dinuclear Ruthenium Complexes Bearing a Phosphine Ligand and Application to Propargylic Reduction of Propargylic Alcohols with 2-Propanol," Organometallics, vol. 29, No. 22, Nov. 22, 2010, pp. 5994-6001.

Rainer Hahn, et al.; "Synthesis and Molecular Structure of a Pentacoordinated Nickel(II)Complex with a Mixed S2N3 Coordination Sphere," Inorganic Chemistry, vol. 34, No. 26, Dec. 1, 1995, pp. 6562-6564.

Joachim Ballman, et al., "Secondary Bonding Interactions in Biomimetic [2Fe-2s] Clusters," Inorganic Chemistry, vol. 47, No. 5, Mar. 1, 2008, pp. 1586-1596.

Gómez-Benitez, et al., "Synthesis, Characterization and Catalytic Evaluation in the Heck Coupling Reactions of S—P—S Pincer Complexes of the Type [Pd{PhP(C6H4-s-S)2}(Par3) ]," Inorganic Chimica Acta, Elsevier BV, NL, vol. 360, No. 6, Mar. 27, 2007, pp. 2128-2138.

Cerrada, E., et al., "PPh(2-C6H4S)s as a Pincer Ligand in Nickel(II) and Palladium(II) Complexes X-ray Structure of [Ni{PPh(C6H4S)2}(PPh2Me)], [Pd2(-dppe){PPh(C6H4S)2}2] and [Ni{PPh(C6H4S)2}] 2," European Journal of Inorganic Chemistry, No. 4, 2002, pp. 826-833.

Paulo Pérez-Lourido, et al., "Synthesis and Characterization of Iron and Cobalt Complexes With Phosphinothiolate Ligands," Inorganica Chimica Acta, vol. 356, Dec. 1, 2003, pp. 193-202.

David Morales-Morales, et al., "Synthesis of Neutral Iridium(III) and Rhodium(III) Complexes with the Proligands Pri2P(C6H4-SH-2)[priPSH] ; PhP(C6H4-SH-2)2 [PhPS2H2] and PhP(C2H4SH)2 [ePS2H2]. The X-ray Crystal Structures of [Ir(priPS)3] and [Rh(H)(phPS2) (CO) (PPh3)]," Inorganic Chimica Acta, vol. 332, No. 1, Apr. 1, 2002, pp. 101-107.

Jonathan R. Dilworth, et al., "Complexes of Potentially Tri- and Tetra-Dentate Phosphinothiol Ligands With Mo, W, Re, Fe, Ru, Os, Rh, Ir, Ni," Journal of Chemical Society, Dalton Transactions, Chemical Society, No. 6, Jan. 1, 1996, pp. 1093-1104.

\* cited by examiner

CATALYST COMPOSITIONS CONTAINING TRANSITION METAL COMPLEXES WITH THIOLATE LIGANDS

REFERENCE TO RELATED APPLICATION

This application is a continuation application of U.S. patent application Ser. No. 13/042,807, filed on Mar. 8, 2011, now U.S. Pat. No. 8,618,229, the disclosure of which is incorporated herein by reference in its entirety.

BACKGROUND OF THE INVENTION

Polyolefins such as high density polyethylene (HDPE) homopolymer and linear low density polyethylene (LLDPE) copolymer can be produced using various combinations of catalyst systems and polymerization processes. Examples of commercially viable catalyst systems include chromium-based, metallocene-based, and Ziegler-Natta based catalyst systems.

The present invention relates generally to the field of olefin polymerization catalysis, catalyst compositions, methods for the polymerization of olefins, and polyolefins. More specifically, this invention relates to transition metal compounds having a thiolate ligand, and catalyst compositions employing such compounds.

SUMMARY OF THE INVENTION

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

The present invention generally relates to new catalyst compositions, methods for preparing catalyst compositions, methods for using the catalyst compositions to polymerize olefins, the polymer resins produced using such catalyst compositions, and articles produced using these polymer resins. In particular, the present invention relates to transition metal compounds with a thiolate ligand, and catalyst compositions employing such transition metal compounds. Catalyst compositions of the present invention which contain these transition metal compounds can be used to produce, for example, ethylene-based homopolymers and copolymers.

In addition to polymerization processes, and depending upon the transition metal in the transition metal compound, these transition metal compounds can be used in other catalytic processes. For example, transition metal amido complexes can be used as catalysts in hydroamination reactions. More generally, transition metal complexes can be employed as catalysts in hydrogenation reactions, oxidation reactions, among others. Alternatively, complexes of the transition series can be used as precursors in the preparation of metal films that are currently used in a number of industrial applications.

In accordance with an aspect of the present invention, non-metallocene transition metal complexes containing a transition metal and thiolate donors are disclosed and described.

In accordance with another aspect of the present invention, ligands containing a central donor atom capped by two aryl thiolates are disclosed and described.

In accordance with another aspect of the present invention, transition metal complexes containing a transition metal (e.g., such as titanium, zirconium, hafnium, or vanadium) and a ligand structure containing two sulfur donor atoms in conjunction with a more commonly used donor, such as nitrogen and oxygen, are disclosed and described.

In accordance with another aspect of the present invention, disclosed and described herein are transition metal compounds having the formula:

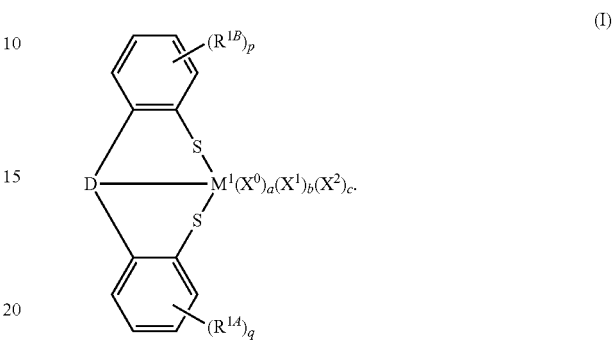

(I)

In formula (I), $M^1$ can be a transition metal; each $R^{1A}$ and $R^{1B}$ independently can a $C_1$ to $C_{18}$ hydrocarbyl or hydrocarbylsilyl group, wherein p and q independently can be 1, 2, 3, or 4; and D can be O, $NR^{1C}$, $PR^{1D}$, or a substituted or unsubstituted, saturated or unsaturated, $C_4$ to $C_{18}$ heterocyclic group, wherein $R^{1C}$ and $R^{1D}$ independently can be hydrogen or a $C_1$ to $C_{18}$ hydrocarbyl group. Additionally, each $X^0$ independently can be a neutral ligand, wherein a can be 0, 1, or 2; each $X^1$ independently can be a monoanionic ligand, wherein b can be 0, 1, 2, 3, or 4; and $X^2$ can be a dianionic ligand, wherein c can be 0 or 1. Generally, an oxidation state of $M^1$ is equal to (b+2c+2).

In accordance with another aspect of the present invention, disclosed and described herein are transition metal compounds having the formula:

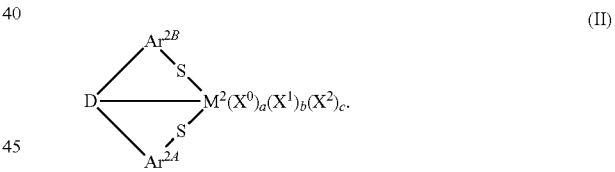

(II)

In formula (II), $M^2$ can be a Group 3 to Group 8 transition metal, including lathanides and actinides, $Ar^{2A}$ and $Ar^{2B}$ independently can be an arylene group, wherein any additional substituents on the arylene group independently can be a hydrogen atom or a $C_1$ to $C_{18}$ hydrocarbyl or hydrocarbylsilyl group; and D can be O, S, $NR^{1C}$, $PR^{1D}$, or a substituted or unsubstituted, saturated or unsaturated, $C_4$ to $C_{18}$ heterocyclic group, wherein $R^{1C}$ and $R^{1D}$ independently can be hydrogen or a $C_1$ to $C_{18}$ hydrocarbyl group. Additionally, each $X^0$ independently can be a neutral ligand, wherein a can be 0, 1, or 2; each $X^1$ independently can be a monoanionic ligand, wherein b can be 0, 1, 2, 3, or 4; and $X^2$ can be a dianionic ligand, wherein c can be 0 or 1. Generally, an oxidation state of $M^2$ is equal to (b+2c+2).

Catalyst compositions containing these transition metal complexes having thiolate ligands are also provided by the present invention. In one aspect, a catalyst composition is disclosed which comprises a transition metal complex and an activator. This catalyst composition can further comprise an organoaluminum compound. In some aspects, the activator can comprise an activator-support, while in other aspects, the activator can comprise an aluminoxane compound, an organoboron or organoborate compound, an ionizing ionic compound, or combinations thereof.

The present invention also contemplates and encompasses olefin polymerization processes. Such processes can comprise contacting a catalyst composition with an olefin monomer and optionally an olefin comonomer under polymerization conditions to produce an olefin polymer. Generally, the catalyst composition employed can comprise any of the transition metal compounds disclosed herein and any of the activators disclosed herein. Further, organoaluminum compounds also can be utilized in the catalyst compositions and/or polymerization processes.

Polymers produced from the polymerization of olefins, resulting in homopolymers, copolymers, terpolymers, etc., can be used to produce various articles of manufacture.

BRIEF DESCRIPTION OF THE FIGURES

FIG. 1 presents a $^1$H-NMR plot of ligand compound 3a.
FIG. 3 presents a $^1$H-NMR plot of zirconium complex 7a.

DEFINITIONS

Figure 1:
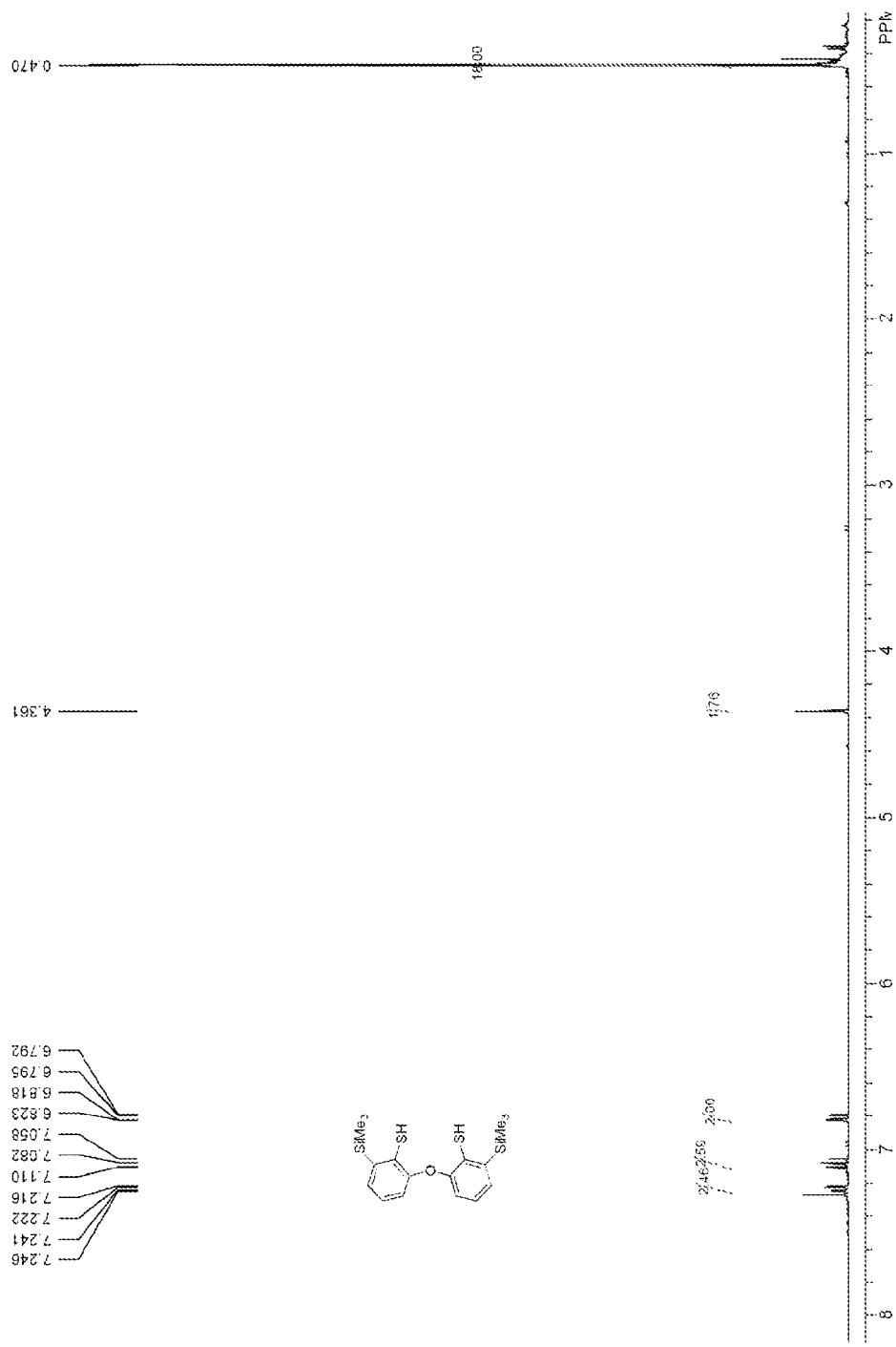

To define more clearly the terms used herein, the following definitions are provided. To the extent that any definition or usage provided by any document incorporated herein by reference conflicts with the definition or usage provided herein, the definition or usage provided herein controls.

The term "polymer" is used herein generically to include olefin homopolymers, copolymers, terpolymers, and so forth. A copolymer is derived from an olefin monomer and one olefin comonomer, while a terpolymer is derived from an olefin monomer and two olefin comonomers. Accordingly, "polymer" encompasses copolymers, terpolymers, etc., derived from any olefin monomer and comonomer(s) disclosed herein. Similarly, an ethylene polymer would include ethylene homopolymers, ethylene copolymers, ethylene terpolymers, and the like. As an example, an olefin copolymer, such as an ethylene copolymer, can be derived from ethylene and a comonomer, such as 1-butene, 1-hexene, or 1-octene. If the monomer and comonomer were ethylene and 1-hexene, respectively, the resulting polymer would be categorized an as ethylene/1-hexene copolymer.

In like manner, the scope of the term "polymerization" includes homopolymerization, copolymerization, terpolymerization, etc. Therefore, a copolymerization process would involve contacting one olefin monomer (e.g., ethylene) and one olefin comonomer (e.g., 1-hexene) to produce a copolymer.

The term "co-catalyst" is used generally herein to refer to organoaluminum compounds that can constitute one component of a catalyst composition. Additionally, "co-catalyst" can refer to other components of a catalyst composition including, but not limited to, aluminoxanes, organoboron or organoborate compounds, and ionizing ionic compounds, as disclosed herein, when used in addition to an activator-support. The term "co-catalyst" is used regardless of the actual function of the compound or any chemical mechanism by which the compound may operate. In one aspect of this invention, the term "co-catalyst" can be used to distinguish that component of the catalyst composition from the transition metal compound(s).

The terms "chemically-treated solid oxide," "activator-support," "treated solid oxide compound," and the like, are used herein to indicate a solid, inorganic oxide of relatively high porosity, which can exhibit Lewis acidic or Brønsted acidic behavior, and which has been treated with an electron-withdrawing component, typically an anion, and which is calcined. The electron-withdrawing component is typically an electron-withdrawing anion source compound. Thus, the chemically-treated solid oxide can comprise a calcined contact product of at least one solid oxide with at least one electron-withdrawing anion source compound. Typically, the chemically-treated solid oxide comprises at least one acidic solid oxide compound. The terms "support" and "activator-support" are not used to imply these components are inert, and such components should not be construed as an inert component of the catalyst composition. The activator-support of the present invention can be a chemically-treated solid oxide. The term "activator," as used herein, refers generally to a substance that is capable of converting a transition metal component into a catalyst that can polymerize olefins, or converting a contact product of a transition metal compound and a component that provides an activatable ligand (e.g., an alkyl, a hydride) to the transition metal compound, when the transition metal compound does not already comprise such a ligand, into a catalyst that can polymerize olefins. This term is used regardless of the actual activating mechanism. Illustrative activators include activator-supports, aluminoxanes, organoboron or organoborate compounds, ionizing ionic compounds, and the like. Aluminoxanes, organoboron or organoborate compounds, and ionizing ionic compounds generally are referred to as activators if used in a catalyst composition in which an activator-support is not present. If the catalyst composition contains an activator-support, then the aluminoxane, organoboron or organoborate, and ionizing ionic materials are typically referred to as co-catalysts.

The term "fluoroorgano boron compound" is used herein with its ordinary meaning to refer to neutral compounds of the form $BY_3$. The term "fluoroorgano borate compound" also has its usual meaning to refer to the monoanionic salts of a fluoroorgano boron compound of the form $[\text{cation}]^+[BY_4]^-$, where Y represents a fluorinated organic group. Materials of these types are generally and collectively referred to as "organoboron or organoborate compounds."

The terms "catalyst composition," "catalyst mixture," "catalyst system," and the like, do not depend upon the actual product or composition resulting from the contact or reaction of the initial components of the claimed catalyst composition/mixture/system, the nature of the active catalytic site, or the fate of the co-catalyst, the transition metal compound(s), any olefin monomer used to prepare a precontacted mixture, or the activator (e.g., activator-support), after combining these components. Therefore, the terms "catalyst composition," "catalyst mixture," "catalyst system," and the like, encompass the initial starting components of the composition, as well as whatever product(s) may result from contacting these initial starting components, and this is inclusive of both heterogeneous and homogenous catalyst systems or compositions.

The term "contact product" is used herein to describe compositions wherein the components are contacted together in any order, in any manner, and for any length of time. For example, the components can be contacted by blending or mixing. Further, contacting of any component can occur in the presence or absence of any other component of the compositions described herein. Combining additional materials or components can be done by any suitable method. Further, the term "contact product" includes mixtures, blends, solutions, slurries, reaction products, and the like, or combinations thereof. Although "contact product" can include reaction products, it is not required for the respective components to react with one another. Similarly, the term "contacting" is used herein to refer to materials which may be blended, mixed, slurried, dissolved, reacted, treated, or otherwise contacted in some other manner.

The term "precontacted" mixture is used herein to describe a first mixture of catalyst components that are contacted for a first period of time prior to the first mixture being used to form a "postcontacted" or second mixture of catalyst components that are contacted for a second period of time. Typically, the precontacted mixture can describe a mixture of transition metal compound (one or more than one), olefin monomer (or monomers), and organoaluminum compound (or compounds), before this mixture is contacted with an activator-support(s) and optional additional organoaluminum compound. Thus, precontacted describes components that are used to contact each other, but prior to contacting the components in the second, postcontacted mixture. Accordingly, this invention may occasionally distinguish between a component used to prepare the precontacted mixture and that component after the mixture has been prepared. For example, according to this description, it is possible for the precontacted organoaluminum compound, once it is contacted with the transition metal compound and the olefin monomer, to have reacted to form at least one different chemical compound, formulation, or structure from the distinct organoaluminum compound used to prepare the precontacted mixture. In this case, the precontacted organoaluminum compound or component is described as comprising an organoaluminum compound that was used to prepare the precontacted mixture.

Additionally, the precontacted mixture can describe a mixture of transition metal compound(s) and organoaluminum compound(s), prior to contacting this mixture with an activator-support(s). This precontacted mixture also can describe a mixture of transition metal compound(s), olefin monomer(s), and activator-support(s), before this mixture is contacted with an organoaluminum co-catalyst compound or compounds.

Similarly, the term "postcontacted" mixture is used herein to describe a second mixture of catalyst components that are contacted for a second period of time, and one constituent of which is the "precontacted" or first mixture of catalyst components that were contacted for a first period of time. Typically, the term "postcontacted" mixture is used herein to describe the mixture of transition metal compound(s), olefin monomer(s), organoaluminum compound(s), and activator-support(s) formed from contacting the precontacted mixture of a portion of these components with any additional components added to make up the postcontacted mixture. Often, the activator-support can comprise a chemically-treated solid oxide. For instance, the additional component added to make up the postcontacted mixture can be a chemically-treated solid oxide (one or more than one), and optionally, can include an organoaluminum compound which is the same as or different from the organoaluminum compound used to prepare the precontacted mixture, as described herein. Accordingly, this invention may also occasionally distinguish between a component used to prepare the postcontacted mixture and that component after the mixture has been prepared.

Although any methods, devices, and materials similar or equivalent to those described herein can be used in the practice or testing of the invention, the typical methods, devices and materials are herein described.

All publications and patents mentioned herein are incorporated herein by reference for the purpose of describing and disclosing, for example, the constructs and methodologies that are described in the publications, which might be used in connection with the presently described invention. The publications discussed throughout the text are provided solely for their disclosure prior to the filing date of the present application. Nothing herein is to be construed as an admission that the inventors are not entitled to antedate such disclosure by virtue of prior invention.

For any particular compound disclosed herein, any general or specific structure presented also encompasses all conformational isomers, regioisomers, and stereoisomers that may arise from a particular set of substituents, unless stated otherwise. Similarly, unless stated otherwise, the general or specific structure also encompasses all enantiomers, diastereomers, and other optical isomers whether in enantiomeric or racemic forms, as well as mixtures of stereoisomers, as would be recognized by a skilled artisan.

The term "hydrocarbyl" is used herein to specify a hydrocarbon radical group that includes, but is not limited to, aryl, alkyl, cycloalkyl, alkenyl, cycloalkenyl, cycloalkadienyl, alkynyl, aralkyl, aralkenyl, aralkynyl, and the like, and includes all substituted, unsubstituted, branched, linear, etc., derivatives thereof.

The term "alkane" is used herein to refer to a saturated hydrocarbon compound. The term "alkyl" group is used herein in accordance with the definition specified by IUPAC: a univalent group formed by removing a hydrogen atom from an alkane. Similarly, an "alkylene group" refers to a group formed by removing two hydrogen atoms from an alkane (either two hydrogen atoms from one carbon atom or one hydrogen atom from two different carbon atoms). An "alkyl," "alkylene," and "alkane" may be linear or branched unless otherwise specified. Furthermore, unless otherwise specified, alkyl groups described herein are intended to include all structural isomers, linear or branched, of a given moiety; for example, all enantiomers and all diastereomers are included within this definition. As an example, unless otherwise specified, the term propyl is meant to include n-propyl and iso-propyl, while the term butyl is meant to include n-butyl, iso-butyl, t-butyl, sec-butyl, and so forth. For instance, non-limiting examples of octyl isomers can include 2-ethyl hexyl and neooctyl.

A cycloalkane is a saturated cyclic hydrocarbon, with or without side chains (e.g., cyclobutane or methylcyclobutane). Unsaturated cyclic hydrocarbons having at least one non-aromatic endocyclic carbon-carbon double or one triple bond are cycloalkenes and cycloalkynes, respectively. Unsaturated cyclic hydrocarbons having more than one such multiple bond can further specify the number and/or position(s) of such multiple bonds (e.g., cycloalkadienes, cycloalkatrienes, and so forth). The unsaturated cyclic hydrocarbons may be further identified by the position of the carbon-carbon multiple bond(s). A "cycloalkyl group" is a univalent group derived by removing a hydrogen atom from a ring carbon atom from a cycloalkane, and representative cycloalkyls include cyclopentyl and cyclohexyl, for example.

The term "alkene" refers to a compound that has at least one non-aromatic carbon-carbon double bond. An "alkenyl" group is a univalent group derived from an alkene by removal of a hydrogen atom from any carbon atom of the alkene. Unless otherwise specified, alkenyl groups described herein are intended to include all structural isomers, linear or branched, of a given moiety, as well as any regiochemistry or positioning of the double bond. For example and unless otherwise specified, propen-1-yl (—CH═CHCH$_3$), propen-2-yl [(CH$_3$)C═CH$_2$], and propen-3-yl (—CH$_2$CH═CH$_2$) groups are all encompassed with a general disclosure of a propenyl group.

An "aryl" group refers to a generalized group formed by removing a hydrogen atom from an aromatic hydrocarbon ring carbon atom of an arene. One example of an "aryl" group is ortho-tolyl (o-tolyl), the structure of which is shown below.

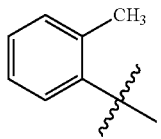

Similarly, an "arylene" group refers to a group formed by removing two hydrogen atoms from an arene. One example of an "arylene" group is para-phenylene (p-phenylene), the structure of which is shown below.

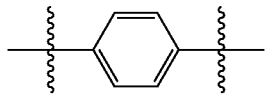 [SMILES: *c1ccc(*)cc1]

An "aralkyl" group is an aryl-substituted alkyl group having a free valance at a non-aromatic carbon atom. For example, a benzyl group is an "aralkyl" group.

Applicants disclose several types of ranges in the present invention. These include, but are not limited to, a range of number of atoms, a range of integers, a range of weight ratios, a range of molar ratios, a range of molecular weights, a range of temperatures, and so forth. When Applicants disclose or claim a range of any type, Applicants' intent is to disclose or claim individually each possible number that such a range could reasonably encompass, including end points of the range as well as any sub-ranges and combinations of sub-ranges encompassed therein. For example, when the Applicants disclose or claim a chemical moiety having a certain number of carbon atoms, Applicants' intent is to disclose or claim individually every possible number that such a range could encompass, consistent with the disclosure herein. For example, the disclosure that a moiety is a C$_1$ to C$_{18}$ hydrocarbyl group, or in alternative language a hydrocarbyl group having up to 18 carbon atoms, as used herein, refers to a moiety that can be selected independently from a hydrocarbyl group having 1, 2, 3, 4, 5, 6, 7, 8, 9, 10, 11, 12, 13, 14, 15, 16, 17, or 18 carbon atoms, as well as any range between these two numbers (for example, a C$_1$ to C$_8$ hydrocarbyl group), and also including any combination of ranges between these two numbers (for example, a C$_2$ to C$_4$ and a C$_{12}$ to C$_{16}$ hydrocarbyl group).

Similarly, another representative example follows for the ratio of Mw/Mn provided in one aspect of this invention. By a disclosure that the ratio of Mw/Mn can be in a range from about 6 to about 30, Applicants intend to recite that Mw/Mn can be about 6, about 7, about 8, about 9, about 10, about 11, about 12, about 13, about 14, about 15, about 16, about 17, about 18, about 19, about 20, about 21, about 22, about 22, about 23, about 24, about 25, about 26, about 27, about 28, about 29, or about 30. Additionally, the Mw/Mn ratio can be within any range from about 6 to about 30 (for example, from about 10 to about 25), and this also includes any combination of ranges between about 6 and about 30 (for example, Mw/Mn can be in a range from about 8 to about 12, or from about 16 to about 26). Likewise, all other ranges disclosed herein should be interpreted in a manner similar to these two examples.

Applicants reserve the right to proviso out or exclude any individual members of any such group, including any sub-ranges or combinations of sub-ranges within the group, that can be claimed according to a range or in any similar manner, if for any reason Applicants choose to claim less than the full measure of the disclosure, for example, to account for a reference that Applicants may be unaware of at the time of the filing of the application. Further, Applicants reserve the right to proviso out or exclude any individual substituents, analogs, compounds, ligands, structures, or groups thereof, or any members of a claimed group, if for any reason Applicants choose to claim less than the full measure of the disclosure, for example, to account for a reference that Applicants may be unaware of at the time of the filing of the application.

The terms "a," "an," "the," etc., are intended to include plural alternatives, e.g., at least one, unless otherwise specified. For instance, the disclosure of "an activator-support" or "a transition metal compound" is meant to encompass one, or mixtures or combinations of more than one, activator-support or transition metal compound, respectively.

While compositions and methods are described in terms of "comprising" various components or steps, the compositions and methods can also "consist essentially of" or "consist of" the various components or steps. For example, a catalyst composition of the present invention can comprise; alternatively, can consist essentially of; or alternatively, can consist of; (i) a transition metal compound and (ii) an activator.

The following abbreviations are used in this disclosure:
acac—acetylacetonate
Bz—benzyl
Et—ethyl
$^i$Pr—isopropyl
MAO—methylaluminoxane
Me—methyl
nBu—n-butyl
$^t$Bu—tert-butyl
THF—tetrahydrofuran
TIBA—triisobutylaluminum
TMEDA—N,N,N',N'-tetramethylethylenediamine
TMS—trimethyisilyl
TMSCl—trimethylsilylchloride

DETAILED DESCRIPTION OF THE INVENTION

The present invention is directed generally to new catalyst compositions, methods for preparing catalyst compositions, methods for using the catalyst compositions to polymerize olefins, the polymer resins produced using such catalyst compositions, and articles produced using these polymer resins. In particular, the present invention relates to transition metal complexes having a thiolate ligand, and catalyst compositions employing such transition metal complexes.

Transition Metal Complexes with Thiolate Ligands

The present invention discloses novel transition metal complexes or compounds having a thiolate ligand, and methods of making these complexes or compounds. In an aspect of this invention, the transition metal compound can have the formula:

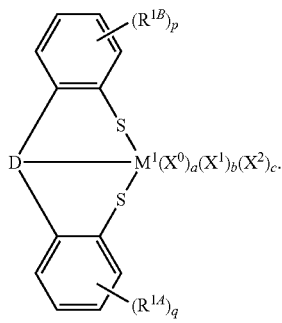

(I)

Generally, the selections of $M^1$, $R^{1A}$, $R^{1B}$, p, q, D, $X^0$, a, $X^1$, b, $X^2$, and c in formula (I) are independently described herein, and these selections may be combined in any combination to further describe the compound having formula (I). Unless otherwise specified, formula (I) above, any other structural formulas disclosed herein, and any transition metal species/complex/compound disclosed herein are not designed to show stereochemistry or isomeric positioning of the different moieties (e.g., these formulas are not intended to display cis or trans isomers, or R or S diastereoisomers), although such compounds are contemplated and encompassed by these formulas and/or structures.

In accordance with aspects of this invention, the metal in formula (I), $M^1$, can be a transition metal. For instance, $M^1$ can be a Group 3 to Group 8 transition metal. In one aspect, for example, $M^1$ can be a lanthanide, while in another aspect, $M^1$ can be Sc, Y, La, Ti, Zr, Hf, V, Nb, Ta, Cr, Mo, W, Mn, Tc, Re, Fe, Ru, or Os.

In a particular aspect contemplated herein, $M^1$ can be Sc, Y, La, Ti, Zr, Hf, V, Cr, Fe, Ta, or Nb. Alternatively, $M^1$ can be Sc; alternatively, $M^1$ can be Y; alternatively, $M^1$ can be La; alternatively, $M^1$ can be Ti; alternatively, $M^1$ can be Zr; alternatively, $M^1$ can be Hf; alternatively, $M^1$ can be V; alternatively, $M^1$ can be Cr; alternatively, $M^1$ can be Fe; alternatively, $M^1$ can be Ta; or alternatively, $M^1$ can be Nb. Yet, in another aspect, $M^1$ can be Sc, Y, or La. In still another aspect, $M^1$ can be Ti, Zr, Hf, or V. Accordingly, $M^1$ can be Ti, $M^1$ can be Zr, $M^1$ can be Hf, or $M^1$ can be V.

In accordance with yet another aspect, $M^1$ can be Co, Rh, Ir, Ni, Pd, Pt, Cu, Ag, Au, Zn, Cd, or Hg. As an example, $M^1$ can be Ni, Pd, Pt, or Cu; alternatively, $M^1$ can be Ni; alternatively, $M^1$ can be Pd; alternatively, $M^1$ can be Pt; or alternatively, $M^1$ can be Cu.

In formula (I), each $R^{1A}$ and $R^{1B}$ independently can be a $C_1$ to $C_{18}$ hydrocarbyl or hydrocarbylsilyl group. In an aspect, each $R^{1A}$ and $R^{1B}$ independently can be a $C_1$ to $C_{18}$ hydrocarbyl group; alternatively, a $C_1$ to $C_{12}$ hydrocarbyl group; or alternatively, a $C_1$ to $C_6$ hydrocarbyl group. In another aspect, each $R^{1A}$ and $R^{1B}$ independently can be a $C_1$ to $C_{18}$ alkyl group, a $C_2$ to $C_{18}$ alkenyl group, a $C_6$ to $C_{18}$ aryl group, or a $C_7$ to $C_{18}$ aralkyl group. For instance, each $R^{1A}$ and $R^{1B}$ independently can be a $C_1$ to $C_{15}$ alkyl group, a $C_2$ to $C_{15}$ alkenyl group, a $C_6$ to $C_{15}$ aryl group, or a $C_7$ to $C_{15}$ aralkyl group; alternatively, each $R^{1A}$ and $R^{1B}$ independently can be a $C_1$ to $C_{12}$ alkyl group, a $C_2$ to $C_{12}$ alkenyl group, a $C_6$ to $C_{12}$ aryl group, or a $C_7$ to $C_{12}$ aralkyl group; alternatively, $R^{1A}$ and $R^{1B}$ independently can be a $C_1$ to $C_{10}$ alkyl group, a $C_2$ to $C_{10}$ alkenyl group, a $C_6$ to $C_{10}$ aryl group, or a $C_7$ to $C_{10}$ aralkyl group; or alternatively, each $R^{1A}$ and $R^{1B}$ independently can be a $C_1$ to $C_5$ alkyl group, a $C_2$ to $C_5$ alkenyl group, a $C_6$ to $C_8$ aryl group, or a $C_7$ to $C_8$ aralkyl group.

Accordingly, in some aspects, the alkyl group which can be $R^{1A}$ and/or $R^{1B}$ in formula (I) can be a methyl group, an ethyl group, a propyl group, a butyl group, a pentyl group, a hexyl group, a heptyl group, an octyl group, a nonyl group, a decyl group, a undecyl group, a dodecyl group, a tridecyl group, a tetradecyl group, a pentadecyl group, a hexadecyl group, a heptadecyl group, or an octadecyl group; or alternatively, a methyl group, an ethyl group, a propyl group, a butyl group, a pentyl group, a hexyl group, a heptyl group, an octyl group, a nonyl group, or a decyl group. In some aspects, the alkyl group which can be $R^{1A}$ and/or $R^{1B}$ in formula (I) can be a methyl group, an ethyl group, a n-propyl group, an iso-propyl group, a n-butyl group, an iso-butyl group, a sec-butyl group, a tert-butyl group, a n-pentyl group, an iso-pentyl group, a sec-pentyl group, or a neopentyl group; alternatively, a methyl group, an ethyl group, an iso-propyl group, a tert-butyl group, or a neopentyl group; alternatively, a methyl group; alternatively, an ethyl group; alternatively, a n-propyl group; alternatively, an iso-propyl group; alternatively, a tert-butyl group; or alternatively, a neopentyl group.

Suitable alkenyl groups which can be $R^{1A}$ and/or $R^{1B}$ in formula (I) can include, but are not limited to, an ethenyl group, a propenyl group, a butenyl group, a pentenyl group, a hexenyl group, a heptenyl group, an octenyl group, a nonenyl group, a decenyl group, a undecenyl group, a dodecenyl group, a tridecenyl group, a tetradecenyl group, a pentadecenyl group, a hexadecenyl group, a heptadecenyl group, or an octadecenyl group. In one aspect, $R^{1A}$ and/or $R^{1B}$ in formula (I) can be an ethenyl group, a propenyl group, a butenyl group, a pentenyl group, a hexenyl group, a heptenyl group, an octenyl group, a nonenyl group, or a decenyl group, while in another aspect, $R^{1A}$ and/or $R^{1B}$ in formula (I) can be an ethenyl group, a propenyl group, a butenyl group, a pentenyl group, or a hexenyl group. For example, $R^{1A}$ and/or $R^{1B}$ can be an ethenyl group; alternatively, a propenyl group; alternatively, a butenyl group; alternatively, a pentenyl group; or alternatively, a hexenyl group. In yet another aspect, $R^{1A}$ and/or $R^{1B}$ can be a terminal alkenyl group, such as a $C_3$ to $C_{10}$ terminal alkenyl group or a $C_3$ to $C_8$ terminal alkenyl group.

In some aspects, the aryl group which can be $R^{1A}$ and/or $R^{1B}$ in formula (I) can be a phenyl group, a substituted phenyl group, a naphthyl group, or a substituted naphthyl group. In an aspect, the aryl group can be a phenyl group or a substituted phenyl group; alternatively, a naphthyl group or a substituted naphthyl group; alternatively, a phenyl group or a naphthyl group; or alternatively, a substituted phenyl group or a substituted naphthyl group. Substituents which can be utilized for the substituted phenyl groups or substituted naphthyl groups are independently disclosed herein and can be utilized without limitation to further describe the substituted phenyl groups or substituted naphthyl groups which can be $R^{1A}$ and/or $R^{1B}$ in formula (I).

In an aspect, the substituted phenyl group which can be $R^{1A}$ and/or $R^{1B}$ in formula (I) can be a 2-substituted phenyl group, a 3-substituted phenyl group, a 4-substituted phenyl group, a 2,4-disubstituted phenyl group, a 2,6-disubstituted phenyl group, 3,5-disubstituted phenyl group, or a 2,4,6-trisubstituted phenyl group. In other aspects, the substituted phenyl group can be a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group or a 2,6-disubstituted phenyl group; alternatively, a 2-substituted phenyl group; alternatively, a 3-substituted phenyl group; alternatively, a 4-substituted phenyl group; alternatively, a 2,4-disubstituted phenyl group; alternatively, a 2,6-disubstituted phenyl group; alternatively, 3,5-disubstituted phenyl group; or alternatively, a 2,4,6-trisubstituted phenyl group. Substituents which can be utilized for these specific substituted phenyl groups are independently disclosed herein and can be utilized without limitation to further describe these substituted phenyl groups which can be the $R^{1A}$ and/or $R^{1B}$ group in formula (I).

In some aspects, the aralkyl group which can be the $R^{1A}$ and/or $R^{1B}$ group in formula (I) can be a benzyl group or a substituted benzyl group. In an aspect, the aralkyl group can be a benzyl group or, alternatively, a substituted benzyl group. Substituents which can be utilized for the substituted aralkyl groups are independently disclosed herein and can be utilized without limitation to further describe the substituted aralkyl groups which can be the $R^{1A}$ and/or $R^{1B}$ group in formula (I).

In an aspect, each non-hydrogen substituent(s) for the substituted aryl group or substituted aralkyl group which can be the $R^{1A}$ and/or $R^{1B}$ group in formula (I) independently can be a $C_1$ to $C_{12}$ hydrocarbyl group; alternatively, a $C_1$ to $C_8$ hydrocarbyl group; or alternatively, a $C_1$ to $C_5$ hydrocarbyl group. Specific substituent hydrocarbyl groups are independently disclosed herein and can be utilized without limitation to further describe the substituents of the substituted aryl groups or substituted aralkyl groups which can be the $R^{1A}$ and/or $R^{1B}$ group in formula (I). For instance, the hydrocarbyl substituent can be an alkyl group, such as a methyl group, an ethyl group, a n-propyl group, an isopropyl group, a n-butyl group, a sec-butyl group, an isobutyl group, a tert-butyl group, a n-pentyl group, a 2-pentyl group, a 3-pentyl group, a 2-methyl-1-butyl group, a tert-pentyl group, a 3-methyl-1-butyl group, a 3-methyl-2-butyl group, or a neo-pentyl group, and the like.

In accordance with some aspects disclosed herein, each $R^{1A}$ and $R^{1B}$ independently can be a $C_1$ to $C_{18}$ hydrocarbylsilyl group; alternatively, a $C_1$ to $C_{12}$ hydrocarbylsilyl group; or alternatively, a $C_1$ to $C_6$ hydrocarbylsilyl group. In an aspect, the hydrocarbyl of the hydrocarbyl silyl can be any hydrocarbyl group disclosed herein (e.g., a $C_1$ to $C_{18}$ alkyl group, a $C_2$ to $C_{18}$ alkenyl group, a $C_6$ to $C_{18}$ aryl group, or a $C_7$ to $C_{18}$ aralkyl group). For example, an illustrative hydrocarbylsilyl group can include allyldimethylsilyl. In another aspect, the $C_1$ to $C_{18}$ hydrocarbylsilyl group can be a $C_1$ to $C_{18}$ trihydrocarbylsilyl group, such as, for example, a trialkylsilyl group or a triphenylsilyl group. Therefore, suitable hydrocarbylsilyl groups which can be the $R^{1A}$ and/or $R^{1B}$ group in formula (I) can include, but are not limited to, trimethylsilyl, triethylsilyl, tripropylsilyl (e.g., triisopropylsilyl), tributylsilyl, tripentylsilyl, triphenylsilyl, or allyldimethylsilyl.

Each $R^{1A}$ and $R^{1B}$ independently in formula (I) can be, in certain aspects, methyl, ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, phenyl, tolyl, benzyl, naphthyl, trimethylsilyl, triisopropylsilyl, triphenylsilyl, or allyldimethylsilyl. In another aspect, each $R^{1A}$ and $R^{1B}$ independently can be methyl, ethyl, propyl, butyl, pentyl, hexyl, heptyl, octyl, nonyl, or decyl; alternatively, methyl; alternatively, ethyl; alternatively, propyl; alternatively, butyl; alternatively, pentyl; alternatively, hexyl; alternatively, heptyl; alternatively, octyl; alternatively, nonyl; or alternatively, decyl. In another aspect, each $R^{1A}$ and $R^{1B}$ independently can be ethenyl, propenyl, butenyl, pentenyl, hexenyl, heptenyl, octenyl, nonenyl, or decenyl; alternatively, ethenyl; alternatively, propenyl; alternatively, butenyl; alternatively, pentenyl; alternatively, hexenyl; alternatively, heptenyl; alternatively, octenyl; alternatively, nonenyl; or alternatively, decenyl. In yet another aspect, each $R^{1A}$ and $R^{1B}$ independently can be phenyl, tolyl, benzyl, or naphthyl; alternatively, phenyl; alternatively, benzyl; alternatively, tolyl; or alternatively, naphthyl. In still another aspect, each $R^{1A}$ and $R^{1B}$ independently can be trimethylsilyl, triisopropylsilyl, triphenylsilyl, or allyldimethylsilyl; alternatively, trimethylsilyl; alternatively, triisopropylsilyl; alternatively, triphenylsilyl, or alternatively, allyldimethylsilyl.

In formula (I), p can be 1, 2, 3, or 4, and q can be 1, 2, 3, or 4. In some aspects, p can be 1 or 2, and q can be 1, 2, 3, or 4, while in other aspects, p can be 1, 2, 3, or 4, and q can be 1 or 2. For instance, p can be 1 or 2 and q can be 1 or 2, or p can be 1 and q can be 1. In circumstances where p is 2, 3, or 4, each $R^{1B}$ independently can be a $C_1$ to $C_{18}$ hydrocarbyl or hydrocarbylsilyl group (i.e., each $R^{1B}$ can be the same or different). Similarly, in circumstances where q is 2, 3, or 4, each $R^{1A}$ independently can be a $C_1$ to $C_{18}$ hydrocarbyl or hydrocarbylsilyl group (i.e., each $R^{1A}$ can be the same or different).

D in formula (I) can comprise a donor atom. In some aspects, D can be O (an oxygen atom), $NR^{1C}$, $PR^{1D}$, or a substituted or unsubstituted, saturated or unsaturated, $C_4$ to $C_{18}$ heterocyclic group. For instance, in certain aspects contemplated herein, D can be O. In other aspects, D can be $NR^{1C}$ or $PR^{1D}$, wherein $R^{1C}$ and $R^{1D}$ independently can be hydrogen or a $C_1$ to $C_{18}$ hydrocarbyl group. In instances where $R^{1C}$ and $R^{1D}$ are not hydrogen atoms, $R^{1C}$ and $R^{1D}$, independently, can be any $C_1$ to $C_{18}$ hydrocarbyl group disclosed herein. For example, $R^{1C}$ and $R^{1D}$ independently can be any $C_1$ to $C_{18}$ alkyl group, $C_2$ to $C_{18}$ alkenyl group, $C_6$ to $C_{18}$ aryl group, or $C_7$ to $C_{18}$ aralkyl group disclosed herein. Specific non-limiting examples of groups which can be $R^{1C}$ and/or $R^{1D}$ can include methyl, ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, phenyl, tolyl, benzyl, or naphthyl. Accordingly, $R^{1C}$ and/or $R^{1D}$ can be, in certain aspects, methyl, ethyl, propyl, butyl, pentyl, hexyl, heptyl, octyl, nonyl, decyl, phenyl, or benzyl.

In another aspect, D in formula (I) can be a substituted or unsubstituted, saturated or unsaturated, $C_4$ to $C_{18}$ heterocyclic group. Alternatively, D can be a $C_4$-$C_{15}$ heterocyclic group, a $C_4$-$C_{12}$ heterocyclic group, or a $C_4$-$C_8$ heterocyclic group. The heteroatom in the heterocyclic group can be, for instance, O, N, or S, and is oriented towards the transition metal. Heterocyclic groups containing two heteroatoms (either the same or different) also can used as D in formula (I), wherein at least one of the heteroatoms is oriented towards the transition metal. Illustrative examples of D can include, but are not limited to, the following heterocyclic groups:

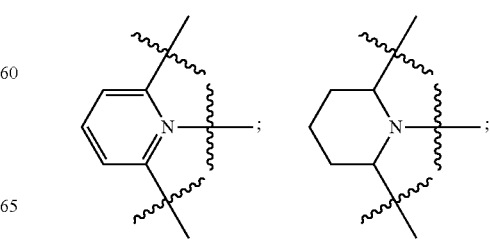

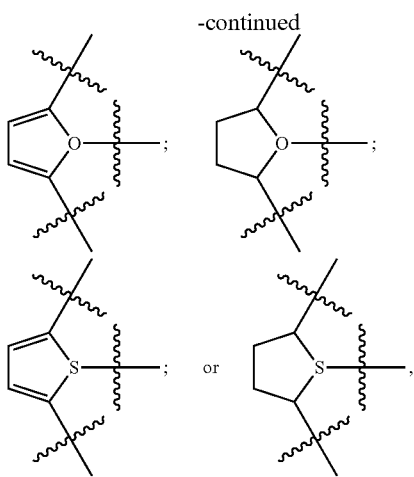

and the like. In yet another aspect, D can be O, $NR^{1C}$, or one of the following groups:

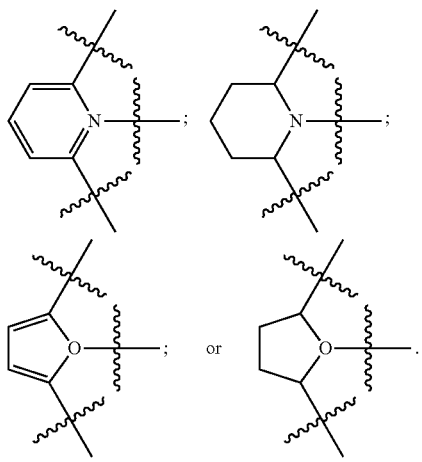

Alternatively, D can be O, or D can be $NR^{1C}$.

Each $X^0$ in formula (I) independently can be neutral ligand, and the integer a in formula (I) can be 0, 1 or 2. In an aspect, suitable neutral ligands can include sigma-donor solvents that contain a coordinating atom (or atoms) that can coordinate to a transition metal atom in formula (I). Examples of suitable coordinating atoms in the neutral ligands can include, but are not limited to, O, N, S, and P, or combinations of these atoms. Unless otherwise specified, the neutral ligand can be unsubstituted or can be substituted. Substituent groups are independently described herein and can be utilized, without limitation to further describe a neutral ligand which can be utilized as $X^0$ in formula (I). In some aspects, the neutral ligand can be a Lewis base. When the integer a is equal to 2, it is contemplated that the two neutral ligands can be either the same or different.

In an aspect, each neutral ligand, $X^0$, independently can be an ether, a thioether, an amine, a nitrile, or a phosphine. In another aspect, each neutral ligand independently can be an acyclic ether, a cyclic ether, an acyclic thioether, a cyclic thioether, a nitrile, an acyclic amine, a cyclic amine, an acyclic phosphine, or a cyclic phosphine. In other aspects, each neutral ligand independently can be an acyclic ether or a cyclic ether; alternatively, an acyclic thioether or a cyclic thioether; alternatively, an acyclic amine or a cyclic amine; alternatively, an acyclic phosphine or a cyclic phosphine; alternatively, an acyclic ether; alternatively, a cyclic ether; alternatively, an acyclic thioether; alternatively, a cyclic thioether; alternatively, a nitrile; alternatively, an acyclic amine; alternatively, a cyclic amine; alternatively, an acyclic phosphine; or alternatively, a cyclic phosphine. Further, each neutral ligand independently can include any substituted analogs of any acyclic ether, cyclic ether, acyclic thioether, cyclic thioether, nitrile, acyclic anine, cyclic amine, acyclic phosphine, or cyclic phosphine, as disclosed herein.

In an aspect, each neutral ligand independently can be a nitrile having the formula $R^1C\equiv N$, an ether having the formula $R^2-O-R^3$, a thioether having the formula $R^4-S-R^5$, an amine having the formula $NR^6R^7R^8$, $NHR^6R^7$, or $NH_2R^6$, or a phosphine having the formula $PR^9R^{10}R^{11}$, $PHR^9R^{10}$, or $PH_2R^9$; alternatively, a nitrile having the formula $R^1C\equiv N$, an ether having the formula $R^2-O-R^3$, a thioether having the formula $R^4-S-R^5$, an amine having the formula $NR^6R^7R^8$, or a phosphine having the formula $PR^9R^{10}R^{11}$; or alternatively, a nitrile having the formula $R^1C\equiv N$, an ether having the formula $R^2-O-R^3$, a thioether having the formula $R^4-S-R^5$, an amine having the formula $NR^6R^7R^8$, or a phosphine having the formula $PR^9R^{10}R^{11}$. In an aspect, each neutral ligand independently can be a nitrile having the formula $R^1C\equiv N$; alternatively, an ether having the formula $R^2-O-R^3$; alternatively, a thioether having the formula $R^4-S-R^5$; alternatively, an amine having the formula $NR^6R^7R^8$, $NHR^6R^7$, or $NH_2R^6$; alternatively, a phosphine having the formula $PR^9R^{10}R^{11}$, $PHR^9R^{10}$, or $PH_2R^9$; or alternatively, a phosphine having the formula $PR^9R^{10}R^{11}$.

In an aspect, $R^1$ of the nitrile having the formula $R^1C\equiv N$, $R^2$ and $R^3$ of the ether having formula $R^2-O-R^3$, $R^4$ and $R^5$ of the thioether having the formula $R^4-S-R^5$, $R^6$, $R^7$, and $R^8$ of the amine having the formula $NR^6R^7R^8$, $NHR^6R^7$, or $NH_2R^6$, and $R^9$, $R^{10}$, and $R^{11}$ of the phosphine having the formula $PR^9R^{10}R^{11}$, $PHR^9R^{10}$, or $PH_2R^9$, independently can be a $C_1$ to $C_{18}$ hydrocarbyl group; alternatively, a $C_1$ to $C_{15}$ hydrocarbyl group; alternatively, a $C_1$ to $C_{12}$ hydrocarbyl group; alternatively, a $C_1$ to $C_8$ hydrocarbyl group; or alternatively, a $C_1$ to $C_6$ hydrocarbyl group. It should also be noted that $R^2$ and $R^3$ of the ether having formula $R^2-O-R^3$, $R^4$ and $R^5$ of the thioether having the formula $R^4-S-R^5$, any two of $R^6$, $R^7$, and $R^8$ of the amine having the formula $NR^6R^7R^8$ or $NHR^6R^7$, and/or any two of $R^9$, $R^{10}$, and $R^{11}$ of the phosphine having the formula $PR^9R^{10}R^{11}$ or $PHR^9R^{10}$ can be joined to form a ring containing the ether oxygen atom, the thioether sulfur atom, the amine nitrogen atom, or the phosphine phosphorus atom to form a cyclic ether, thioether, amine, or phosphine, respectively, as described herein in regards to cyclic ethers, thioethers, amines, and phosphines.

In an aspect, $R^1$ of the nitrile having the formula $R^1C\equiv N$, $R^2$ and $R^3$ of the ether having formula $R^2-O-R^3$, $R^4$ and $R^5$ of the thioether having the formula $R^4-S-R^5$, $R^6$, $R^7$, and $R^8$ of the amine having the formula $NR^6R^7R^8$, $NHR^6R^7$, or $NH_2R^6$, and $R^9$, $R^{10}$, and $R^{11}$ of the phosphine having the formula $PR^9R^{10}R^{11}$, $PHR^9R^{10}$, or $PH_2R^9$, independently be any hydrocarbyl group disclosed herein. The hydrocarbyl group can be, for instance, any alkyl group, cycloalkyl group, aryl group, or aralkyl group disclosed herein.

In another aspect, each neutral ligand, $X^0$, in formula (I) independently can be a $C_2$-$C_{30}$ ether, a $C_2$-$C_{30}$ thioether, a $C_2$-$C_{20}$ nitrile, a $C_1$-$C_{30}$ amine, or a $C_1$-$C_{30}$ phosphine; alternatively, a $C_2$-$C_{18}$ ether; alternatively, a $C_2$-$C_{18}$ thioether; alternatively, a $C_2$-$C_{12}$ nitrile; alternatively, a $C_1$-$C_{18}$ amine; or alternatively, a $C_1$-$C_{18}$ phosphine. In some aspects, each neutral ligand independently can be a $C_2$-$C_{12}$ ether, a $C_2$-$C_{18}$ thioether, a $C_2$-$C_8$ nitrile, a $C_1$-$C_{12}$ amine, or a $C_1$-$C_{12}$ phosphine; alternatively, a $C_2$-$C_{10}$ ether; alternatively, a $C_2$-$C_{10}$ thioether; alternatively, a $C_2$-$C_6$ nitrile; alternatively, a $C_1$-$C_8$ amine; or alternatively, a $C_1$-$C_8$ phosphine.

Suitable ethers which can be utilized as a neutral ligand, either alone or in combination, can include, but are not limited to, dimethyl ether, diethyl ether, dipropyl ether, dibutyl ether, methyl ethyl ether, methyl propyl ether, methyl butyl ether, diphenyl ether, ditolyl ether, tetrahydrofuran, 2-methyltetrahydrofuran, 2,5-dimethyltetrahydrofuran, 2,3-dihydrofuran, 2,5-dihydrofuran, furan, benzofuran, isobenzofuran, dibenzofuran, tetrahydropyran, 3,4-dihydro-2H-pyran, 3,6-dihydro-2H-pyran, 2H-pyran, 4H-pyran, 1,3-dioxane, 1,4-dioxane, morpholine, and the like, including substituted derivatives thereof.

Suitable thioethers which can be utilized as a neutral ligand, either alone or in combination, can include, but are not limited to, dimethyl thioether, diethyl thioether, dipropyl thioether, dibutyl thioether, methyl ethyl thioether, methyl propyl thioether, methyl butyl thioether, diphenyl thioether, ditolyl thioether, thiophene, benzothiophene, tetrahydrothiophene, thiane, and the like, including substituted derivatives thereof.

Suitable nitriles which can be utilized as a neutral ligand, either alone or in combination, can include, but are not limited to, acetonitrile, propionitrile, butyronitrile, benzonitrile, 4-methylbenzonitrile, and the like, including substituted derivatives thereof.

Suitable amines which can be utilized as a neutral ligand, either alone or in combination, can include, but are not limited to, methyl amine, ethyl amine, propyl amine, butyl amine, dimethyl amine, diethyl amine, dipropyl amine, dibutyl amine, trimethyl amine, triethyl amine, tripropyl amine, tributyl amine, aniline, diphenylamine, triphenylamine, tolylamine, xylylamine, ditolylamine, pyridine, quinoline, pyrrole, indole, 2-methylpyridine, 3-methylpyridine, 4-methylpyridine, 2,5-dimethylpyrrole, 2,5-diethlylpyrrole, 2,5-dipropylpyrrole, 2,5-dibutylpyrrole, 2,4-dimethylpyrrole, 2,4-diethylpyrrole, 2,4-dipropylpyrrole, 2,4-dibutylpyrrole, 3,4-dimethylpyrrole, 3,4-diethylpyrrole, 3,4-dipropylpyrrole, 3,4-dibutylpyrrole, 2-methylpyrrole, 2-ethylpyrrole, 2-propylpyrrole, 2-butylpyrrole, 3-methylpyrrole, 3-ethylpyrrole, 3-propylpyrrole, 3-butylpyrrole, 3-ethyl-2,4-dimethylpyrrole, 2,3,4,5-tetramethylpyrrole, 2,3,4,5-tetraethylpyrrole, and the like, including substituted derivatives thereof. Suitable amines can be primary amines, secondary amines, or tertiary amines.

Suitable phosphines which can be utilized as a neutral ligand, either alone or in combination, can include, but are not limited to, trimethylphosphine, triethylphosphine, tripropylphosphine, tributylphosphine, phenylphosphine, tolylphosphine, diphenylphosphine, ditolylphosphine, triphenylphosphine, tritolylphosphine, methyldiphenylphosphine, dimethylphenylphosphine, ethyldiphenylphosphine, diethylphenylphosphine, and the like, including substituted derivatives thereof.

In an aspect of the invention, each neutral ligand independently can be azetidine, oxetane, thietane, dioxetane, dithietane, tetrahydropyrrole, dihydropyrrole, pyrrole, indole, isoindole, tetrahydrofuran, 2-methyltetrahydrofuran, 2,5-dimethyltetrahydrofuran, dihydrofuran, furan, benzofuran, isobenzofuran, tetrahydrothiophene, dihydrothiophene, thiophene, benzothiophene, isobenzothiophene, imidazolidine, pyrazole, imidazole, oxazolidine, oxazole, isoxazole, thiazolidine, thiazole, isothiazole, benzothiazole, dioxolane, dithiolane, triazole, dithiazole, piperidine, pyridine, dimethyl amine, diethyl amine, tetrahydropyran, dihydropyran, pyran, thiane, piperazine, diazine, oxazine, thiazine, dithiane, dioxane, dioxin, triazine, triazinane, trioxane, oxepin, azepine, thiepin, diazepine, morpholine, quinoline, tetrahydroquinone, bicyclo[3.3.1]tetrasiloxane, or acetonitrile; alternatively, azetidine, oxetane, thietane, dioxetane, dithietane, tetrahydropyrrole, tetrahydrofuran, 2-methyltetrahydrofuran, 2,5-dimethyltetrahydrofuran, tetrahydrothiophene, imidazolidine, oxazolidine, oxazole, thiazolidine, thiazole, dioxolane, dithiolane, piperidine, tetrahydropyran, pyran, thiane, piperazine, oxazine, thiazine, dithiane, dioxane, dioxin, triazinane, trioxane, azepine, thiepin, diazepine, morpholine, 1,2-thiazole, or bicyclo[3.3.1]tetrasiloxane; alternatively, tetrahydropyrrole, tetrahydrofuran, 2-methyltetrahydrofuran, 2,5-dimethyltetrahydrofuran, tetrahydrothiophene, oxazolidine, thiazolidine, dioxolane, dithiolane, dithiazole, piperidine, tetrahydropyran, pyran, thiane, piperazine, dithiane, dioxane, dioxin, trioxane, or morpholine; alternatively, tetrahydrofuran, 2-methyltetrahydrofuran, 2,5-dimethyltetrahydrofuran, tetrahydrothiophene, dioxolane, dithiolane, tetrahydropyran, pyran, thiane, dithiane, dioxane, dioxin, or trioxane; alternatively, tetrahydrofuran, dioxolane, tetrahydropyran, dioxane, or trioxane; alternatively, pyrrole, furan, pyrazole, imidazole, oxazole, isoxazole, thiazole, isothiazole, triazole, pyridine, dimethyl amine, diethyl amine, diazine, triazine, or quinoline; alternatively, pyrrole, furan, imidazole, oxazole, thiazole, triazole, pyridine, diethyl amine, diethyl amine, diazine, or triazine; or alternatively, furan, oxazole, thiazole, triazole, pyridine, diazine, or triazine. In some aspects, each neutral ligand independently can be azetidine; alternatively, oxetane; alternatively, thietane; alternatively, dioxetane; alternatively, dithietane; alternatively, tetrahydropyrrole; alternatively, dihydropyrrole, alternatively, pyrrole; alternatively, indole; alternatively, isoindole; alternatively, tetrahydrofuran; alternatively, 2-methyltetrahydrofuran; alternatively, 2,5-dimethyltetrahydrofuran; alternatively, dihydropyrrole; alternatively, furan; alternatively, benzofuran; alternatively, isobenzofuran; alternatively, tetrahydrothiophene; alternatively, dihydrothiophene; alternatively, thiophene; alternatively, benzothiophene; alternatively, isobenzothiophene; alternatively, imidazolidine; alternatively, pyrazole; alternatively, imidazole; alternatively, oxazolidine; alternatively, oxazole; alternatively, isoxazole; alternatively, thiazolidine; alternatively, thiazole; alternatively, benzothiazole; alternatively, isothiazole; alternatively, dioxolane; alternatively, dithiolane; alternatively, triazole; alternatively, dithiazole; alternatively, piperidine; alternatively, pyridine; alternatively, dimethyl amine; alternatively, diethyl amine; alternatively, tetrahydropyran; alternatively, dihydropyran; alternatively, pyran; alternatively, thiane; alternatively, piperazine; alternatively, diazine; alternatively, oxazine; alternatively, thiazine; alternatively, dithiane; alternatively, dioxane; alternatively, dioxin; alternatively, triazine; alternatively, triazinane; alternatively, trioxane; alternatively, oxepin; alternatively, azepine; alternatively, thiepin; alternatively, diazepine; alternatively, morpholine; alternatively, quinoline; alternatively, tetrahydroquinone; alternatively, bicyclo[3.3.1]tetrasiloxane; or alternatively, acetonitrile.

In another aspect, each neutral ligand independently can be azetidine, tetrahydropyrrole, dihydropyrrole, pyrrole, indole, isoindole, imidazolidine, pyrazole, imidazole, oxazolidine, oxazole, isoxazole, thiazolidine, thiazole, isothiazole, triazole, benzotriazole, dithiazole, piperidine, pyridine, dimethyl amine, diethyl amine, piperazine, diazine, oxazine, thiazine, triazine, azepine, diazepine, morpholine, quinoline, or tetrahydroisoquinoline. In another aspect, each neutral ligand independently can be thietane, dithietane, tetrahydrothiophene, dihydrothiophene, thiophene, benzothiophene, isobenzothiophene, thiazolidine, thiazole, isothiazole, dithiolane, dithiazole, thiane, thiazine, dithiane, or thiepin. In another aspect, each neutral ligand independently can be tetrahydrofuran, furan, methyltetrahydrofuran, dihydrofuran, tetrahydropyran, 2,3-dihydropyran, 1,3-dioxane, 1,4-dioxane, morpholine, N-methylmorpholine, acetonitrile, propionitrile, butyronitrile, benzonitrile, pyridine, ammonia, methyl amine, ethyl amine, dimethyl amine, diethyl amine, trimethyl amine, triethyl amine, trimethylphosphine, triethylphosphine, triphenylphosphine, tri-n-butylphosphine, methyl isocyanide, n-butyl isocyanide, phenyl isocyanide, $SMe_2$, thiophene, or tetrahydrothiophene. In another aspect, each neutral ligand independently can be tetrahydrofuran, methyltetrahydrofuran, tetrahydropyran, 1,4-dioxane, acetonitrile, pyridine, dimethyl amine, diethyl amine, ammonia, trimethyl amine, triethyl amine, trimethylphosphine, triethylphosphine, triphenylphosphine, $SMe_2$, or tetrahydrothiophene; alternatively, tetrahydrofuran, methyltetrahydrofuran, tetrahydropyran, or 1,4-dioxane; alternatively, ammonia, trimethylamine, or triethylamine; or alternatively, trimethylphosphine, triethylphosphine, or triphenylphosphine. Yet, in another aspect, each neutral ligand independently can be tetrahydrofuran, acetonitrile, pyridine, ammonia, dimethyl amine, diethyl amine, trimethyl amine, trimethylphosphine, or triphenylphosphine; alternatively, tetrahydrofuran, acetonitrile, pyridine, dimethyl amine, diethyl amine, trimethyl amine, trimethylphosphine, or triphenylphosphine; alternatively, tetrahydrofuran, acetonitrile, dimethyl amine, diethyl amine, or pyridine; alternatively, tetrahydrofuran; alternatively, acetonitrile; alternatively, dimethyl amine; alternatively, diethyl amine; or alternatively, pyridine.

Each $X^1$ in formula (I) independently can be a monoanionic ligand, and the integer b in formula (I) can be 0, 1, 2, 3, or 4. In some aspects, suitable monoanionic ligands can include hydrogen (hydride), a halide, or a $C_1$ to $C_{18}$ hydrocarbyl group, hydrocarbyloxide group, hydrocarbylamino group, hydrocarbylsilyl group, or hydrocarbylaminosilyl group. If there are two or more $X^1$ ligands present in formula (I), each $X^1$ ligand can be the same or a different monoanionic ligand.

In one aspect, each $X^1$ in formula (I) independently can be hydrogen, a halide (e.g., F, Cl, Br, or I), or a $C_1$ to $C_{18}$ hydrocarbyl group, hydrocarbyloxide group, hydrocarbylamino group, hydrocarbylsilyl group, or hydrocarbylaminosilyl group. In another aspect, each $X^1$ independently can be hydrogen, a halide, or a $C_1$ to $C_{12}$ hydrocarbyl group, hydrocarbyloxide group, hydrocarbylamino group, hydrocarbylsilyl group, or hydrocarbylaminosilyl group. In yet another aspect, each $X^1$ independently can be hydrogen, a halide, or a $C_1$ to $C_{10}$ hydrocarbyl group, hydrocarbyloxide group, hydrocarbylamino group, hydrocarbylsilyl group, or hydrocarbylaminosilyl group. In still another aspect, each $X^1$ independently can be hydrogen, a halide, or a $C_1$ to $C_8$ hydrocarbyl group, hydrocarbyloxide group, hydrocarbylamino group, hydrocarbylsilyl group, or hydrocarbylaminosilyl group.

The hydrocarbyl group which can be $X^1$ in formula (I) can be any $C_1$ to $C_{18}$ hydrocarbyl group, any $C_1$ to $C_{12}$ hydrocarbyl group, any $C_1$ to $C_{10}$ hydrocarbyl group, or any $C_1$ to $C_8$ hydrocarbyl group, disclosed herein. A hydrocarbyloxide group is used generically herein to include, for instance, alkoxy, aryloxy, and -(alkyl or aryl)-O-(alkyl or aryl) groups, and these groups can comprise up to about 18 carbon atoms (e.g., $C_1$ to $C_{18}$, $C_1$ to $C_{12}$, $C_1$ to $C_{10}$, or $C_1$ to $C_8$ hydrocarbyloxide groups). Illustrative and non-limiting examples of hydrocarbyloxide groups can include methoxy, ethoxy, propoxy, butoxy, phenoxy, substituted phenoxy, acetylacetonate (acac), and the like. The term hydrocarbylamino group is used generically herein to refer collectively to, for instance, alkylamino, arylamino, dialkylamino, diarylamino, and -(alkyl or aryl)-N-(alkyl or aryl) groups, and the like. Unless otherwise specified, the hydrocarbylamino groups which can be $X^1$ in of this invention can comprise up to about 18 carbon atoms (e.g., $C_1$ to $C_{18}$, $C_1$ to $C_{12}$, $C_1$ to $C_{10}$, or $C_1$ to $C_8$ hydrocarbylamino groups). The hydrocarbylsilyl group which can be $X^1$ in formula (I) can be any $C_1$ to $C_{18}$ hydrocarbylsilyl group, any $C_1$ to $C_{12}$ hydrocarbylsilyl group, any $C_1$ to $C_{10}$ hydrocarbylsilyl group, or any $C_1$ to $C_8$ hydrocarbylsilyl group, disclosed herein. A hydrocarbylaminosilyl group is used herein to refer to groups containing at least one hydrocarbon moiety, at least one N atom, and at least one Si atom. Illustrative and non-limiting examples of hydrocarbylaminosilyl groups which can be $X^1$ can include, but are not limited to —$N(SiMe_3)_2$, —$N(SiEt)_2$, and the like. Unless otherwise specified, the hydrocarbylaminosilyl groups which can be $X^1$ can comprise up to about 18 carbon atoms (e.g., $C_1$ to $C_{18}$, $C_1$ to $C_{12}$, $C_1$ to $C_{10}$, or $C_1$ to $C_8$ hydrocarbylaminosilyl groups).

In accordance with an aspect of this invention, each $X^1$ in formula (I) independently can be a halide; alternatively, a $C_1$ to $C_{18}$ hydrocarbyl group; alternatively, a $C_1$ to $C_{18}$ hydrocarbyloxide group; alternatively, a $C_1$ to $C_{18}$ hydrocarbylamino group; alternatively, a $C_1$ to $C_{18}$ hydrocarbylsilyl group; or alternatively, a $C_1$ to $C_{18}$ hydrocarbylaminosilyl group. In accordance with another aspect, each $X^1$ can be hydrogen; alternatively, F; alternatively, Cl; alternatively, Br; alternatively, I; alternatively, a $C_1$ to $C_{18}$ hydrocarbyl group; alternatively, a $C_1$ to $C_{18}$ hydrocarbyloxide group; alternatively, a $C_1$ to $C_{18}$ hydrocarbylamino group; alternatively, a $C_1$ to $C_{18}$ hydrocarbylsilyl group; or alternatively, a $C_1$ to $C_{18}$ hydrocarbylaminosilyl group. In accordance with yet another aspect, each $X^1$, or at least one $X^1$, can be hydrogen, a halide, methyl, phenyl, benzyl, an alkoxy, an aryloxy, acetylacetonate, an alkylamino, a dialkylamino, a trihydrocarbylsilyl, or a hydrocarbylaminosilyl; alternatively, hydrogen, a halide, methyl, phenyl, or benzyl; alternatively, an alkoxy, an aryloxy, or acetylacetonate; alternatively, an alkylamino or a dialkylamino; alternatively, a trihydrocarbylsilyl or hydrocarbylaminosilyl; alternatively, hydrogen or a halide; alternatively, methyl, phenyl, benzyl, an alkoxy, an aryloxy, acetylacetonate, an alkylamino, or a dialkylamino; alternatively, hydrogen; alternatively, a halide; alternatively, methyl; alternatively, phenyl; alternatively, benzyl; alternatively, an alkoxy; alternatively, an aryloxy; alternatively, acetylacetonate; alternatively, an alkylamino; alternatively, a dialkylamino; alternatively, a trihydrocarbylsilyl; or alternatively, a hydrocarbylaminosilyl. In these and other aspects, the alkoxy, aryloxy, alkylamino, dialkylamino, trihydrocarbylsilyl, and hydrocarbylaminosilyl can be a $C_1$ to $C_{18}$, a $C_1$ to $C_{12}$, a $C_1$ to $C_{10}$, or a $C_1$ to $C_8$ alkoxy, aryloxy, alkylamino, dialkylamino, trihydrocarbylsilyl, and hydrocarbylaminosilyl.

$X^2$ in formula (I) can be a dianionic ligand, and the integer c in formula (I) can be either 0 or 1. In one aspect, $X^2$ can be =O, =$NR^{2A}$, or =$CR^{2A}R^{2C}$. In another aspect, $X^2$ can be =O; alternatively, $X^2$ can be =$NR^{2A}$; or alternatively, $X^2$ can be =$CR^{2B}R^{2C}$. Independently, $R^{2A}$, $R^{2B}$, and $R^{2C}$ can be hydrogen or any $C_1$ to $C_{18}$ hydrocarbyl group disclosed herein; alternatively, hydrogen or any $C_1$ to $C_{12}$ hydrocarbyl group disclosed herein; alternatively, hydrogen or any $C_1$ to $C_{10}$ hydrocarbyl group disclosed herein; or alternatively, hydrogen or any $C_1$ to $C_8$ hydrocarbyl group disclosed herein. As an example, $R^{2A}$, $R^{2B}$, and $R^{2C}$ independently can be hydrogen or any $C_1$ to $C_{12}$, $C_1$ to $C_8$, or $C_1$ to $C_6$, alkyl group disclosed herein.

An oxidation state of the metal in formula (I), $M^1$, generally can be equal to (b+2c+2). For example, the most common oxidation state for Ti, Zr, Hf can be +4; therefore, c can be equal to zero and b can be equal to 2 (two monoanionic ligands), or b can be equal to zero and c can be equal to 1 (one dianionic ligand). The most common oxidation state for V and Ta can be +5; therefore, for instance, b can be equal to one (one monoanionic ligand) and c can be equal to 1 (one dianionic ligand).

In accordance with one aspect of the present invention, $M^1$ in formula (I) can be a transition metal, and $R^{1A}$ and $R^{1B}$ independently can be a $C_1$ to $C_{18}$ hydrocarbyl or hydrocarbylsilyl group, wherein p and q independently can be 1, 2, 3, or 4. In this aspect, D can be O, $NR^{1C}$, $PR^{1D}$, or a substituted or unsubstituted, saturated or unsaturated, $C_4$ to $C_{18}$ heterocyclic group, wherein $R^{1C}$ and $R^{1D}$ independently can be hydrogen or a $C_1$ to $C_{18}$ hydrocarbyl group. In these and other aspects, each $X^0$ independently can be a neutral ligand (a can be 0, 1, or 2), each $X^1$ independently can be a monoanionic ligand (b can be 0, 1, 2, 3, or 4), and $X^2$ can be a dianionic ligand (c can be either 0 or 1).

In accordance with another aspect, $M^1$ in formula (I) can be a Group 3 to Group 8 transition metal, and each $R^{1A}$ and $R^{1B}$ independently can be methyl, ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, phenyl, tolyl, benzyl, naphthyl, trimethylsilyl, triisopropylsilyl, triphenylsilyl, or allyldimethylsilyl, wherein p and q independently can be 1, 2, 3, or 4. In this aspect, D can be O, $NR^{1C}$ or $PR^{1D}$ (wherein $R^{1C}$ and $R^{1D}$ independently can be hydrogen or a $C_1$ to $C_{18}$ hydrocarbyl group, e.g., a $C_1$ to $C_{18}$ alkyl group), or

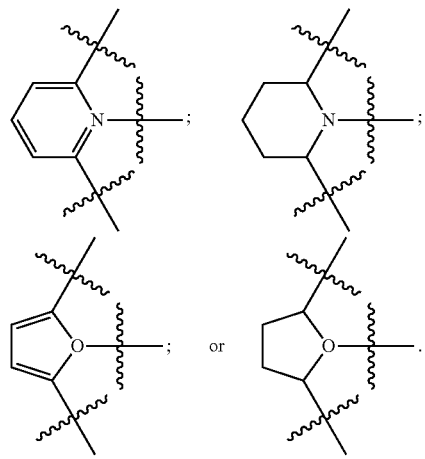

In these and other aspects, each $X^0$ independently can be an ether, a thioether, an amine, a nitrile, or a phosphine (a can be 0, 1, or 2), each $X^1$ independently can be hydrogen, a halide, or a $C_1$ to $C_{18}$ hydrocarbyl group, hydrocarbyloxide group, hydrocarbylamino group, hydrocarbylsilyl group, or hydrocarbylaminosilyl group (b can be 0, 1, 2, 3, or 4), and $X^2$ can be $=O$, $=NR^{2A}$, or $=CR^{2B}R^{2C}$, wherein $R^{2A}$, $R^{2B}$, and $R^{2C}$ independently can be hydrogen or a $C_1$ to $C_{18}$ hydrocarbyl group (c can be either 0 or 1).

In accordance with a yet another aspect, $M^1$ in formula (I) can be Sc, Y, La, Ti, Zr, Hf, V, Cr, Fe, Ta, or Nb, and each $R^{1A}$ and $R^{1B}$ independently can be methyl, ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, phenyl, tolyl, benzyl, naphthyl, trimethylsilyl, triisopropylsilyl, triphenylsilyl, or allyldimethylsilyl, wherein p and q independently can be 1 or 2. In this aspect, D can be O or $NR^{1C}$ (wherein $R^{1C}$ can be hydrogen, methyl, ethyl, propyl, butyl, pentyl, hexyl, heptyl, octyl, nonyl, decyl, phenyl, or benzyl). In these and other aspects, each $X^0$ independently can be an ether, a thioether, an amine, a nitrile, or a phosphine (e.g., tetrahydrofuran, acetonitrile, pyridine, dimethyl amine, diethyl amine, trimethyl amine, trimethylphosphine, or triphenylphosphine), wherein a can be 0, 1, or 2; each $X^1$ independently can be hydrogen, a halide, methyl, phenyl, benzyl, an alkoxy, an aryloxy, acetylacetonate, an alkylamino, a dialkylamino, a trihydrocarbylsilyl, or a hydrocarbylaminosilyl, wherein b can be 0, 1, 2, 3, or 4; and X can be $=O$, $=NR^{2A}$, or $=CR^{2B}R^{2C}$, wherein $R^{2A}$, $R^{2B}$, and $R^{2C}$ independently can be hydrogen or a $C_1$ to $C_{18}$ hydrocarbyl group (e.g., a $C_1$ to $C_{18}$ alkyl group or a $C_1$ to $C_8$ alkyl group), wherein c can be either 0 or 1.

Other aspects disclosed herein are directed to transition metal compounds having the formula:

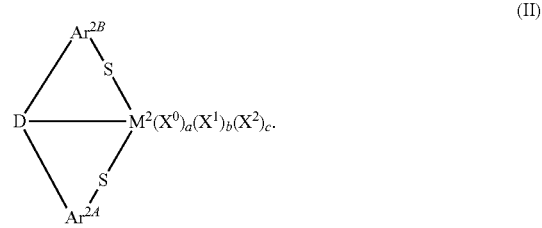

(II)

Generally, the selections of $M^2$, $Ar^{2A}$, $Ar^{2B}$, D, $X^0$, a, $X^1$, b, $X^2$, and c in formula (II) are independently described herein, and these selections may be combined in any combination to further describe the compound having formula (II). $M^2$ can be a Group 3 to Group 8 transition metal, including lathanides and actinides. In one aspect, $M^2$ can be a Group 3 to Group 8 transition metal, while in another aspect, $M^2$ can be a lanthanide. In yet another aspect, for example, $M^2$ can be Sc, Y, La, Ti, Zr, Hf, V, Nb, Ta, Cr, Mo, W, Mn, Tc, Re, Fe, Ru, or Os. In still another aspect, $M^2$ can be Sc, Y, La, Ti, Zr, Hf, V, Cr, Fe, Ta, or Nb; alternatively, $M^2$ can be Sc; alternatively, $M^2$ can be Y; alternatively, $M^2$ can be La: alternatively, $M^2$ can be Ti; alternatively, $M^2$ can be Zr; alternatively, $M^2$ can be Hf; alternatively, $M^2$ can be V; alternatively, M can be Cr; alternatively, $M^2$ can be Fe; alternatively, $M^2$ can be Ta; or alternatively, $M^2$ can be Nb. In other aspects, $M^2$ can be Sc, Y, or La, or alternatively, $M^2$ can be Ti, Zr, Hf, or V.

In formula (II), $Ar^{2A}$ and $Ar^{2B}$ independently can be an arylene group. Often, $Ar^{2A}$ and $Ar^{2B}$ both can be phenylene groups (e.g., ortho-phenylene). In some aspects, $Ar^{2A}$ and $Ar^{2B}$ contain no substituents (other than -S and -D as indicated in formula (II)). The positioning of -S and -D about the arylene group can be ortho-substituted, meta-substituted, or para-substituted. In other aspects, additional substituents (other than -S and -D as indicated in formula (II)) can be present on the arylene group, and such substituents independently can be a hydrogen atom or a $C_1$ to $C_{18}$ hydrocarbyl or hydrocarbylsilyl group. A hydrogen atom substituent(s) is/are contemplated, therefore this invention comprises partially or completely saturated arylene groups. The $C_1$ to $C_{18}$ hydrocarbyl or hydrocarbylsilyl substituents, independently, can be any $C_1$ to $C_{18}$ hydrocarbyl or hydrocarbylsilyl group disclosed herein. For instance, suitable substituents on either arylene group independently can be hydrogen, methyl, ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, phenyl, tolyl, benzyl, naphthyl, trimethylsilyl, triisopropylsilyl, triphenylsilyl, or allyldimethylsilyl.

D in formula (II) can comprise a donor atom, and D can be O, S, $NR^{1C}$, $PR^{1D}$, or a substituted or unsubstituted, saturated or unsaturated, $C_4$ to $C_{18}$ heterocyclic group. In one aspect, D can be O. In another aspect, D can be S. In yet another aspect, D can be $NR^{1C}$ or $PR^{1D}$, wherein $R^{1C}$ and $R^{1D}$ independently can be hydrogen or a $C_1$ to $C_{18}$ hydrocarbyl group, such as any $C_1$ to $C_{18}$ hydrocarbyl group disclosed herein. It is contemplated that $R^{1C}$ and $R^{1D}$ independently can be hydrogen, methyl, ethyl, propyl, butyl, pentyl, hexyl, heptyl, octyl, nonyl, decyl, phenyl, or benzyl. In still another aspect, D in formula (II) can be a substituted or unsubstituted, saturated or unsaturated, $C_4$ to $C_{18}$ heterocyclic group, examples of which can include, but are not limited to, the following heterocyclic groups:

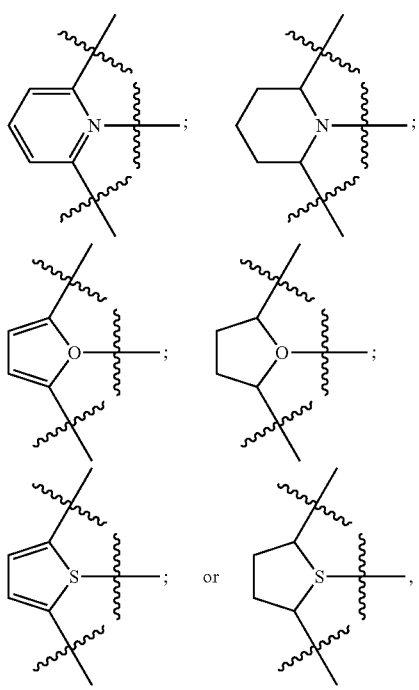

and the like. The heteroatom in the heterocyclic group is oriented towards the transition metal.

The selections of $X^0$, a, $X^1$, b, $X^2$, and c in formula (II) are the same as described above for formula (I). Therefore, in formula (II), each $X^0$ independently can be any neutral ligand disclosed herein (a can be 0, 1, or 2), each $X^1$ independently can be any monoanionic ligand disclosed herein (b can be 0, 1, 2, 3, or 4), and $X^2$ can be any dianionic ligand disclosed herein (c can be either 0 or 1). An oxidation state of the metal in formula (II), $M^2$, generally can be equal to (b+2c+2), as discussed above relative to formula (I).

In particular aspects contemplated herein, $M^2$ in formula (II) can be a Group 3 to Group 8 transition metal; or alternatively, $M^2$ can be Sc, Y, La, Ti, Zr, Hf, V, Cr, Fe, Ta, or Nb. In these aspects, $Ar^{2A}$ and $Ar^{2B}$ independently can be an arylene group (e.g., a phenylene group) with no substituents, or alternatively, $Ar^{2A}$ and $Ar^{2B}$ independently can be an arylene group with at least one substituent selected from a hydrogen atom or a $C_1$ to $C_{18}$ hydrocarbyl or hydrocarbylsilyl group (e.g., hydrogen, methyl, ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, phenyl, tolyl, benzyl, naphthyl, trimethylsilyl, triisopropylsilyl, triphenylsilyl, or allyldimethylsilyl). In these aspects, D can comprise an O atom, a S atom, a N atom, or a P atom; for instance, D can be O or D can be S. In these and other aspects, each $X^0$ independently can be a neutral ligand, such as an ether, a thioether, an amine, a nitrile, or a phosphine (a can be 0, 1, or 2); each $X^1$ independently can be a monoanionic ligand, such as hydrogen, a halide, or a $C_1$ to $C_{18}$ hydrocarbyl group, hydrocarbyloxide group, hydrocarbylamino group, hydrocarbylsilyl group, or hydrocarbylaminosilyl group (b can be 0, 1, 2, 3, or 4); and $X^2$ can be a dianionic ligand, such as =O, =$NR^{2A}$, or =$CR^{2B}R^{2C}$, wherein $R^{2A}$, $R^{2B}$, and $R^{2C}$ independently can be hydrogen or a $C_1$ to $C_{18}$ hydrocarbyl group (c can be either 0 or 1).

Other aspects disclosed herein are directed to transition metal compounds having the formula:

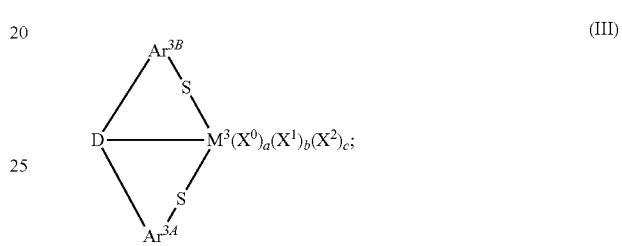

(III)

Generally, the selections of $M^3$, $Ar^{3A}$, $Ar^{3B}$, D, $X^0$, a, $X^1$, b, $X^2$, and c in formula (III) are independently described herein, and these selections may be combined in any combination to further describe the compound having formula (III).

In formula (III), the metal, $M^3$, can be any transition metal disclosed herein, while $Ar^{3A}$ and $Ar^{3B}$ independently can be any substituted or unsubstituted arylene group disclosed herein. For instance, $Ar^{3A}$ and $Ar^{3B}$ can be the same as the $A^{2A}$ and $Ar^{2B}$ groups in formula (II).

D in formula (III) can comprise any donor atom disclosed herein (e.g., O, S, N, P); D can be O, S, $NR^{1C}$, $PR^{1D}$, or a substituted or unsubstituted, saturated or unsaturated, $C_4$ to $C_{18}$ heterocyclic group. Therefore, D in formula (III) can be O, or D can be S, or D) can be $NR^{1C}$ or $PR^{1D}$, wherein $R^{1C}$ and $R^{1D}$ independently can be hydrogen or a $C_1$ to $C_{18}$ hydrocarbyl group, such as any $C_1$ to $C_{18}$ hydrocarbyl group disclosed herein. Additionally, D can be a heterocyclic group having one of the following structures:

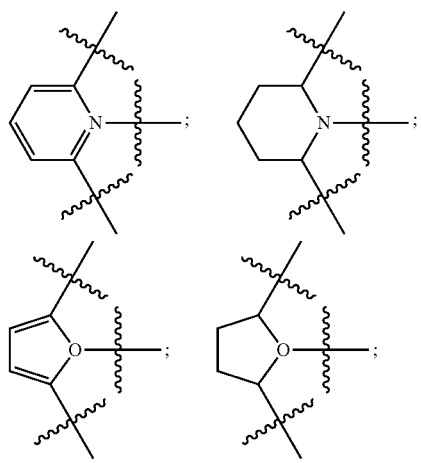

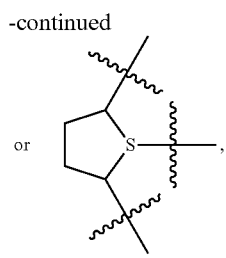

and the like.

The selections of $X^0$, a, $X^1$, b, $X^2$, and c in formula (II) are the same as described above for formulas (I) and (II). Accordingly, in formula (III), each $X^0$ independently can be any neutral ligand disclosed herein (a can be 0, 1, or 2), each $X^1$ independently can be any monoanionic ligand disclosed herein (b can be 0, 1, 2, 3, or 4), and $X^2$ can be any dianionic ligand disclosed herein (c can be either 0 or 1). An oxidation state of the metal in formula (III), $M^3$, generally can be equal to (b+2c+2), as discussed above relative to formula (I).

Methods of making transition metal complexes of the present invention also are provided. Examples 1-2 that follow provide a representative synthesis of a ligand with a central donor atom (O and N, respectively, but could be S or P) capped by two aryl thiolates. Examples 1-2 also illustrate ligand compounds having a trimethylsilyl or allyldimethylsilyl substituent on each arylene/phenylene group. Using an analogous synthesis scheme to that provided in Examples 1-2, other substituents (e.g., hydrocarbyl, alkyl, alkenyl, aryl, aralkyl, hydrocarbylsilyl, etc.) on an arylene/phenylene group can be derived.

Examples 3-18 demonstrate methods of producing transition metal complexes having formula (I), (II), and/or (III), from a ligand with a central donor atom capped by two aryl thiolates.

Activator-Support

The present invention encompasses various catalyst compositions containing an activator, which can be an activator-support. In one aspect, the activator-support can comprise a chemically-treated solid oxide. Alternatively, the activator-support can comprise a clay mineral, a pillared clay, an exfoliated clay, an exfoliated clay gelled into another oxide matrix, a layered silicate mineral, a non-layered silicate mineral, a layered aluminosilicate mineral, a non-layered aluminosilicate mineral, or combinations thereof.

Generally, chemically-treated solid oxides exhibit enhanced acidity as compared to the corresponding untreated solid oxide compound. The chemically-treated solid oxide also can function as a catalyst activator as compared to the corresponding untreated solid oxide. While the chemically-treated solid oxide can activate a transition metal complex having a thiolate ligand in the absence of co-catalysts, it is not necessary to eliminate co-catalysts from the catalyst composition. The activation function of the activator-support may be evident in the enhanced activity of catalyst composition as a whole, as compared to a catalyst composition containing the corresponding untreated solid oxide. However, it is believed that the chemically-treated solid oxide can function as an activator, even in the absence of an organoaluminum compound, aluminoxanes, organoboron or organoborate compounds, ionizing ionic compounds, and the like.

The chemically-treated solid oxide can comprise a solid oxide treated with an electron-withdrawing anion. While not intending to be bound by the following statement, it is believed that treatment of the solid oxide with an electron-withdrawing component augments or enhances the acidity of the oxide. Thus, either the activator-support exhibits Lewis or Brønsted acidity that is typically greater than the Lewis or Brønsted acid strength of the untreated solid oxide, or the activator-support has a greater number of acid sites than the untreated solid oxide, or both, One method to quantify the acidity of the chemically-treated and untreated solid oxide materials can be by comparing the polymerization activities of the treated and untreated oxides under acid catalyzed reactions.

Chemically-treated solid oxides of this invention generally can be formed from an inorganic solid oxide that exhibits Lewis acidic or Brønsted acidic behavior and has a relatively high porosity. The solid oxide can be chemically-treated with an electron-withdrawing component, typically an electron-withdrawing anion, to form an activator-support.

According to one aspect of the present invention, the solid oxide used to prepare the chemically-treated solid oxide can have a pore volume greater than about 0.1 cc/g. According to another aspect of the present invention, the solid oxide can have a pore volume greater than about 0.5 cc/g. According to yet another aspect of the present invention, the solid oxide can have a pore volume greater than about 1.0 cc/g.

In another aspect, the solid oxide can have a surface area of from about 100 to about 1000 m$^2$/g. In yet another aspect, the solid oxide can have a surface area of from about 200 to about 800 m$^2$/g. In still another aspect of the present invention, the solid oxide can have a surface area of from about 250 to about 600 m$^2$/g.

The chemically-treated solid oxide can comprise a solid inorganic oxide comprising oxygen and one or more elements selected from Group 2, 3, 4, 5, 6, 7, 8, 9, 10, 11, 12, 13, 14, or 15 of the periodic table, or comprising oxygen and one or more elements selected from the lanthanide or actinide elements (See: Hawley's Condensed Chemical Dictionary, 11$^{th}$ Ed., John Wiley & Sons, 1995; Cotton, F. A., Wilkinson, G., Murillo, C. A., and Bochmann, M., Advanced Inorganic Chemistry, 6$^{th}$ Ed., Wiley-Interscience, 1999). For example, the inorganic oxide can comprise oxygen and an element, or elements, selected from Al, B, Be, Bi, Cd, Co, Cr, Cu, Fe, Ga, La, Mn, Mo, Ni, Sb, Si, Sn, Sr, Th, Ti, V, W, P, Y, Zn, and Zr.

Suitable examples of solid oxide materials or compounds that can be used to form the chemically-treated solid oxide can include, but are not limited to, $Al_2O_3$, $B_2O_3$, BeO, $Bi_2O_3$, CdO, $Co_3O_4$, $Cr_2O_3$, CuO, $Fe_2O_3$, $Ga_2O_3$, $La_2O_3$, $Mn_2O_3$, $MoO_3$, NiO, $P_2O_5$, $Sb_2O_5$, $SiO_2$, $SnO_2$, SrO, $ThO_2$, $TiO_2$, $V_2O_5$, $WO_3$, $Y_2O_3$, ZnO, $ZrO_2$, and the like, including mixed oxides thereof, and combinations thereof. For example, the solid oxide can comprise silica, alumina, silica-alumina, silica-coated alumina, aluminum phosphate, aluminophosphate, heteropolytungstate, titania, zirconia, magnesia, boria, zinc oxide, mixed oxides thereof, or any combination thereof.

The solid oxide of this invention encompasses oxide materials such as alumina, "mixed oxide" compounds thereof such as silica-alumina, and combinations and mixtures thereof. The mixed oxide compounds such as silica-alumina can be single or multiple chemical phases with more than one metal combined with oxygen to form a solid oxide compound. Examples of mixed oxides that can be used in the activator-support of the present invention, either singly or in combination, can include, but are not limited to, silica-alumina, silica-titania, silica-zirconia, zeolites, various clay minerals, alumina-titania, alumina-zirconia, zinc-aluminate, alumina-boria, silica-boria, aluminophosphate-silica, titania-zirconia, and the like. The solid oxide of this invention also encompasses oxide materials such as silica-coated alumina, as described in U.S. Patent Publication No. 2010-0076167, the disclosure of which is incorporated herein by reference in its entirety.

The electron-withdrawing component used to treat the solid oxide can be any component that increases the Lewis or Brønsted acidity of the solid oxide upon treatment (as compared to the solid oxide that is not treated with at least one electron-withdrawing anion). According to one aspect of the present invention, the electron-withdrawing component can be an electron-withdrawing anion derived from a salt, an acid, or other compound, such as a volatile organic compound, that serves as a source or precursor for that anion. Examples of electron-withdrawing anions can include, but are not limited to, sulfate, bisulfate, fluoride, chloride, bromide, iodide, fluorosulfate, fluoroborate, phosphate, fluorophosphate, trifluoroacetate, triflate, fluorozirconate, fluorotitanate, phosphotungstate, and the like, including mixtures and combinations thereof. In addition, other ionic or non-ionic compounds that serve as sources for these electron-withdrawing anions also can be employed in the present invention. It is contemplated that the electron-withdrawing anion can be, or can comprise, fluoride, chloride, bromide, phosphate, triflate, bisulfate, or sulfate, and the like, or any combination thereof, in some aspects of this invention. In other aspects, the electron-withdrawing anion can comprise sulfate, bisulfate, fluoride, chloride, bromide, iodide, fluorosulfate, fluoroborate, phosphate, fluorophosphate, trifluoroacetate, triflate, fluorozirconate, fluorotitanate, and the like, or combinations thereof.

Thus, for example, the activator-support (e.g., chemically-treated solid oxide) used in the catalyst compositions of the present invention can be, or can comprise, fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, sulfated silica-coated alumina, phosphated silica-coated alumina, and the like, or combinations thereof. In one aspect, the activator-support can be, or can comprise, fluorided alumina, sulfated alumina, fluorided silica-alumina, sulfated silica-alumina, fluorided silica-coated alumina, sulfated silica-coated alumina, phosphated silica-coated alumina, and the like, or any combination thereof in another aspect, the activator-support can comprise fluorided alumina; alternatively, chlorided alumina; alternatively, sulfated alumina; alternatively, fluorided silica-alumina; alternatively, sulfated silica-alumina; alternatively, fluorided silica-zirconia; alternatively, chlorided silica-zirconia; or alternatively, fluorided silica-coated alumina.

When the electron-withdrawing component comprises a salt of an electron-withdrawing anion, the counterion or cation of that salt can be selected from any cation that allows the salt to revert or decompose back to the acid during calcining. Factors that dictate the suitability of the particular salt to serve as a source for the electron-withdrawing anion can include, but are not limited to, the solubility of the salt in the desired solvent, the lack of adverse reactivity of the cation, ion-pairing effects between the cation and anion, hygroscopic properties imparted to the salt by the cation, and the like, and thermal stability of the anion. Examples of suitable cations in the salt of the electron-withdrawing anion can include, but are not limited to, ammonium, trialkyl ammonium, tetraalkyl ammonium, tetraalkyl phosphonium, $H^+$, $[H(OEt)_2)_2]^+$, and the like.

Further, combinations of one or more different electron-withdrawing anions, in varying proportions, can be used to tailor the specific acidity of the activator-support to the desired level. Combinations of electron-withdrawing components can be contacted with the oxide material simultaneously or individually, and in any order that affords the desired chemically-treated solid oxide acidity. For example, one aspect of this invention can employ two or more electron-withdrawing anion source compounds in two or more separate contacting steps.

Thus, a process by which a chemically-treated solid oxide can be prepared is as follows: a selected solid oxide, or combination of solid oxides, can be contacted with a first electron-withdrawing anion source compound to form a first mixture; this first mixture can be calcined and then contacted with a second electron-withdrawing anion source compound to form a second mixture; the second mixture then can be calcined to form a treated solid oxide. In such a process, the first and second electron-withdrawing anion source compounds can be either the same or different compounds.

According to another aspect of the present invention, the chemically-treated solid oxide can comprise a solid inorganic oxide material, a mixed oxide material, or a combination of inorganic oxide materials, that is chemically-treated with an electron-withdrawing component, and optionally treated with a metal source, including metal salts, metal ions, or other metal-containing compounds. Non-limiting examples of the metal or metal ion can include zinc, nickel, vanadium, titanium, silver, copper, gallium, tin, tungsten, molybdenum, zirconium, and the like, or combinations thereof. Examples of chemically-treated solid oxides that contain a metal or metal ion can include, but are not limited to, chlorided zinc-impregnated alumina, fluorided titanium-impregnated alumina, fluorided zinc-impregnated alumina, chlorided zinc-impregnated silica-alumina, fluorided zinc-impregnated silica-alumina, sulfated zinc-impregnated alumina, chlorided zinc aluminate, fluorided zinc aluminate, sulfated zinc aluminate, silica-coated alumina treated with hexafluorotitanic acid, silica-coated alumina treated with zinc and then fluorided, and the like, or any combination thereof.

Any method of impregnating the solid oxide material with a metal can be used. The method by which the oxide is contacted with a metal source, typically a salt or metal-containing compound, can include, but is not limited to, gelling, co-gelling, impregnation of one compound onto another, and the like. If desired, the metal-containing compound can be added to or impregnated into the solid oxide in solution form, and subsequently converted into the supported metal upon calcining. Accordingly, the solid inorganic oxide can further comprise a metal selected from zinc, titanium, nickel, vanadium, silver, copper, gallium, tin, tungsten, molybdenum, and the like, or combinations of these metals. For example, zinc often can be used to impregnate the solid oxide because it can provide improved catalyst activity at a low cost.

The solid oxide can be treated with metal salts or metal-containing compounds before, after, or at the same time that the solid oxide is treated with the electron-withdrawing anion. Following any contacting method, the contacted mixture of solid compound, electron-withdrawing anion, and the metal ion can be calcined. Alternatively, a solid oxide material, an electron-withdrawing anion source, and the metal salt or metal-containing compound can be contacted and calcined simultaneously.

Various processes can be used to form the chemically-treated solid oxide useful in the present invention. The chemically-treated solid oxide can comprise the contact product of one or more solid oxides with one or more electron-withdrawing anion sources. It is not required that the solid oxide be calcined prior to contacting the electron-withdrawing anion source. Typically, the contact product can be calcined either during or after the solid oxide is contacted with the electron-withdrawing anion source. The solid oxide can be calcined or uncalcined. Various processes to prepare solid oxide activator-supports that can be employed in this invention have been reported. For example, such methods are described in U.S. Pat. Nos. 6,107,230, 6,165,929, 6,294,494, 6,300,271, 6,316,553, 6,355,594, 6,376,415, 6,388,017, 6,391,816, 6,395,666, 6,524,987, 6,548,441, 6,548,442, 6,576,583, 6,613,712, 6,632,894, 6,667,274, and 6,750,302, the disclosures of which are incorporated herein by reference in their entirety.

According to one aspect of the present invention, the solid oxide material can be chemically-treated by contacting it with an electron-withdrawing component, typically an electron-withdrawing anion source. Further, the solid oxide material optionally can be chemically treated with a metal ion, and then calcined to form a metal-containing or metal-impregnated chemically-treated solid oxide. According to another aspect of the present invention, the solid oxide material and electron-withdrawing anion source can be contacted and calcined simultaneously.

The method by which the oxide is contacted with the electron-withdrawing component, typically a salt or an acid of an electron-withdrawing anion, can include, but is not limited to, gelling, co-gelling, impregnation of one compound onto another, and the like. Thus, following any contacting method, the contacted mixture of the solid oxide, electron-withdrawing anion, and optional metal ion, can be calcined.

The solid oxide activator-support (i.e., chemically-treated solid oxide) thus can be produced by a process comprising:

1) contacting a solid oxide (or solid oxides) with an electron-withdrawing anion source compound (or compounds) to form a first mixture; and 2) calcining the first mixture to form the solid oxide activator-support.

According to another aspect of the present invention, the solid oxide activator-support (chemically-treated solid oxide) can be produced by a process comprising:

1) contacting a solid oxide (or solid oxides) with a first electron-withdrawing anion source compound to form a first mixture;

2) calcining the first mixture to produce a calcined first mixture;

3) contacting the calcined first mixture with a second electron-withdrawing anion source compound to form a second mixture; and 4) calcining the second mixture to form the solid oxide activator-support.

According to yet another aspect of the present invention, the chemically-treated solid oxide can be produced or formed by contacting the solid oxide with the electron-withdrawing anion source compound, where the solid oxide compound is calcined before, during, or after contacting the electron-withdrawing anion source, and where there is a substantial absence of aluminoxanes, organoboron or organoborate compounds, and ionizing ionic compounds.

Calcining of the treated solid oxide generally can be conducted in an ambient atmosphere, typically in a dry ambient atmosphere, at a temperature from about 200° C. to about 900° C., and for a time of about 1 minute to about 100 hours. Calcining can be conducted at a temperature of from about 300° C. to about 800° C., or alternatively, at a temperature of from about 400° C. to about 700° C. Calcining can be conducted for about 30 minutes to about 50 hours, or for about 1 hour to about 15 hours. Thus, for example, calcining can be carried out for about 1 to about 10 hours at a temperature of from about 350° C. to about 550° C. Any suitable ambient atmosphere can be employed during calcining. Generally, calcining can be conducted in an oxidizing atmosphere, such as air. Alternatively, an inert atmosphere, such as nitrogen or argon, or a reducing atmosphere, such as hydrogen or carbon monoxide, can be used.

According to one aspect of the present invention, the solid oxide material can be treated with a source of halide ion, sulfate ion, or a combination of anions, optionally treated with a metal ion, and then calcined to provide the chemically-treated solid oxide in the form of a particulate solid. For example, the solid oxide material can be treated with a source of sulfate (termed a "sulfating agent"), a source of chloride ion (termed a "chloriding agent"), a source of fluoride ion (termed a "fluoriding agent"), or a combination thereof, and calcined to provide the solid oxide activator. Useful acidic activator-supports can include, but are not limited to, bromided alumina, chlorided alumina, fluorided alumina, sulfated alumina, bromnided silica-alumnina, chlorided silica-alumina, fluorided silica-alumina, sulfated silica-alumina, bromided silica-zirconia, chlorided silica-zirconia, fluorided silica-zirconia, sulfated silica-zirconia, fluorided silica-titania, alumina treated with hexafluorotitanic acid, silica-coated alumina treated with hexafluorotitanic acid, silica-alumina treated with hexafluorozirconic acid, silica-alumina treated with trifluoroacetic acid, fluorided boria-alumina, silica treated with tetrafluoroboric acid, alumina treated with tetrafluoroboric acid, alumina treated with hexafluorophosphoric acid, a pillared clay, such as a pillared montmorillonite, optionally treated with fluoride, chloride, or sulfate; phosphated alumina or other aluminophosphates optionally treated with sulfate, fluoride, or chloride; or any combination of the above. Further, any of these activator-supports optionally can be treated or impregnated with a metal ion.

The chemically-treated solid oxide can comprise a fluorided solid oxide in the form of a particulate solid. The fluorided solid oxide can be formed by contacting a solid oxide with a fluoriding agent. The fluoride ion can be added to the oxide by forming a slurry of the oxide in a suitable solvent such as alcohol or water including, but not limited to, the one to three carbon alcohols because of their volatility and low surface tension, Examples of suitable fluoriding agents can include, but are not limited to, hydrofluoric acid (HF), ammonium fluoride ($NH_4F$), ammonium bifluoride ($NH_4HF_2$), ammonium tetrafluoroborate ($NH_4BF_4$), ammonium silicofluoride (hexafluorosilicate) (($NH_4)_2SiF_6$), ammonium hexafluorophosphate ($NH_4PF_6$), hexafluorotitanic acid ($H_2TiF_6$), ammonium hexafluorotitanic acid (($NH_4)_2TiF_6$), hexafluorozirconic acid ($H_2ZrF_6$), $AlF_3$, $NH_4AlF_4$, analogs thereof, and combinations thereof. Triflic acid and ammonium triflate also can be employed. For example, ammonium bifluoride ($NH_4HF_2$) can be used as the fluoriding agent, due to its ease of use and availability.

If desired, the solid oxide can be treated with a fluoriding agent during the calcining step. Any fluoriding agent capable of thoroughly contacting the solid oxide during the calcining step can be used. For example, in addition to those fluoriding agents described previously, volatile organic fluoriding agents can be used. Examples of volatile organic fluoriding agents useful in this aspect of the invention can include, but are not limited to, freons, perfluorohexane, perfluorobenzene, fluoromethane, trifluoroethanol, and the like, and combinations thereof. Calcining temperatures generally must be high enough to decompose the compound and release fluoride. Gaseous hydrogen fluoride (HF) or fluorine ($F_2$) itself also can be used with the solid oxide if fluorided while calcining. Silicon tetrafluoride ($SiF_4$) and compounds containing tetrafluoroborate ($BF_4^-$) also can be employed. One convenient method of contacting the solid oxide with the fluoriding agent can be to vaporize a fluoriding agent into a gas stream used to fluidize the solid oxide during calcination.

Similarly, in another aspect of this invention, the chemically-treated solid oxide can comprise a chlorided solid oxide in the form of a particulate solid. The chlorided solid oxide can be formed by contacting a solid oxide with a chloriding agent. The chloride ion can be added to the oxide by forming a slurry of the oxide in a suitable solvent. The solid oxide can be treated with a chloriding agent during the calcining step. Any chloriding agent capable of serving as a source of chloride and thoroughly contacting the oxide during the calcining step can be used, such as $SiCl_4$, $SiMe_2Cl_2$, $TiCl_4$, $BCl_3$, and the like, including mixtures thereof. Volatile organic chloriding agents can be used. Examples of suitable volatile organic chloriding agents can include, but are not limited to, certain freons, perchlorobenzene, chloromethane, dichloromethane, chloroform, carbon tetrachloride, trichloroethanol, and the like, or any combination thereof. Gaseous hydrogen chloride or chlorine itself also can be used with the solid oxide during calcination. One convenient method of contacting the oxide with the chloriding agent can be to vaporize a chloriding agent into a gas stream used to fluidize the solid oxide during calcination.

The amount of fluoride or chloride ion present before calcining the solid oxide generally can be from about 1 to about 50% by weight, where the weight percent is based on the weight of the solid oxide, for example, silica-alumina, before calcining, According to another aspect of this invention, the amount of fluoride or chloride ion present before calcining the solid oxide can be from about 1 to about 25% by weight, and according to another aspect of this invention, from about 2 to about 20% by weight. According to yet another aspect of this invention, the amount of fluoride or chloride ion present before calcining the solid oxide can be from about 4 to about 10% by weight. Once impregnated with halide, the halided oxide can be dried by any suitable method including, but not limited to, suction filtration followed by evaporation, drying under vacuum, spray drying, and the like, although it is also possible to initiate the calcining step immediately without drying the impregnated solid oxide.

The silica-alumina used to prepare the treated silica-alumina typically can have a pore volume greater than about 0.5 cc/g. According to one aspect of the present invention, the pore volume can be greater than about 0.8 cc/g, and according to another aspect of the present invention, greater than about 1.0 cc/g. Further, the silica-alumina generally can have a surface area greater than about 100 $m^2/g$. According to another aspect of this invention, the surface area can be greater than about 250 $m^2/g$. Yet, in another aspect, the surface area can be greater than about 350 $m^2/g$.

The silica-alumina utilized in the present invention typically can have an alumina content from about 5 to about 95% by weight. According to one aspect of this invention, the alumina content of the silica-alumina can be from about 5 to about 50%, or from about 8% to about 30%, alumina by weight. In another aspect, high alumina content silica-alumina compounds can be employed, in which the alumina content of these silica-alumina compounds typically ranges from about 60% to about 90%, or from about 65% to about 80%, alumina by weight. According to yet another aspect of this invention, the solid oxide component can comprise alumina without silica, and according to another aspect of this invention, the solid oxide component can comprise silica without alumina.

The sulfated solid oxide can comprise sulfate and a solid oxide component, such as alumina or silica-alumina, in the form of a particulate solid. Optionally, the sulfated oxide can be treated further with a metal ion such that the calcined sulfated oxide comprises a metal. According to one aspect of the present invention, the sulfated solid oxide can comprise sulfate and alumina. In some instances, the sulfated alumina can be formed by a process wherein the alumina is treated with a sulfate source, for example, sulfuric acid or a sulfate salt such as ammonium sulfate. This process generally can be performed by forming a slurry of the alumina in a suitable solvent, such as alcohol or water, in which the desired concentration of the sulfating agent has been added. Suitable organic solvents can include, but are not limited to, the one to three carbon alcohols because of their volatility and low surface tension.

According to one aspect of this invention, the amount of sulfate ion present before calcining can be from about 0.5 to about 100 parts by weight sulfate ion to about 100 parts by weight solid oxide. According to another aspect of this invention, the amount of sulfate ion present before calcining can be from about 1 to about 50 parts by weight sulfate ion to about 100 parts by weight solid oxide, and according to still another aspect of this invention, from about 5 to about 30 parts by weight sulfate ion to about 100 parts by weight solid oxide. These weight ratios are based on the weight of the solid oxide before calcining. Once impregnated with sulfate, the sulfated oxide can be dried by any suitable method including, but not limited to, suction filtration followed by evaporation, drying under vacuum, spray drying, and the like, although it is also possible to initiate the calcining step immediately.

According to another aspect of the present invention, the activator-support used in preparing the catalyst compositions of this invention can comprise an ion-exchangeable activator-support including, but not limited to, silicate and aluminosilicate compounds or minerals, either with layered or non-layered structures, and combinations thereof. In another aspect of this invention, ion-exchangeable, layered aluminosilicates such as pillared clays can be used as activator-supports. When the acidic activator-support comprises an ion-exchangeable activator-support, it can optionally be treated with at least one electron-withdrawing anion such as those disclosed herein, though typically the ion-exchangeable activator-support is not treated with an electron-withdrawing anion.

According to another aspect of the present invention, the activator-support of this invention can comprise clay minerals having exchangeable cations and layers capable of expanding. Typical clay mineral activator-supports can include, but are not limited to, ion-exchangeable, layered aluminosilicates such as pillared clays. Although the term "support" is used, it is not meant to be construed as an inert component of the catalyst composition, but rather can be considered an active part of the catalyst composition, because of its intimate association with the transition metal complex component.

According to another aspect of the present invention, the clay materials of this invention can encompass materials either in their natural state or that have been treated with various ions by wetting, ion exchange, or pillaring. Typically, the clay material activator-support of this invention can comprise clays that have been ion exchanged with large cations, including polynuclear, highly charged metal complex cations. However, the clay material activator-supports of this invention also can encompass clays that have been ion exchanged with simple salts, including, but not limited to, salts of Al(III), Fe(II), Fe(II), and Zn(II) with ligands such as halide, acetate, sulfate, nitrate, or nitrite.

According to another aspect of the present invention, the activator-support can comprise a pillared clay. The term "pillared clay" is used to refer to clay materials that have been ion exchanged with large, typically polynuclear, highly charged metal complex cations. Examples of such ions can include, but are not limited to, Keggin ions which can have charges such as 7+, various polyoxometallates, and other large ions. Thus, the term pillaring can refer to a simple exchange reaction in which the exchangeable cations of a clay material are replaced with large, highly charged ions, such as Keggin ions. These polymeric cations then can be immobilized within the interlayers of the clay and when calcined are converted to metal oxide "pillars," effectively supporting the clay layers as column-like structures. Thus, once the clay is dried and calcined to produce the supporting pillars between clay layers, the expanded lattice structure can be maintained and the porosity can be enhanced. The resulting pores can vary in shape and size as a function of the pillaring material and the parent clay material used. Examples of pillaring and pillared clays are found in: T. J. Pinnavaia, *Science* 220 (4595), 365-371 (1983); J. M. Thomas, Intercalation Chemistry, (S. Whittington and A. Jacobson, eds.) Ch. 3, pp. 55-99, Academic Press, Inc., (1972); U.S. Pat. No. 4,452,910; U.S. Pat. No. 5,376,611; and U.S. Pat. No. 4,060,480; the disclosures of which are incorporated herein by reference in their entirety.

The pillaring process can utilize clay minerals having exchangeable cations and layers capable of expanding. Any pillared clay that can enhance the polymerization of olefins in the catalyst composition of the present invention can be used. Therefore, suitable clay minerals for pillaring can include, but are not limited to, allophanes; smectites, both dioctahedral (Al) and tri-octahedral (Mg) and derivatives thereof such as montmorillonites (bentonites), nontronites, hectorites, or laponites; halloysites; vermiculites; micas; fluoromicas; chlorites; mixed-layer clays; the fibrous clays including but not limited to sepiolites, attapulgites, and palygorskites; a serpentine clay; illite; laponite; saponite; and any combination thereof. In one aspect, the pillared clay activator-support can comprise bentonite or montmorillonite. The principal component of bentonite is montmorillonite.

The pillared clay can be pretreated if desired. For example, a pillared bentonite can be pretreated by drying at about 300° C. under an inert atmosphere, typically dry nitrogen, for about 3 hours, before being added to the polymerization reactor. Although an exemplary pretreatment is described herein, it should be understood that the preheating can be carried out at many other temperatures and times, including any combination of temperature and time steps, all of which are encompassed by this invention.

The activator-support used to prepare the catalyst compositions of the present invention can be combined with other inorganic support materials, including, but not limited to, zeolites, inorganic oxides, phosphated inorganic oxides, and the like. In one aspect, typical support materials that can be used include, but are not limited to, silica, silica-alumina, alumina, titania, zirconia, magnesia, boria, thoria, aluminophosphate, aluminum phosphate, silica-titania, coprecipitated silica/titania, mixtures thereof, or any combination thereof.

According to another aspect of the present invention, one or more of the transition metal complexes having a thiolate ligand can be precontacted with an olefin monomer and an organoaluminum compound for a first period of time prior to contacting this mixture with the activator-support. Once the precontacted mixture of the transition metal complex(es), olefin monomer, and organoaluminum compound is contacted with the activator-support, the composition further comprising the activator-support is termed a "postcontacted" mixture. The postcontacted mixture can be allowed to remain in further contact for a second period of time prior to being charged into the reactor in which the polymerization process will be carried out.

According to yet another aspect of the present invention, one or more of the transition metal complexes having a thiolate ligand can be precontacted with an olefin monomer and an activator-support for a first period of time prior to contacting this mixture with the organoaluminum compound. Once the precontacted mixture of the transition metal complex(es), olefin monomer, and activator-support is contacted with the organoaluminum compound, the composition further comprising the organoaluminum is termed a "postcontacted" mixture. The postcontacted mixture can be allowed to remain in further contact for a second period of time prior to being introduced into the polymerization reactor.

Organoaluminum Compounds

In some aspects, catalyst compositions of the present invention can comprise one or more organoaluminum compounds. Such compounds can include, but are not limited to, compounds having the formula:

$$(R^X)_3Al;$$

where $R^X$ can be an aliphatic group having from 1 to 10 carbon atoms. For example, $R^X$ can be methyl, ethyl, propyl, butyl, hexyl, or isobutyl.

Other organoaluminum compounds which can be used in catalyst compositions disclosed herein can include, but are not limited to, compounds having the formula:

$$Al(X^5)_m(X^6)_{3-m},$$

where $X^5$ can be a hydrocarbyl; $X^6$ can be an alkoxide or an aryloxide, a halide, or a hydride; and m can be from 1 to 3, inclusive. Hydrocarbyl is used herein to specify a hydrocarbon radical group and includes, for instance, aryl, alkyl, cycloalkyl, alkenyl, cycloalkenyl, cycloalkadienyl, alkynyl, aralkyl, aralkenyl, and aralkynyl groups.

In one aspect, $X^5$ can be a hydrocarbyl having from 1 to about 18 carbon atoms. In another aspect of the present invention, $X^5$ can be an alkyl having from 1 to 10 carbon atoms. For example, $X^5$ can be methyl, ethyl, propyl, n-butyl, sec-butyl, isobutyl, or hexyl, and the like, in yet another aspect of the present invention.

According to one aspect of the present invention, $X^6$ can be an alkoxide or an aryloxide, any one of which has from 1 to 18 carbon atoms, a halide, or a hydride. In another aspect of the present invention, $X^6$ can be selected independently from fluorine and chlorine. Yet, in another aspect, $X^6$ can be chlorine.

In the formula, $Al(X^5)_m(X^6)_{3-m}$, m can be a number from 1 to 3, inclusive, and typically, m can be 3. The value of m is not restricted to be an integer; therefore, this formula can include sesquihalide compounds or other organoaluminum cluster compounds.

Examples of organoaluminum compounds suitable for use in accordance with the present invention can include, but are not limited to, trialkylaluminum compounds, dialkylaluminum halide compounds, dialkylaluminum alkoxide compounds, dialkylaluminum hydride compounds, and combinations thereof. Specific non-limiting examples of suitable organoaluminum compounds can include trimethylaluminum (TMA), triethylaluminum (TEA), tri-n-propylaluminum (TNPA), tri-n-butylaluminum (TNBA), triisobutylaluminum (TIBA), tri-n-hexylaluminum, tri-n-octylaluminum, diisobutylaluminum hydride, diethylaluminum ethoxide, diethylaluminum chloride, and the like, or combinations thereof.

The present invention contemplates a method of precontacting a transition metal complex having a thiolate ligand with an organoaluminum compound and an olefin monomer to form a precontacted mixture, prior to contacting this precontacted mixture with an activator-support to form a catalyst composition. When the catalyst composition is prepared in this manner, typically, though not necessarily, a portion of the organoaluminum compound can be added to the precontacted mixture and another portion of the organoaluminum compound can be added to the postcontacted mixture prepared when the precontacted mixture is contacted with the solid oxide activator-support. However, the entire organoaluminum compound can be used to prepare the catalyst composition in either the precontacting or postcontacting step. Alternatively, all the catalyst components can be contacted in a single step.

Further, more than one organoaluminum compound can be used in either the precontacting or the postcontacting step. When an organoaluminum compound is added in multiple steps, the amounts of organoaluminum compound disclosed herein include the total amount of organoaluminum compound used in both the precontacted and postcontacted mixtures, and any additional organoaluminum compound added to the polymerization reactor. Therefore, total amounts of organoaluminum compounds are disclosed regardless of whether a single organoaluminum compound or more than one organoaluminum compound is used.

Aluminoxane Compounds

The present invention further provides a catalyst composition which can comprise an aluminoxane compound. As used herein, the term "aluminoxane" refers to aluminoxane compounds, compositions, mixtures, or discrete species, regardless of how such aluminoxanes are prepared, formed or otherwise provided. For example, a catalyst composition comprising an aluminoxane compound can be prepared in which aluminoxane is provided as the poly(hydrocarbyl aluminum oxide), or in which aluminoxane is provided as the combination of an aluminum alkyl compound and a source of active protons such as water. Aluminoxanes also can be referred to as poly(hydrocarbyl aluminum oxides) or organoaluminoxanes.

The other catalyst components typically can be contacted with the aluminoxane in a saturated hydrocarbon compound solvent, though any solvent that is substantially inert to the reactants, intermediates, and products of the activation step can be used. The catalyst composition formed in this manner can be collected by any suitable method, for example, by filtration. Alternatively, the catalyst composition can be introduced into the polymerization reactor without being isolated.

The aluminoxane compound of this invention can be an oligomeric aluminum compound comprising linear structures, cyclic structures, or cage structures, or mixtures of all three. Cyclic aluminoxane compounds having the formula:

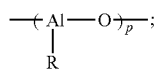

wherein R in this formula can be a linear or branched alkyl having from 1 to 10 carbon atoms, and p in this formula can be an integer from 3 to 20, are encompassed by this invention. The AlRO moiety shown here also can constitute the repeating unit in a linear aluminoxane. Thus, linear aluminoxanes having the formula:

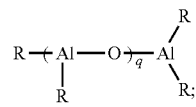

wherein R in this formula can be a linear or branched alkyl having from 1 to 10 carbon atoms, and q in this formula can be an integer from 1 to 50, are also encompassed by this invention.

Further, aluminoxanes can have cage structures of the formula $R^t_{5r+\alpha}R^b_{r-\alpha}Al_{4r}O_{3r}$, wherein $R^t$ can be a terminal linear or branched alkyl group having from 1 to 10 carbon atoms; $R^b$ can be a bridging linear or branched alkyl group having from 1 to 10 carbon atoms; r can be 3 or 4; and α can be equal to $n_{Al(3)}-n_{O(2)}+n_{O(4)}$, wherein $n_{Al(3)}$ is the number of three coordinate aluminum atoms, $n_{O(2)}$ is the number of two coordinate oxygen atoms, and $n_{O(4)}$ is the number of 4 coordinate oxygen atoms.

Thus, aluminoxanes which can be employed in the catalyst compositions of the present invention can be represented generally by formulas such as $(R\text{—}Al\text{—}O)_p$, $R(R\text{—}Al\text{—}O)_q AlR_2$, and the like. In these formulas, the R group typically can be a linear or branched $C_1$-$C_6$ alkyl, such as methyl, ethyl, propyl, butyl, pentyl, or hexyl. Examples of aluminoxane compounds that can be used in accordance with the present invention can include, but are not limited to, methylaluminoxane, ethylaluminoxane, n-propylaluminoxane, iso-propylaluminoxane, n-butylaluminoxane, t-butylaluminoxane, sec-butylaluminoxane, iso-butylaluminoxane, 1-pentylaluminoxane, 2-pentylaluminoxane, 3-pentylaluminoxane, iso-pentylaluminoxane, neopentylaluminoxane, and the like, or any combination thereof. Methylaluminoxane, ethylaluminoxane, and iso-butylaluminoxane can be prepared from trimethylaluminum, triethylaluminum, or triisobutylaluminum, respectively, and sometimes are referred to as poly(methyl aluminum oxide), poly(ethyl aluminum oxide), and poly (isobutyl aluminum oxide), respectively. It is also within the scope of the invention to use an aluminoxane in combination with a trialkylaluminum, such as that disclosed in U.S. Pat. No. 4,794,096, incorporated herein by reference in its entirety.

The present invention contemplates many values of p and q in the aluminoxane formulas $(R\text{—}Al\text{—}O)_p$ and $R(R\text{—}Al\text{—}O)_q AlR_2$, respectively. In some aspects, p and q can be at least 3. However, depending upon how the organoaluminoxane is prepared, stored, and used, the value of p and q can vary within a single sample of aluminoxane, and such combinations of organoaluminoxanes are contemplated herein.

In preparing a catalyst composition containing an aluminoxane, the molar ratio of the total moles of aluminum in the aluminoxane (or aluminoxanes) to the total moles of transition metal complex(es) in the composition generally can be between about 1:10 and about 100,000:1. In another aspect, the molar ratio can be in a range from about 5:1 to about 15,000:1. Optionally, aluminoxane can be added to a polymerization zone in ranges from about 0.01 mg/L to about 1000 mg/L, from about 0.1 mg/L to about 100 mg/L, or from about 1 mg/L to about 50 mg/L.

Organoaluminoxanes can be prepared by various procedures. Examples of organoaluminoxane preparations are disclosed in U.S. Pat. Nos. 3,242,099 and 4,808,561, the disclosures of which are incorporated herein by reference in their entirety. For example, water in an inert organic solvent can be reacted with an aluminum alkyl compound, such as $(R^X)_3Al$, to form the desired organoaluminoxane compound. While not intending to be bound by this statement, it is believed that this synthetic method can afford a mixture of both linear and cyclic R—Al—O aluminoxane species, both of which are encompassed by this invention. Alternatively, organoaluminoxanes can be prepared by reacting an aluminum alkyl compound, such as $(R^X)_3Al$, with a hydrated salt, such as hydrated copper sulfate, in an inert organic solvent.

Organoboron/Organoborate Compounds

According to another aspect of the present invention, the catalyst composition can comprise an organoboron or organoborate compound. Such compounds can include neutral boron compounds, borate salts, and the like, or combinations thereof. For example, fluoroorgano boron compounds and fluoroorgano borate compounds are contemplated.

Any fluoroorgano boron or fluoroorgano borate compound can be utilized with the present invention. Examples of fluoroorgano borate compounds that can be used in the present invention can include, but are not limited to, fluorinated aryl borates such as N,N-dimethylanilinium tetrakis(pentafluorophenyl)borate, triphenylcarbenium tetrakis(pentafluorophenyl)borate, lithium tetrakis(pentafluorophenyl)borate, N,N-dimethylanilinium tetrakis[3,5-bis(trifluoromethyl)phenyl]borate, triphenylcarbenium tetrakis[3,5-bis(trifluoromethyl)phenyl]borate, and the like, or mixtures thereof. Examples of fluoroorgano boron compounds that can be used as co-catalysts or activators in the present invention can include, but are not limited to, tris(pentafluorophenyl)boron, tris[3,5-bis(trifluoromethyl)phenyl]boron, and the like, or mixtures thereof. Although not intending to be bound by the following theory, these examples of fluoroorgano borate and fluoroorgano boron compounds, and related compounds, may form "weakly-coordinating" anions when combined with a transition metal complex having a thiolate ligand (see e.g., U.S. Pat. No. 5,919,983, the disclosure of which is incorporated herein by reference in its entirety). Applicants also contemplate the use of diboron, or bis-boron, compounds or other bifunctional compounds containing two or more boron atoms in the chemical structure, such as disclosed in J. Am. Chem. Soc., 2005, 127, pp. 14756-14768, the content of which is incorporated herein by reference in its entirety.

Generally, any amount of organoboron compound can be used. According to one aspect of this invention, the molar ratio of the total moles of organoboron or organoborate compound (or compounds) to the total moles of transition metal complex (or complexes) in the catalyst composition can be in a range from about 0.1:1 to about 15:1. Typically, the amount of the fluoroorgano boron or fluoroorgano borate compound used can be from about 0.5 moles to about 10 moles of boron/borate compound per mole of transition metal complex(es). According to another aspect of this invention, the amount of fluoroorgano boron or fluoroorgano borate compound can be from about 0.8 moles to about 5 moles of boron/borate compound per mole of transition metal complex(es).

Ionizing Ionic Compounds

The present invention further provides a catalyst composition which can comprise an ionizing ionic compound. An ionizing ionic compound is an ionic compound that can function as an activator or co-catalyst to enhance the activity of the catalyst composition. While not intending to be bound by theory, it is believed that the ionizing ionic compound may be capable of reacting with a transition metal complex having a thiolate ligand and converting the transition metal complex into one or more cationic transition metal complexes, or incipient cationic transition metal complexes. Again, while not intending to be bound by theory, it is believed that the ionizing ionic compound can function as an ionizing compound by completely or partially extracting an anionic ligand, such as $X^1$ or $X^2$, from the transition metal complex having a thiolate ligand. However, the ionizing ionic compound can be an activator or co-catalyst regardless of whether it is ionizes the transition metal complex, abstracts a $X^1$ or $X^2$ ligand in a fashion as to form an ion pair, weakens the metal-$X^1$ or metal-$X^2$ bond in the transition metal complex, simply coordinates to a $X^1$ or $X^2$ ligand, or activates the transition metal complex having a thiolate ligand by some other mechanism.

Further, it is not necessary that the ionizing ionic compound activate the transition metal complex only. The activation function of the ionizing ionic compound can be evident in the enhanced activity of catalyst composition as a whole, as compared to a catalyst composition that does not contain an ionizing ionic compound.

Examples of ionizing ionic compounds can include, but are not limited to, the following compounds: tri(n-butyl)ammonium tetrakis(p-tolyl)borate, tri(n-butyl) ammonium tetrakis(m-tolyl)borate, tri(n-butyl)ammonium tetrakis(2,4-dimethylphenyl)borate, tri(n-butyl)ammonium tetrakis(3,5-dimethylphenyl)borate, tri(n-butyl)ammonium tetrakis[3,5-bis(trifluoromethyl)phenyl]borate, tri(n-butyl)ammonium tetrakis(pentafluorophenyl)borate, N,N-dimethylanilinium tetrakis(p-tolyl)borate, N,N-dimethylanilinium tetrakis(m-tolyl)borate, N,N-dimethylanilinium tetrakis(2,4-dimethylphenyl)borate, N,N-dimethylanilinium tetrakis(3,5-dimethyl-phenyl)borate, N,N-dimethylanilinium tetrakis[3,5-bis(trifluoromethyl)phenyl]borate, N,N-dimethylanilinium tetrakis(pentafluorophenyl)borate, triphenylcarbenium tetrakis(p-tolyl)borate, triphenylcarbenium tetrakis(m-tolyl)borate, triphenylcarbenium tetrakis(2,4-dimethylphenyl)borate, triphenylcarbenium tetrakis(3,5-dimethylphenyl)borate, triphenylcarbenium tetrakis[3,5-bis(trifluoro-methyl)phenyl]borate, triphenylcarbenium tetrakis(pentafluorophenyl)borate, tropylium tetrakis(p-tolyl)borate, tropylium tetrakis(n-tolyl)borate, tropylium tetrakis(2,4-dimethylphenyl)borate, tropylium tetrakis(3,5-dimethylphenyl)borate, tropylium tetrakis[3,5-bis(trifluoromethyl)phenyl]borate, tropylium tetrakis(pentafluorophenyl)borate, lithium tetrakis(pentafluorophenyl)borate, lithium tetraphenylborate, lithium tetrakis(p-tolyl)borate, lithium tetrakis(m-tolyl)borate, lithium tetrakis(2,4-dimethylphenyl)borate, lithium tetrakis(3,5-dimethylphenyl)borate, lithium tetrafluoroborate, sodium tetrakis(pentafluorophenyl)borate, sodium tetraphenylborate, sodium tetrakis(p-tolyl)borate, sodium tetrakis(m-tolyl)borate, sodium tetrakis(2,4-dimethylphenyl)borate, sodium tetrakis(3,5-dimethylphenyl)borate, sodium tetrafluoroborate, potassium tetrakis(pentafluorophenyl)borate, potassium tetraphenylborate, potassium tetrakis(p-tolyl)borate, potassium tetrakis(m-tolyl)borate, potassium tetrakis(2,4-dimethylphenyl)borate, potassium tetrakis(3,5-dimethylphenyl)borate, potassium tetrafluoroborate, lithium tetrakis(pentafluorophenyl)aluminate, lithium tetraphenylaluminate, lithium tetrakis(p-tolyl)aluminate, lithium tetrakis(m-tolyl)aluminate, lithium tetrakis(2,4-dimethylphenyl)aluminate, lithium tetrakis(3,5-dimethylphenyl)aluminate, lithium tetrafluoroaluminate, sodium tetrakis(pentafluorophenyl)aluminate, sodium tetraphenylaluminate, sodium tetrakis(p-tolyl)aluminate, sodium tetrakis (m-tolyl)aluminate, sodium tetrakis(2,4-dimethylphenyl) aluminate, sodium tetrakis(3,5-dimethylphenyl)aluminate, sodium tetrafluoroaluminate, potassium tetrakis(pentafluorophenyl)aluminate, potassium tetraphenylaluminate, potassium tetrakis(p-tolyl)aluminate, potassium tetrakis(m-tolyl) aluminate, potassium tetrakis(2,4-dimethylphenyl) aluminate, potassium tetrakis(3,5-dimethylphenyl) aluminate, potassium tetrafluoroaluminate, and the like, or combinations thereof. Ionizing ionic compounds useful in this invention are not limited to these; other examples of ionizing ionic compounds are disclosed in U.S. Pat. Nos. 5,576,259 and 5,807,938, the disclosures of which are incorporated herein by reference in their entirety.

Olefin Monomers

Unsaturated reactants that can be employed with catalyst compositions and polymerization processes of this invention typically can include olefin compounds having from 2 to 30 carbon atoms per molecule and having at least one olefinic double bond. This invention encompasses homopolymerization processes using a single olefin such as ethylene or propylene, as well as copolymerization, terpolymerization, etc., reactions using an olefin monomer with at least one different olefinic compound. For example, the resultant ethylene copolymers, terpolymers, etc., generally can contain a major amount of ethylene (>50 mole percent) and a minor amount of comonomer (<50 mole percent), though this is not a requirement. Comonomers that can be copolymerized with ethylene often can have from 3 to 20 carbon atoms in their molecular chain.

Acyclic, cyclic, polycyclic, terminal ($\alpha$), internal, linear, branched, substituted, unsubstituted, functionalized, and non-functionalized olefins can be employed in this invention. For example, typical unsaturated compounds that can be polymerized with the catalyst compositions of this invention can include, but are not limited to, ethylene, propylene, 1-butene, 2-butene, 3-methyl-1-butene, isobutylene, 1-pentene, 2-pentene, 3-methyl-1-pentene, 4-methyl-1-pentene, 1-hexene, 2-hexene, 3-hexene, 3-ethyl-1-hexene, 1-heptene, 2-heptene, 3-heptene, the four normal octenes (e.g., 1-octene), the four normal nonenes, the five normal decenes, and the like, or mixtures of two or more of these compounds. Cyclic and bicyclic olefins, including but not limited to, cyclopentene, cyclohexene, norbornylene, norbornadiene, and the like, also can be polymerized as described above. Styrene can also be employed as a monomer in the present invention. In an aspect, the olefin monomer can be a $C_2$-$C_{10}$ olefin; alternatively, the olefin monomer can be ethylene; or alternatively, the olefin monomer can be propylene.

When a copolymer (or alternatively, a terpolymer) is desired, the olefin monomer can comprise, for example, ethylene or propylene, which is copolymerized with at least one comonomer. According to one aspect of this invention, the olefin monomer in the polymerization process can comprise ethylene. In this aspect, examples of suitable olefin comonomers an include, but are not limited to, propylene, 1-butene, 2-butene, 3-methyl-1-butene, isobutylene, 1-pentene, 2-pentene, 3-methyl-1-pentene, 4-methyl-1-pentene, 1-hexene, 2-hexene, 3-ethyl-1-hexene, 1-heptene, 2-heptene, 3-heptene, 1-octene, 1-decene, styrene, and the like, or combinations thereof. According to one aspect of the present invention, the comonomer can comprise 1-butene, 1-pentene, 1-hexene, 1-octene, 1-decene, styrene, or any combination thereof.

Generally, the amount of comonomer introduced into a reactor zone to produce a copolymer can be from about 0.01 to about 50 weight percent of the comonomer based on the total weight of the monomer and comonomer. According to another aspect of the present invention, the amount of comonomer introduced into a reactor zone can be from about 0.01 to about 40 weight percent comonomer based on the total weight of the monomer and comonomer. In still another aspect, the amount of comonomer introduced into a reactor zone can be from about 0.1 to about 35 weight percent comonomer based on the total weight of the monomer and comonomer. Yet, in another aspect, the amount of comonomer introduced into a reactor zone can be from about 0.5 to about 20 weight percent comonomer based on the total weight of the monomer and comonomer.

While not intending to be bound by this theory, where branched, substituted, or functionalized olefins are used as reactants, it is believed that a steric hindrance can impede and/or slow the polymerization process. Thus, branched and/or cyclic portion(s) of the olefin removed somewhat from the carbon-carbon double bond would not be expected to hinder the reaction in the way that the same olefin substituents situated more proximate to the carbon-carbon double bond might. According to one aspect of the present invention, at least one monomer/reactant can be ethylene, so the polymerizations are either a homopolymerization involving only ethylene, or copolymerizations with a different acyclic, cyclic, terminal, internal, linear, branched, substituted, or unsubstituted olefin. In addition, the catalyst compositions of this invention can be used in the polymerization of diolefin compounds including, but not limited to, 1,3-butadiene, isoprene, 1,4-pentadiene, and 1,5-hexadiene.

Catalyst Compositions

The present invention further includes various catalyst systems and compositions. A composition in accordance with an aspect of the invention can comprise a transition metal complex with a thiolate ligand. In another aspect, a catalyst composition can comprise a transition metal complex with a thiolate ligand and an organoaluminum compound. In some aspects, the present invention can employ catalyst compositions comprising a transition metal complex with a thiolate ligand and an activator, while in other aspects, the present invention can employ catalyst compositions comprising a transition metal complex with a thiolate ligand and an activator-support. These catalyst compositions can be utilized to produce polyolefins—homopolymers, copolymers, and the like—for a variety of end-use applications.

Transition metal complexes or compounds with a thiolate ligand having formulas (I), (II), and/or (III) were discussed above. In aspects of the present invention, it is contemplated that the catalyst composition can contain more than one transition metal compound having formula (I), (II), and/or (III). Further, additional transition metal compounds—other than those having formulas (I), (II), and/or (III)—as well as metallocene compounds, can be employed in the catalyst composition and/or the polymerization process, provided that the additional transition metal compound(s) and/or metallocene compound(s) does not detract from the advantages disclosed herein. Additionally, more than one activator and/or more than one activator-support also may be utilized.

Generally, catalyst compositions of the present invention can comprise a transition metal complex with a thiolate ligand having formula (I), (II), and/or (III) and an activator. In aspects of the invention, the activator can comprise an activator-support. Activator-supports useful in the present invention were disclosed above. Such catalyst compositions can further comprise one or more than one organoaluminum compound or compounds (suitable organoaluminum compounds also were discussed above). Thus, a catalyst composition of this invention can comprise a transition metal complex having formula (I), (II), and/or (III), an activator-support, and an organoaluminum compound. For instance, the activator-support can comprise (or consist essentially of, or consist of) fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, sulfated silica-coated alumina, phosphated silica-coated alumina, and the like, or combinations thereof. Additionally, the organoaluminum compound can comprise (or consist essentially of, or consist of) trimethylaluminum, triethylaluminum, tri-n-propylaluminum, tri-n-butylaluminum, triisobutylaluminum, tri-n-hexylaluminum, tri-n-octylaluminum, diisobutylaluminum hydride, diethylaluminum ethoxide, diethylaluminum chloride, and the like, or combinations thereof. Accordingly, a catalyst composition consistent with this invention can comprise (or consist essentially of, or consist of) a transition metal compound having formula (I), (II), and/or (III), sulfated alumina (or fluorided silica-alumina), and triethylaluminum (or triisobutylaluminum).

In another aspect of the present invention, a catalyst composition is provided which comprises a transition metal complex having formula (I), (II), and/or (III), an activator-support, and an organoaluminum compound, wherein this catalyst composition is substantially free of aluminoxanes, organoboron or organoborate compounds, ionizing ionic compounds, and/or other similar materials; alternatively, substantially free of aluminoxanes; alternatively, substantially free or organoboron or organoborate compounds; or alternatively, substantially free of ionizing ionic compounds. In these aspects, the catalyst composition has catalyst activity, to be discussed below, in the absence of these additional materials. For example, a catalyst composition of the present invention can consist essentially of a transition metal complex with a thiolate ligand having formula (I), (II), and/or (III), an activator-support, and an organoaluminum compound, wherein no other materials are present in the catalyst composition which would increase/decrease the activity of the catalyst composition by more than about 10% from the catalyst activity of the catalyst composition in the absence of said materials.

However, in other aspects of this invention, these activators/co-catalysts can be employed. For example, a catalyst composition comprising a transition metal complex having formula (I), (II), and/or (III), and an activator-support can further comprise an optional co-catalyst. Suitable co-catalysts in this aspect include, but are not limited to, aluminoxane compounds, organoboron or organoborate compounds, ionizing ionic compounds, and the like, or any combination thereof. More than one co-catalyst can be present in the catalyst composition.

In a different aspect, a catalyst composition is provided which does not require an activator-support. Such a catalyst composition can comprise a transition metal complex having formula (I), (II), and/or (III), and an activator, wherein the activator comprises an aluminoxane compound, an organoboron or organoborate compound, an ionizing ionic compound, or combinations thereof.

This invention further encompasses methods of making these catalyst compositions, such as, for example, contacting the respective catalyst components in any order or sequence.

The transition metal complex having formula (I), (II), and/ or (III) can be precontacted with an olefinic monomer if desired, not necessarily the olefin monomer to be polymerized, and an organoaluminum compound for a first period of time prior to contacting this precontacted mixture with an activator-support. The first period of time for contact, the precontact time, between the transition metal complex, the olefinic monomer, and the organoaluminum compound typically ranges from a time period of about 1 minute to about 24 hours, for example, from about 3 minutes to about 1 hour. Precontact times from about 10 minutes to about 30 minutes are also employed. Alternatively, the precontacting process is carried out in multiple steps, rather than a single step, in which multiple mixtures are prepared, each comprising a different set of catalyst components. For example, at least two catalyst components are contacted forming a first mixture, followed by contacting the first mixture with at least one other catalyst component forming a second mixture, and so forth.

Multiple precontacting steps can be carried out in a single vessel or in multiple vessels. Further, multiple precontacting steps can be carried out in series (sequentially), in parallel, or a combination thereof. For example, a first mixture of two catalyst components can be formed in a first vessel, a second mixture comprising the first mixture plus one additional catalyst component can be formed in the first vessel or in a second vessel, which is typically placed downstream of the first vessel.

In another aspect, one or more of the catalyst components can be split and used in different precontacting treatments. For example, part of a catalyst component is fed into a first precontacting vessel for precontacting with at least one other catalyst component, while the remainder of that same catalyst component is fed into a second precontacting vessel for precontacting with at least one other catalyst component, or is fed directly into the reactor, or a combination thereof. The precontacting can be carried out in any suitable equipment, such as tanks, stirred mix tanks, various static mixing devices, a flask, a vessel of any type, or combinations of these apparatus.

In another aspect of this invention, the various catalyst components (for example, a transition metal complex having formula (I), (II), and/or (III), activator-support, organoaluminum co-catalyst, and optionally an unsaturated hydrocarbon) can be contacted in the polymerization reactor simultaneously while the polymerization reaction is proceeding. Alternatively, any two or more of these catalyst components can be precontacted in a vessel prior to entering the reaction zone. This precontacting step can be continuous, in which the precontacted product is fed continuously to the reactor, or it can be a stepwise or batchwise process in which a batch of precontacted product is added to make a catalyst composition. This precontacting step can be carried out over a time period that can range from a few seconds to as much as several days, or longer. In this aspect, the continuous precontacting step generally lasts from about 1 second to about 1 hour. In another aspect, the continuous precontacting step lasts from about 10 seconds to about 45 minutes, or from about 1 minute to about 30 minutes.

Once the precontacted mixture of the transition metal compound having formula (I), (II), and/or (III), the olefin monomer, and the organoaluminum co-catalyst is contacted with the activator-support, this composition (with the addition of the activator-support) is termed the "postcontacted mixture." The postcontacted mixture optionally can remain in contact for a second period of time, the postcontact time, prior to initiating the polymerization process. Postcontact times between the precontacted mixture and the activator-support generally range from about 1 minute to about 24 hours. In a further aspect, the postcontact time is in a range from about 3 minutes to about 1 hour. The precontacting step, the postcontacting step, or both, can increase the productivity of the polymer as compared to the same catalyst composition that is prepared without precontacting or postcontacting. However, neither a precontacting step nor a postcontacting step is required.

The postcontacted mixture can be heated at a temperature and for a time period sufficient to allow adsorption, impregnation, or interaction of precontacted mixture and the activator-support, such that a portion of the components of the precontacted mixture is immobilized, adsorbed, or deposited thereon. Where heating is employed, the postcontacted mixture generally can be heated to a temperature of from between about −15° C. to about 70° C., or from about 0° C. to about 40° C.

When a precontacting step is used, the molar ratio of the total moles of olefin monomer to total moles of transition metal compound(s) in the precontacted mixture typically can be in a range from about 1:10 to about 100,000:1. Total moles of each component are used in this ratio to account for aspects of this invention where more than one olefin monomer and/or more than one transition metal complex is employed in a precontacting step. Further, this molar ratio can be in a range from about 10:1 to about 1,000:1 in another aspect of the invention.

Generally, the weight ratio of organoaluminum compound to activator-support can be in a range from about 10:1 to about 1:1000. If more than one organoaluminum compound and/or more than one activator-support is employed, this ratio is based on the total weight of each respective component. In another aspect, the weight ratio of the organoaluminum compound to the activator-support can be in a range from about 3:1 to about 1:100, or from about 1:1 to about 1:50.

In some aspects of this invention, the weight ratio of transition metal compound(s) to activator-support can be in a range from about 1:1 to about 1:1,000,000. If more than one activator-support is employed, this ratio is based on the total weight of the activator-support. In another aspect, this weight ratio can be in a range from about 1:5 to about 1:100,000, or from about 1:10 to about 1:10,000. Yet, in another aspect, the weight ratio of the transition metal compound(s) to the activator-support can be in a range from about 1:20 to about 1:1000.

Catalyst compositions of the present invention generally have a catalyst activity greater than about 100 grams of polyethylene (homopolymer, copolymer, etc., as the context requires) per millimole of transition metal per hour (abbreviated g/mmol/hr). In another aspect, the catalyst activity of the catalyst composition can be greater than about 200, greater than about 300, or greater than about 400 g/mmol/hr. In still another aspect, catalyst compositions of this invention can be characterized by having a catalyst activity greater than about 500, greater than about 750, or greater than about 1000 g/mmol/hr. Yet, in another aspect, the catalyst activity can be greater than about 2500 g/mmol/hr. This activity is measured under slurry polymerization conditions using isobutane as the diluent, at a polymerization temperature of about 80° C. and a reactor pressure of about 550 psig (3.8 MPa).

As discussed above, any combination of the transition metal compound having formula (I), (II), and/or (III), the activator-support, the organoaluminum compound, and the olefin monomer, can be precontacted in some aspects of this invention. When any precontacting occurs with an olefinic monomer, it is not necessary that the olefin monomer used in the precontacting step be the same as the olefin to be polymerized. Further, when a precontacting step among any combination of the catalyst components is employed for a first period of time, this precontacted mixture can be used in a subsequent postcontacting step between any other combination of catalyst components for a second period of time. For example, the transition metal compound, the organoaluminum compound, and 1-hexene can be used in a precontacting step for a first period of time, and this precontacted mixture then can be contacted with the activator-support to form a postcontacted mixture that is contacted for a second period of time prior to initiating the polymerization reaction. For example, the first period of time for contact, the precontact time, between any combination of the transition metal compound, the olefinic monomer, the activator-support, and the organoaluminum compound can be from about 1 minute to about 24 hours, from about 3 minutes to about 1 hour, or from about 10 minutes to about 30 minutes. The postcontacted mixture optionally is allowed to remain in contact for a second period of time, the postcontact time, prior to initiating the polymerization process. According to one aspect of this invention, postcontact times between the precontacted mixture and any remaining catalyst components is from about 1 minute to about 24 hours, or from about 5 minutes to about 1 hour.

Polymerization Process

Catalyst compositions of the present invention can be used to polymerize olefins to form homopolymers, copolymers, terpolymers, and the like. One such process for polymerizing olefins in the presence of a catalyst composition of the present invention can comprise contacting the catalyst composition with an olefin monomer and optionally an olefin comonomer (one or more) under polymerization conditions to produce an olefin polymer, wherein the catalyst composition can comprise a transition metal compound having formula (I), (II), and/or (III), and an activator and/or an organoaluminum compound. Transition metal complexes with a thiolate ligand having formula (I), (II), and/or (III), were discussed above.

In accordance with one aspect of the invention, the polymerization process can employ a catalyst composition comprising a transition metal compound having formula (I), (II), and/or (III), and an activator, wherein the activator comprises an activator-support. Activator-supports useful in the polymerization processes of the present invention were disclosed above. The catalyst composition can further comprise one or more than one organoaluminum compound or compounds (suitable organoaluminum compounds also were discussed above). Thus, a process for polymerizing olefins in the presence of a catalyst composition can employ a catalyst composition comprising a transition metal compound having formula (I), (II), and/or (III), an activator-support, and an organoaluminum compound. In some aspects, the activator-support can comprise (or consist essentially of, or consist of) fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, sulfated silica-coated alumina, phosphated silica-coated alumina, and the like, or combinations thereof. In some aspects, the organoaluminum compound can comprise (or consist essentially of, or consist of) trimethylaluminum, triethylaluminum, tri-n-propylaluminum, tri-n-butylaluminum, triisobutylaluminum, tri-n-hexylaluminum, tri-n-octylaluminum, diisobutylaluminum hydride, diethylaluminum ethoxide, diethylaluminum chloride, and the like, or combinations thereof.

In accordance with another aspect of the invention, the polymerization process can employ a catalyst composition comprising a transition metal compound having formula (I), (II), and/or (III), and an activator, wherein the activator comprises an aluminoxane compound, an organoboron or organoborate compound, an ionizing ionic compound, or combinations thereof.

The catalyst compositions of the present invention are intended for any olefin polymerization method using various types of polymerization reactors. As used herein, "polymerization reactor" includes any polymerization reactor capable of polymerizing olefin monomers and comonomers (one or more than one comonomer) to produce homopolymers, copolymers, terpolymers, and the like. The various types of reactors include those that may be referred to as a batch reactor, slurry reactor, gas-phase reactor, solution reactor, high pressure reactor, tubular reactor, autoclave reactor, and the like, or combinations thereof. The polymerization conditions for the various reactor types are well known to those of skill in the art. Gas phase reactors may comprise fluidized bed reactors or staged horizontal reactors. Slurry reactors may comprise vertical or horizontal loops. High pressure reactors may comprise autoclave or tubular reactors. Reactor types can include batch or continuous processes. Continuous processes could use intermittent or continuous product discharge. Processes may also include partial or full direct recycle of unreacted monomer, unreacted comonomer, and/or diluent.

Polymerization reactor systems of the present invention may comprise one type of reactor in a system or multiple reactors of the same or different type. Production of polymers in multiple reactors may include several stages in at least two separate polymerization reactors interconnected by a transfer device making it possible to transfer the polymers resulting from the first polymerization reactor into the second reactor. The desired polymerization conditions in one of the reactors may be different from the operating conditions of the other reactors. Alternatively, polymerization in multiple reactors may include the manual transfer of polymer from one reactor to subsequent reactors for continued polymerization. Multiple reactor systems may include any combination including, but not limited to, multiple loop reactors, multiple gas phase reactors, a combination of loop and gas phase reactors, multiple high pressure reactors, or a combination of high pressure with loop and/or gas phase reactors. The multiple reactors may be operated in series, in parallel, or both.

According to one aspect of the invention, the polymerization reactor system may comprise at least one loop slurry reactor comprising vertical or horizontal loops. Monomer, diluent, catalyst, and comonomer may be continuously fed to a loop reactor where polymerization occurs. Generally, continuous processes may comprise the continuous introduction of monomer/comonomer, a catalyst, and a diluent into a polymerization reactor and the continuous removal from this reactor of a suspension comprising polymer particles and the diluent. Reactor effluent may be flashed to remove the solid polymer from the liquids that comprise the diluent, monomer and/or comonomer. Various technologies may be used for this separation step including but not limited to, flashing that may include any combination of heat addition and pressure reduction; separation by cyclonic action in either a cyclone or hydrocyclone; or separation by centrifugation.

A typical slurry polymerization process (also known as the particle form process) is disclosed, for example, in U.S. Pat. Nos. 3,248,179, 4,501,885, 5,565,175, 5,575,979, 6,239,235, 6,262,191, and 6,833,415, each of which is incorporated herein by reference in its entirety.

Suitable diluents used in slurry polymerization include, but are not limited to, the monomer being polymerized and hydrocarbons that are liquids under reaction conditions. Examples of suitable diluents include, but are not limited to, hydrocarbons such as propane, cyclohexane, isobutane, n-butane, n-pentane, isopentane, neopentane, and n-hexane. Some loop polymerization reactions can occur under bulk conditions where no diluent is used. An example is polymerization of propylene monomer as disclosed in U.S. Pat. No. 5,455,314, which is incorporated by reference herein in its entirety.

According to yet another aspect of this invention, the polymerization reactor may comprise at least one gas phase reactor. Such systems may employ a continuous recycle stream containing one or more monomers continuously cycled through a fluidized bed in the presence of the catalyst under polymerization conditions. A recycle stream may be withdrawn from the fluidized bed and recycled back into the reactor. Simultaneously, polymer product may be withdrawn from the reactor and new or fresh monomer may be added to replace the polymerized monomer. Such gas phase reactors may comprise a process for multi-step gas-phase polymerization of olefins, in which olefins are polymerized in the gaseous phase in at least two independent gas-phase polymerization zones while feeding a catalyst-containing polymer formed in a first polymerization zone to a second polymerization zone. One type of gas phase reactor is disclosed in U.S. Pat. Nos. 5,352,749, 4,588,790, and 5,436,304, each of which is incorporated by reference in its entirety herein.

According to still another aspect of the invention, a high pressure polymerization reactor may comprise a tubular reactor or an autoclave reactor. Tubular reactors may have several zones where fresh monomer, initiators, or catalysts are added. Monomer may be entrained in an inert gaseous stream and introduced at one zone of the reactor. Initiators, catalysts, and/or catalyst components may be entrained in a gaseous stream and introduced at another zone of the reactor. The gas streams may be intermixed for polymerization. Heat and pressure may be employed appropriately to obtain optimal polymerization reaction conditions.

According to yet another aspect of the invention, the polymerization reactor may comprise a solution polymerization reactor wherein the monomer/comonomer are contacted with the catalyst composition by suitable stirring or other means. A carrier comprising an inert organic diluent or excess monomer may be employed. If desired, the monomer/comonomer may be brought in the vapor phase into contact with the catalytic reaction product, in the presence or absence of liquid material. The polymerization zone is maintained at temperatures and pressures that will result in the formation of a solution of the polymer in a reaction medium. Agitation may be employed to obtain better temperature control and to maintain uniform polymerization mixtures throughout the polymerization zone. Adequate means are utilized for dissipating the exothermic heat of polymerization.

Polymerization reactors suitable for the present invention may further comprise any combination of at least one raw material feed system, at least one feed system for catalyst or catalyst components, and/or at least one polymer recovery system. Suitable reactor systems for the present invention may further comprise systems for feedstock purification, catalyst storage and preparation, extrusion, reactor cooling, polymer recovery, fractionation, recycle, storage, loadout, laboratory analysis, and process control.

Polymerization conditions that are controlled for efficiency and to provide desired polymer properties can include temperature, pressure, and the concentrations of various reactants. Polymerization temperature can affect catalyst productivity, polymer molecular weight, and molecular weight distribution. A suitable polymerization temperature may be any temperature below the de-polymerization temperature according to the Gibbs Free energy equation. Typically, this includes from about 60° C. to about 280° C., for example, or from about 60° C. to about 110° C., depending upon the type of polymerization reactor. In some reactor systems, the polymerization temperature generally is within a range from about 70° C. to about 90° C., or from about 75° C. to about 85° C.

Suitable pressures will also vary according to the reactor and polymerization type. The pressure for liquid phase polymerizations in a loop reactor is typically less than 1000 psig (6.9 MPa). Pressure for gas phase polymerization is usually at about 200 to 500 psig (1.4 MPa to 3.4 MPa). High pressure polymerization in tubular or autoclave reactors is generally run at about 20,000 to 75,000 psig (138 to 517 MPa). Polymerization reactors can also be operated in a supercritical region occurring at generally higher temperatures and pressures. Operation above the critical point of a pressure/temperature diagram (supercritical phase) may offer advantages.

Aspects of this invention also are directed to olefin polymerization processes conducted in the absence of added hydrogen. In this disclosure, "added hydrogen" will be denoted as the feed ratio of hydrogen to olefin monomer entering the reactor (in units of ppm). An olefin polymerization process of this invention can comprise contacting a catalyst composition with an olefin monomer and optionally an olefin comonomer under polymerization conditions to produce an olefin polymer, wherein the catalyst composition can comprise a transition metal complex and an activator, wherein the polymerization process is conducted in the absence of added hydrogen. As disclosed above, the transition metal complex can have formula (I), formula (II), and/or formula (III). As one of ordinary skill in the art would recognize, hydrogen can be generated in-situ by transition metal catalyst compositions in various olefin polymerization processes, and the amount generated may vary depending upon the specific catalyst composition and transition metal compound(s) employed, the type of polymerization process used, the polymerization reaction conditions utilized, and so forth.

In other aspects, it may be desirable to conduct the polymerization process in the presence of a certain amount of added hydrogen. Accordingly, an olefin polymerization process of this invention can comprise contacting a catalyst composition with an olefin monomer and optionally an olefin comonomer under polymerization conditions to produce an olefin polymer, wherein the catalyst composition comprises a transition metal compound and an activator, wherein the polymerization process is conducted in the presence of added hydrogen. For example, the ratio of hydrogen to the olefin monomer in the polymerization process can be controlled, often by the feed ratio of hydrogen to the olefin monomer entering the reactor. The added hydrogen to olefin monomer ratio in the process can be controlled at a weight ratio which falls within a range from about 25 ppm to about 1500 ppm, from about 50 to about 1000 ppm, or from about 100 ppm to about 750 ppm.

In some aspects of this invention, the feed or reactant ratio of hydrogen to olefin monomer can be maintained substantially constant during the polymerization run for a particular polymer grade. That is, the hydrogen:olefin monomer ratio can be selected at a particular ratio within a range from about 5 ppm up to about 1000 ppm or so, and maintained at the ratio to within about +/−25% during the polymerization run. For instance, if the target ratio is 100 ppm, then maintaining the hydrogen:olefin monomer ratio substantially constant would entail maintaining the feed ratio between about 75 ppm and about 125 ppm. Further, the addition of comonomer (or comonomers) can be, and generally is, substantially constant throughout the polymerization run for a particular polymer grade.

However, in other aspects, it is contemplated that monomer, comonomer (or comonomers), and/or hydrogen can be periodically pulsed to the reactor, for instance, in a manner similar to that employed in U.S. Pat. No. 5,739,220 and U.S. Patent Publication No. 2004/0059070, the disclosures of which are incorporated herein by reference in their entirety.

The concentration of the reactants entering the polymerization reactor can be controlled to produce resins with certain physical and mechanical properties. The proposed end-use product that will be formed by the polymer resin and the method of forming that product ultimately can determine the desired polymer properties and attributes. Mechanical properties include tensile, flexural, impact, creep, stress relaxation, and hardness tests. Physical properties include density, molecular weight, molecular weight distribution, melting temperature, glass transition temperature, temperature melt of crystallization, density, stereoregularity, crack growth, long chain branching, and rheological measurements.

This invention is also directed to, and encompasses, the polymers produced by any of the polymerization processes disclosed herein. Articles of manufacture can be formed from, and/or can comprise, the polymers produced in accordance with this invention.

Polymers and Articles

If the resultant polymer produced in accordance with the present invention is, for example, a polymer or copolymer of ethylene, its properties can be characterized by various analytical techniques known and used in the polyolefin industry. Articles of manufacture can be formed from, and/or can comprise, the ethylene polymers of this invention, whose typical properties are provided below.

Polymers of ethylene (copolymers, terpolymers, etc.) produced in accordance with this invention generally can have a melt index from 0 to about 100 g/10 min. Melt indices in the range from 0 to about 75 g/10 min, from 0 to about 50 g/10 min, or from 0 to about 30 g/10 min, are contemplated in some aspects of this invention. For example, a polymer of the present invention can have a melt index (MI) in a range from 0 to about 25, from 0 to about 10, from 0 to about 5, from 0 to about 2, or from 0 to about 1 g/10 min.

The density of ethylene-based polymers produced using one or more transition metal compounds of the present invention typically can fall within the range from about 0.88 to about 0.97 g/cc. In one aspect of this invention, the polymer density can be in a range from about 0.90 to about 0.97 g/cc. Yet, in another aspect, the density generally can be in a range from about 0.91 to about 0.96 g/cc.

Ethylene polymers, such as homopolymers, copolymers, and terpolymers, within the scope of the present invention generally can have a weight-average molecular weight (Mw) of greater than about 500,000 g/mol. In some aspects, the Mw of the polymer is greater than about 750,000 g/mol, while in other aspects, the Mw of the polymer is greater than about 1,000,000 g/mol. Contemplated Mw ranges encompassed by the present invention can include, but are not limited to, from about 500,000 to about 2,000,000 g/mol, from about 550,000 to about 1,800,000 g/mol, from about 600,000 to about 1,700,000 g/mol, from about 700,000 to about 1,500,000 g/mol, or from about 800,000 to about 1,300,000 g/mol.

The ratio of Mw/Mn, or polydispersity index, for the polymers of this invention often can be in a range from about 3 to about 100. In some aspects disclosed herein, the ratio of Mw/Mn can be in a range from about 3 to about 80, from about 3.5 to about 80, from about 3 to about 75, or from about 4 to about 70. In certain aspects, the ratio of Mw/Mn can be in a range from about 5 to about 35, or from about 6 to about 30.

Polymers of ethylene, whether homopolymers, copolymers, terpolymers, and so forth, can be formed into various articles of manufacture. Articles which can comprise polymers of this invention include, but are not limited to, an agricultural film, an automobile part, a bottle, a drum, a fiber or fabric, a food packaging film or container, a food service article, a fuel tank, a geomembrane, a household container, a liner, a molded product, a medical device or material, a pipe, a sheet or tape, a toy, and the like. Various processes can be employed to form these articles. Non-limiting examples of these processes can include injection molding, blow molding, rotational molding, film extrusion, sheet extrusion, profile extrusion, thermoforming, and the like. Additionally, additives and modifiers are often added to these polymers in order to provide beneficial polymer processing or end-use product attributes. Such processes and materials are described in *Modern Plastics Encyclopedia*, Mid-November 1995 Issue, Vol. 72, No. 12; and *Film Extrusion Manual—Process, Materials, Properties*, TAPPI Press, 1992; the disclosures of which are incorporated herein by reference in their entirety.

Applicants also contemplate a method for forming or preparing an article of manufacture comprising a polymer produced by any of the polymerization processes disclosed herein. For instance, a method can comprise (i) contacting a catalyst composition with an olefin monomer and optionally an olefin comonomer (one or more) under polymerization conditions to produce an olefin polymer, wherein the catalyst composition can comprise a transition metal complex having formula (I), (II), and/or (III), and an activator (e.g., an activator-support) and/or an organoaluminum compound; and (ii) forming an article of manufacture comprising the olefin polymer. The forming step can comprise blending, melt processing, extruding, molding, or thermoforming, and the like, including combinations thereof.

EXAMPLES

The invention is further illustrated by the following examples, which are not to be construed in any way as imposing limitations to the scope of this invention. Various other aspects, embodiments, modifications, and equivalents thereof which, after reading the description herein, may suggest themselves to one of ordinary skill in the art without departing from the spirit of the present invention or the scope of the appended claims.

Unless otherwise noted, all operations were performed under purified nitrogen or vacuum using standard Schlenk or glovebox techniques. Et$_2$O and THF were purchased as anhydrous from Aldrich and used as received. Pentane, hexanes and heptanes (Fischer Scientific) were degassed and stored over activated 13× molecular sieves under nitrogen. Ti(NMe$_2$)$_4$, tetrabenzylzirconium, and tetrabenzylhafnium were purchased from Strem and used as received. Zr(NEt$_2$)$_4$, V(=O)(O$^i$Pr)$_3$, diphenyl ether, diphenyl sulfide, N-methyldiphenylamine, 2.5M nBuLi in hexanes, trimethylsilylchloride (TMSCl), N,N,N',N'-tetramethylethylenediamine (TMEDA), 1M triisobutylaluminum (TIBA) in hexanes, 10% MAO in toluene, and allylchlorodimethylsilane were purchased from Sigma-Aldrich and used as received. Davison 952 SiO$_2$ was calcined at 800° C. prior to use.

C$_6$D$_6$ (Cambridge Isotope Laboratories) was degassed and dried over 13× molecular sieves under nitrogen. CDCl$_3$ (Cambridge isotope Laboratories) was used as received. Chemical shifts (δ) for $^1$H NMR spectra are given relative to residual protium in the deuterated solvent at 7.27 and 7.16 for CDCl$_3$ and C$_6$D$_6$, respectively.

Approximately 20% MAO on SiO$_2$ was prepared as follows. 17 g of Davison 952 SiO$_2$ was charged to a 500-mL round-bottomed flask equipped with stirbar. A 10% MAO solution in toluene (57 mL) was added, resulting in a yellowish slurry. Pentane (500 mL) was added to the slurry and the solution was cooled to −20° C. overnight. The suspension was filtered and dried in vacuo.

Fluorided silica-alumina activator-supports were prepared as follows. A silica-alumina was obtained from W.R. Grace Company containing about 13% alumina by weight and having a surface area of about 400 m$^2$/g and a pore volume of about 1.2 mL/g. This material was obtained as a powder having an average particle size of about 70 microns. Approximately 100 grams of this material were impregnated with a solution containing about 200 mL of water and about 10 grams of ammonium hydrogen fluoride, resulting in a damp powder having the consistency of wet sand. This mixture was then placed in a flat pan and allowed to dry under vacuum at approximately 110° C. for about 16 hours. To calcine the support, about 10 grams of this powdered mixture were placed in a 1.75-inch quartz tube fitted with a sintered quartz disk at the bottom. While the powder was supported on the disk, air (nitrogen can be substituted) dried by passing through a 13× molecular sieve column, was blown upward through the disk at the linear rate of about 1.6 to 1.8 standard cubic feet per hour. An electric furnace around the quartz tube was then turned on and the temperature was raised at the rate of about 400° C. per hour to the desired calcining temperature of about 450° C. At this temperature, the powder was allowed to fluidize for about three hours in the dry air. Afterward, the fluorided silica-alumina (abbreviated "FSA" in the tables that followed) was collected and stored under dry nitrogen, and was used without exposure to the atmosphere.

Fluorided silica-coated alumina activator-supports were prepared as follows. A silica-coated alumina was obtained from Sasol Company under the Siral 28M designation. Approximately 65 g of ammonium bifluoride were dissolved in 2.3 L of methanol, and this methanol solution was added to 650 g of Siral 28M in a 4-L beaker while stirring. This wet mixture was then allowed to dry under vacuum at approximately 100° C. for about 16 hours. To calcine the resultant powdered mixture, a portion of the material was fluidized in a stream of dry nitrogen at about 600° C. for about 3 hours. Afterward, the fluorided silica-coated alumina (abbreviated "M-SSA" in the tables that followed) was collected and stored under dry nitrogen, and was used without exposure to the atmosphere.

Sulfated alumina activator-supports were prepared as follows. Bohemite was obtained from W.R. Grace Company under the designation "Alumina A" and having a surface area of about 300 m$^2$/g and a pore volume of about 1.3 mL/g. This material was obtained as a powder having an average particle size of about 100 microns. This material was impregnated to incipient wetness with an aqueous solution of ammonium sulfate to equal about 15% sulfate. This mixture was then placed in a flat pan and allowed to dry under vacuum at approximately 110° C. for about 16 hours. To calcine the resultant powdered mixture, the material was fluidized in a stream of dry air at about 550° C. for about 6 hours. Afterward, the sulfated alumina (abbreviated "SA" in the tables that followed) was collected and stored under dry nitrogen, and was used without exposure to the atmosphere.

Polymerization experiments were conducted in a 1-gallon autoclave reactor, equipped with a 900 rpm stirrer. The reactor temperature was maintained at the desired run temperature throughout the run by an automated heating-cooling system. The catalyst system components were added to the reactor at a temperature below 40° C. and under an isobutane purge. The reactor was then sealed, 2 L of isobutane were added, and stirring was started at 900 rpm. The reactor was heated, and as the reactor temperature approached the target polymerization temperature, ethylene was added to the reactor. Then, the target temperature and pressure were rapidly attained. Ethylene was fed on demand to maintain the target reactor pressure during the determined run time (typically, 30 min or 60 min). At the end of the run, isobutene, ethylene, and other volatiles were vented from the reactor, the reactor was opened, and the polymer product was collected and dried.

Molecular weights and molecular weight distributions were obtained using a PL 220 SEC high temperature chromatography unit (Polymer Laboratories) with trichlorobenzene (TCB) as the solvent, with a flow rate of 1 mL/minute at a temperature of 145° C. BHT (2,6-di-tert-butyl-4-methylphenol) at a concentration of 0.5 g/L was used as a stabilizer in the TCB. An injection volume of 200 µL was used with a nominal polymer concentration of 1.5 mg/mL. Dissolution of the sample in stabilized TCB was carried out by heating at 150° C. for 5 hours with occasional, gentle agitation. The columns used were three PLgel Mixed A LS columns (7.8× 300 mm) and were calibrated with a broad linear polyethylene standard (Phillips Marlex® BHB 5003) for which the molecular weight had been determined. In the examples that follow, Mn is the number-average molecular weight (g/mol); Mw is the weight-average molecular weight (g/mol); Mz is the z-average molecular weight (g/mol); and PDI is the polydispersity index, the ratio of Mw/Mn.

Example 1

Synthesis of a Ligand with a Central Donor Atom Capped by Two Aryl Thiolates, Compound 3a The general synthesis scheme for compound 3a is shown below:

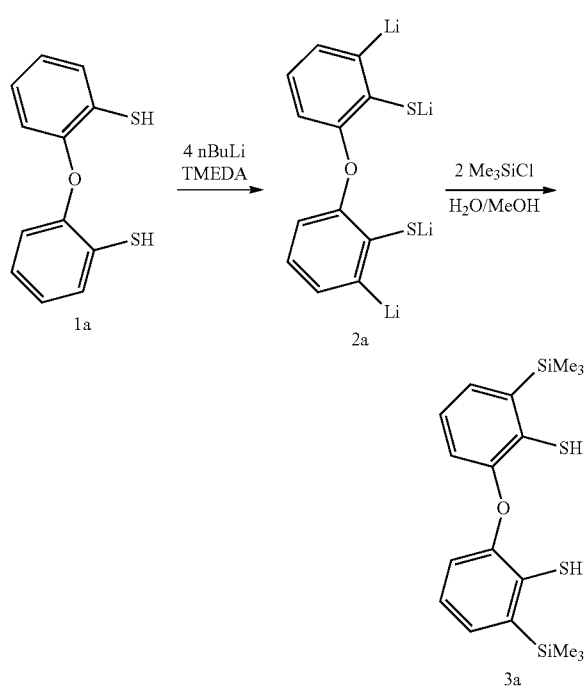

Compound 1a, $O(C_6H_4SH)_2$, was prepared in accordance with the procedure described in *Eur. J. Inorg. Chem.* 2003, 3554-3562, the disclosure of which is incorporated herein by reference in its entirety. Corresponding S and NMe versions can be prepared in accordance with the procedures described in *Eur. J. Inorg. Chem.* 1999, 1715-1725, and *Inorg. Chem.* 1995, 34, 6562-6564, the disclosures of which are incorporated herein by reference in their entirety.

Approximately 150 mL hexanes were added to $O(C_6H_4SH)_2$ (compound 1a) (3.03 g, 12.9 mmol) in a 500-mL round-bottomed flask equipped with a stirbar. The mixture was cooled to 0° C., then a 2.5 M solution of nBuLi in hexanes (22.4 mL, 56.1 mmol) was added to the flask, resulting in a fine white precipitate. TMEDA (15.5 mL, 103.5 mmol) addition by syringe dissolved the precipitate. This mixture was warmed to ambient temperature and stirred for three days. The resultant beige suspension was cooled to 0° C. and TMSCl (7.44 mL, 58.9 mmol) was added via syringe. The suspension was warmed to ambient temperature with stirring for 18 hr. This reaction mixture was quenched with 60 mL of water. The volatiles were stripped off and $Et_2O$ (150 mL) was then added. The organics were separated and washed with 2×100 mL of 5% HCl (aq), dried over $MgSO_4$, and filtered through a pad of celite. The volatiles were removed, leaving a yellow oil which was heated to reflux in MeOH (50 mL) for 18 hr. The MeOH was removed, and the residue was extracted with 50 mL of hexanes. A fine precipitate was filtered off and the volatiles were evacuated leaving compound 3a as a yellow oil (2.97 g, 60.7%). $^1$H NMR ($CDCl_3$): δ 7.23 (dd, J=1.5, 7.5 Hz, 2H), δ 7.08 (t, J=7.5 Hz, 2H), δ 6.81 (dd, J=1.5, 7.5 Hz, 2H), δ 4.36 (s, 2H, SH), δ 0.47 (s, 18H, $SiMe_3$). FIG. 1 illustrates the $^1$H-NMR analysis of compound 3a.

Example 2

Synthesis of a Ligand with a Central Donor Atom Capped by Two Aryl Thiolates, Compound 4c Approximately 50 mL hexanes were added to MeN $(C_6H_4SH)_2$ (0.985 g, 3.98 mmol) in a 100-mL round-bottomed flask equipped with a stirbar. The mixture was cooled to 0° C., then a 2.5 M solution of nBuLi in hexanes (6.90 mL, 17.3 mmol) was added, resulting in a fine white precipitate. TMEDA (4.77 mL, 31.8 mmol) addition by syringe dissolved the precipitate. This mixture was warmed to ambient temperature and stirred for three days. The resultant beige suspension was cooled to 0° C. and allyl(chloro)dimethylsilane (2.70 mL, 17.9 mmol) was added via syringe. The suspension was warmed to ambient temperature with stirring for 18 hr. The reaction mixture was quenched with 25 mL, of water. The volatiles were stripped off and $Et_2O$ (50 mL) was then added. Next, the pH was adjusted to 6 with 1% HCl. The organics were separated and washed with 2×50 mL of sat $NH_4Cl$ (aq), dried over $MgSO_4$, and filtered through a pad of celite. The volatiles were removed, leaving a yellow oil which was heated to reflux in MeOH (30 mL) for 18 hr. The MeOH was removed, and the residue was extracted with 30 mL of hexanes. A fine precipitate was filtered off and the volatiles were evacuated leaving 4c (0.92 g) in 70% purity by $^1$H NMR ($CDCl_3$). A portion of the synthesis scheme for compound 4c is illustrated below:

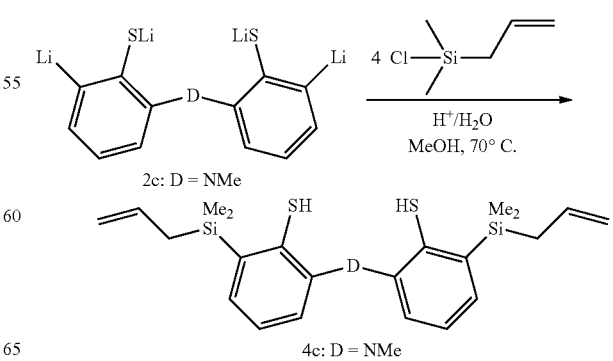

Examples 3-5

Synthesis of Titanium, Zirconium, and Hafnium Complexes with Thiolate Ligand, Compound 6, Compound 7a, and Compound 7b The general synthesis scheme for compounds 6-7a-7b is shown below:

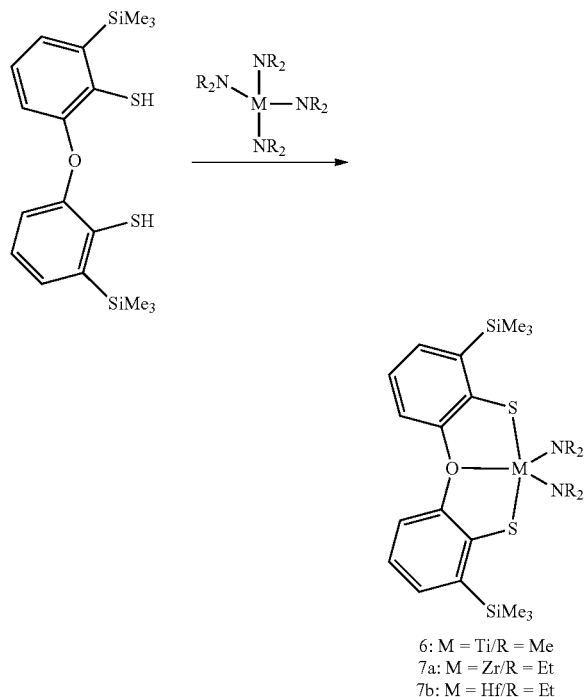

6: M = Ti/R = Me
7a: M = Zr/R = Et
7b: M = Hf/R = Et

Figure 2:
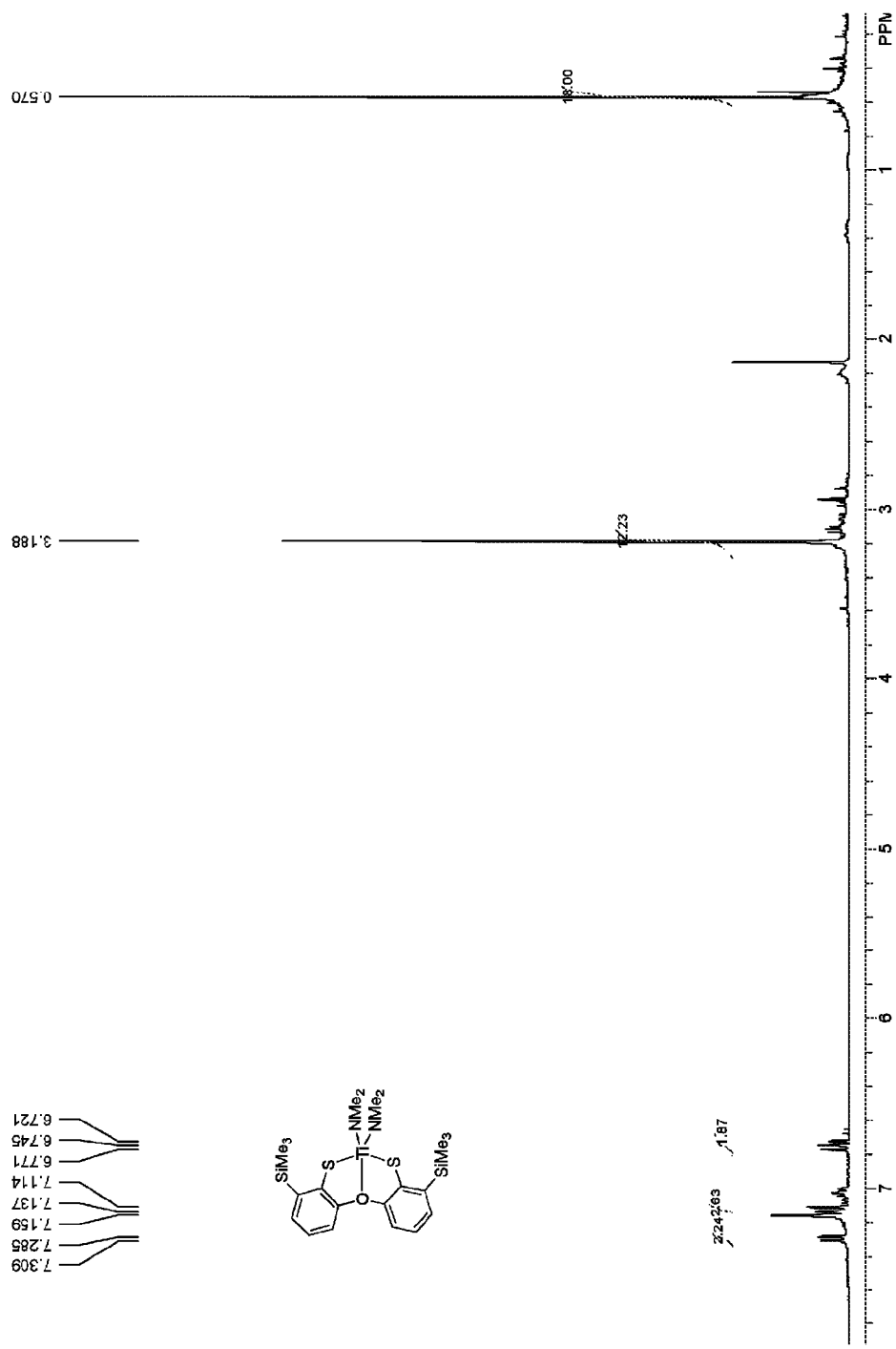
FIG. 2 presents a $^1$H-NMR plot of titanium complex 6.

Compound 6 was synthesized as follows. A 1-mL toluene solution of compound 3a (0.106 g, 0.281 mmol) was added to a toluene (1 mL) solution of $Ti(NMe_2)_4$ (0.063 g, 0.281 mmol), forming a red solution. The solution was stirred at ambient temperature overnight, during which time the solution lightened to orange-red. The volatiles were removed, leaving a red oil in quantitative yield. $^1$H NMR ($C_6D_6$): δ 7.30 (dd, J=0.9, 7.2 Hz, 2H), δ 7.14 (dd, J=0.9, 7.8 Hz, 2H), δ 6.74 (t, J=8.1 Hz, 2H), δ 3.19 (s, 12H, $Ti(NMe_2)_2$), δ 0.57 (s, 18H, $SiMe_3$). FIG. 2 illustrates the $^1$H-NMR analysis of compound 6.

Figure 3:
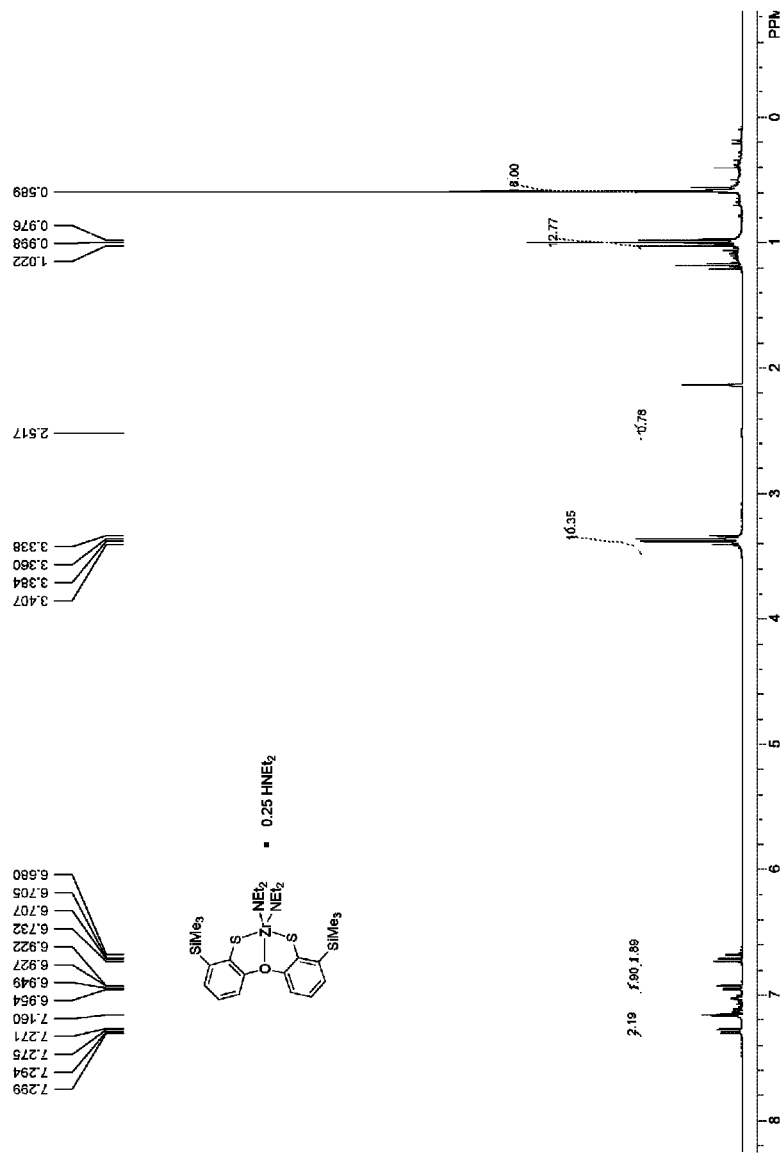

Compound 7a was synthesized as follows. A 1-mL toluene solution of compound 3a (0.117 g, 0.308 mmol) was added to a toluene (1 mL) solution of $Zr(NEt_2)_4$ (0.117 g, 0.308 mmol), forming a yellow solution. The solution was stirred at ambient temperature overnight. The volatiles were removed, leaving a yellow oil in quantitative yield. $^1$H NMR ($C_6D_6$): δ 7.29 (dd, J=1.4, 7.2 Hz, 2H), δ 6.94 (dd, J=1.4, 8.1 Hz, 2H), δ 6.71 (t, J=8.1 Hz, 2H), δ 3.37 (q, J=7.2 Hz, 8H, $Zr(N(CH_2CH_3)_2)_2$), δ 1.00 (t, J=7.2 Hz, 12H, $Zr(N(CH_2CH_3)_2)_2$), δ 0.59 (s, 18H, $SiMe_3$). A small amount of $HNEt_2$ was present. FIG. 3 illustrates the $^1$H-NMR analysis of compound 7a.

Compound 7b was synthesized as follows. A 1-mL toluene solution of compound 3a (0.047 g, 0.125 mmol) was added to a toluene (1 mL) solution of $Hf(NEt_2)_4$ (0.058 g, 0.125 mmol), forming a pale yellow solution. The solution was stirred at ambient temperature overnight. The volatiles were removed, leaving a yellow oil in quantitative yield. $^1$H NMR ($C_6D_6$): δ 7.28 (d, J=8.8 Hz, 2H), δ 6.92 (d, J=8.4 Hz, 2H), δ 6.68 (t, J=8.2 Hz, 2H), δ 3.41 (q, J=7.2 Hz, 8H, $Hf(N(CH_2CH_3)_2)_2$), δ 0.98 (t, J=7.2 Hz, 12H, $Hf(N(CH_2CH_3)_2)_2$), δ 0.56 (s, 18H, $SiMe_3$). A small amount of $HNEt_2$ was present.

Examples 6-7

Synthesis of Zirconium and Hafnium Complexes with Thiolate Ligands, Compounds 8-9

The general synthesis scheme for compounds 8-9 is shown below:

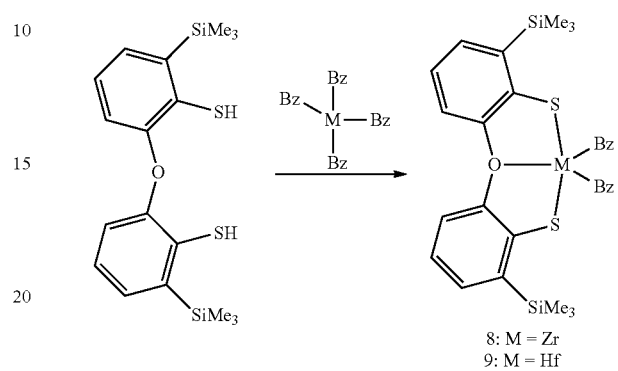

8: M = Zr
9: M = Hf

Figure 4:
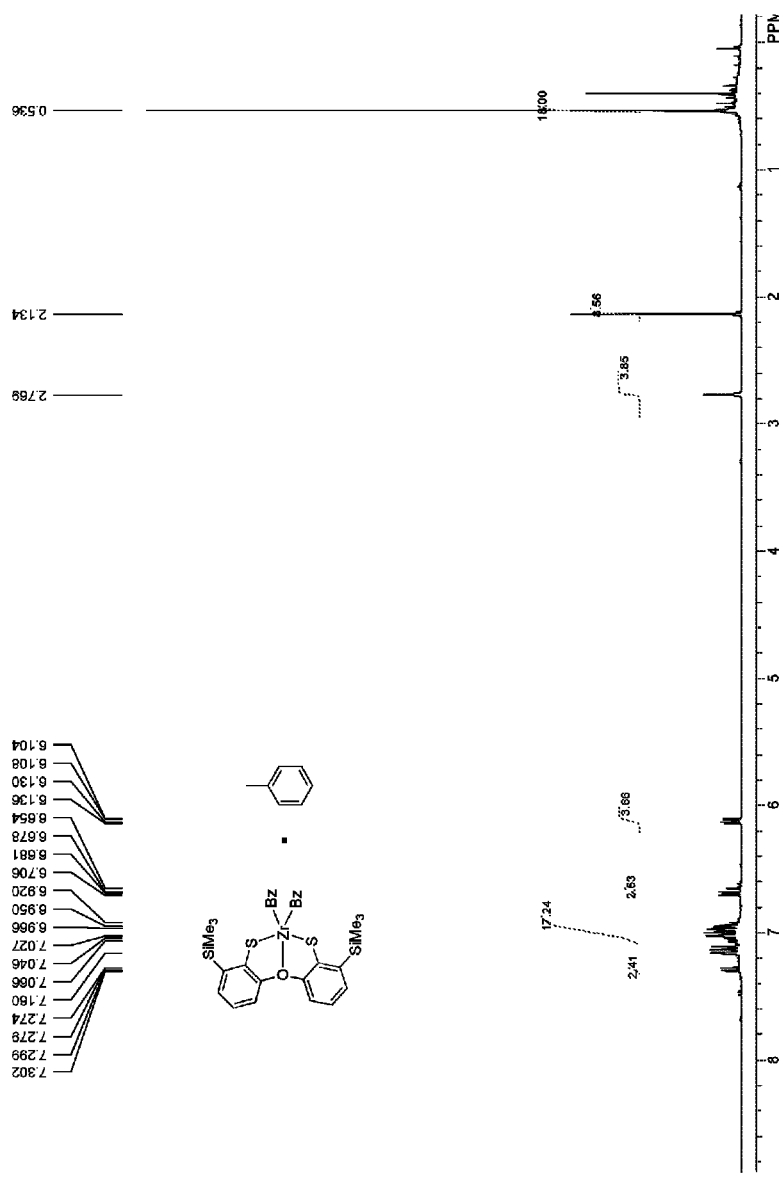
FIG. 4 presents a $^1$H-NMR plot of zirconium complex 8.

Compound 8 was synthesized as follows. A 1-mL $C_6D_6$ solution of compound 3a (0.054 g, 0.143 mmol) was added to a $C_6D_6$ (1 mL) solution of $ZrBz_4$ (0.045 g, 0.10 mmol), forming a yellow solution. The solution was stirred at ambient temperature overnight, during which time the solution turned orange. The volatiles were removed, leaving an orange solid. $^1$H NMR ($C_6D_6$): δ 7.30 (dd, J=0.9, 7.2 Hz, 2H), δ 7.1-6.9 (mult, 8H), δ 6.68 (t, J=8.1 Hz, 2H), δ 6.12 (d, J 6.6 Hz, 4H), δ 2.77 (s, 4H, $ZrCH_2Ph$), δ 0.54 (s, 18H, $SiMe_3$). FIG. 4 illustrates the $^1$H-NMR analysis of compound 8.

Figure 5:
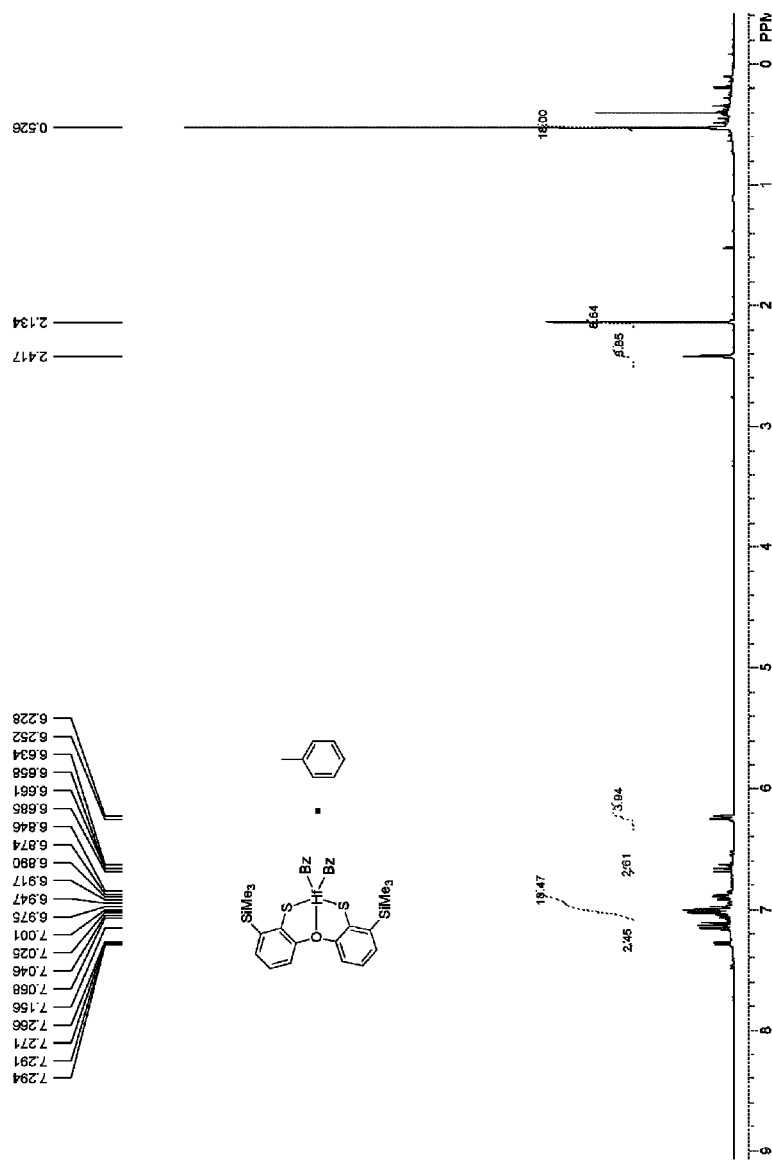
FIG. 5 presents a $^1$H-NMR plot of hafnium complex 9.

Compound 9 was synthesized as follows. A 1-mL $C_6D_6$ solution of compound 3a (0.063 g, 0.166 mmol) was added to a $C_6D_6$ (1 mL) solution of $HfBz_4$ (0.077 g, 0.141 mmol), forming a yellow solution. The solution was stirred at ambient temperature overnight. The volatiles were removed, leaving a yellow solid. $^1$H NMR ($C_6D_6$): δ 7.29 (dd, J=1.2, 7.2 Hz, 2H), δ 7.1-6.9 (mult, 8H), δ 6.66 (t, J=7.8 Hz, 2H), δ 6.24 (d, J=7.2 Hz, 4H), δ 2.42 (s, 4H, $HfCH_2Ph$), δ 0.53 (s, 18H, $SiMe_3$). FIG. 5 illustrates the $^1$H-NMR analysis of compound 9.

Example 8

Synthesis of a Vanadium Complex with Thiolate Ligands, Compound 10

The general synthesis scheme for compound 10 is shown below:

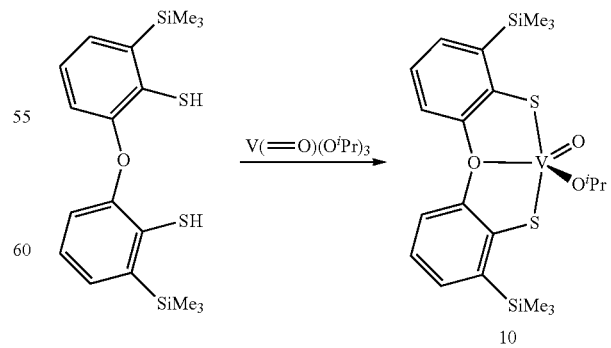

10

Figure 6:
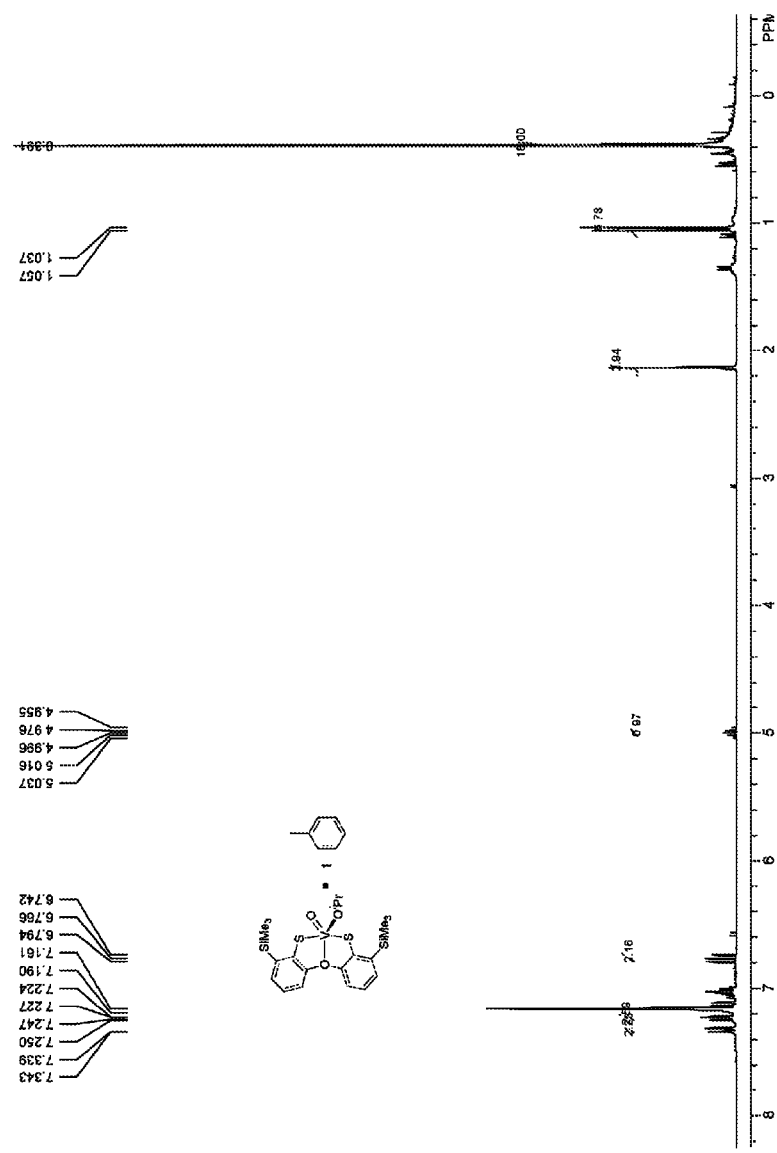
FIG. 6 presents a $^1$H-NMR plot of vanadium complex 10.
Figure 7:
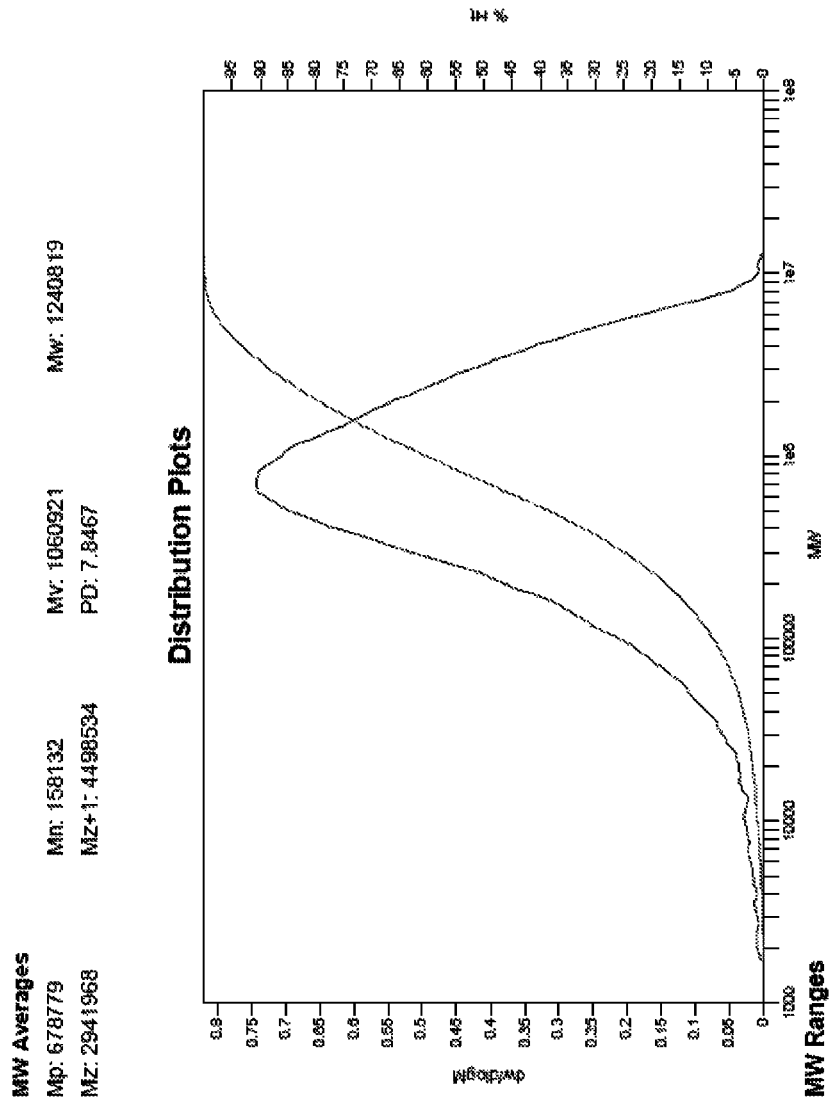
FIG. 7 presents a plot of the molecular weight distribution of the polymer of Example 19.
Figure 8:
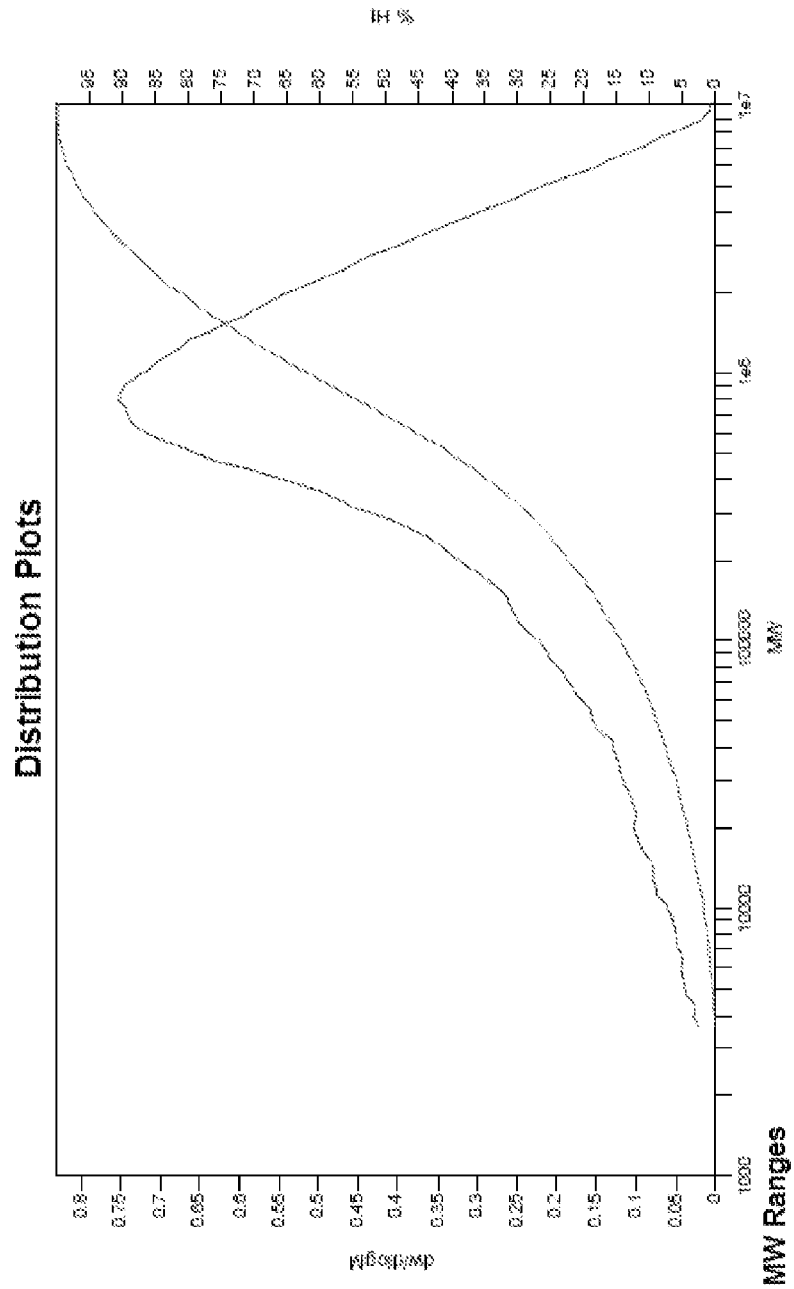
FIG. 8 presents a plot of the molecular weight distribution of the polymer of Example 21.
Figure 9:
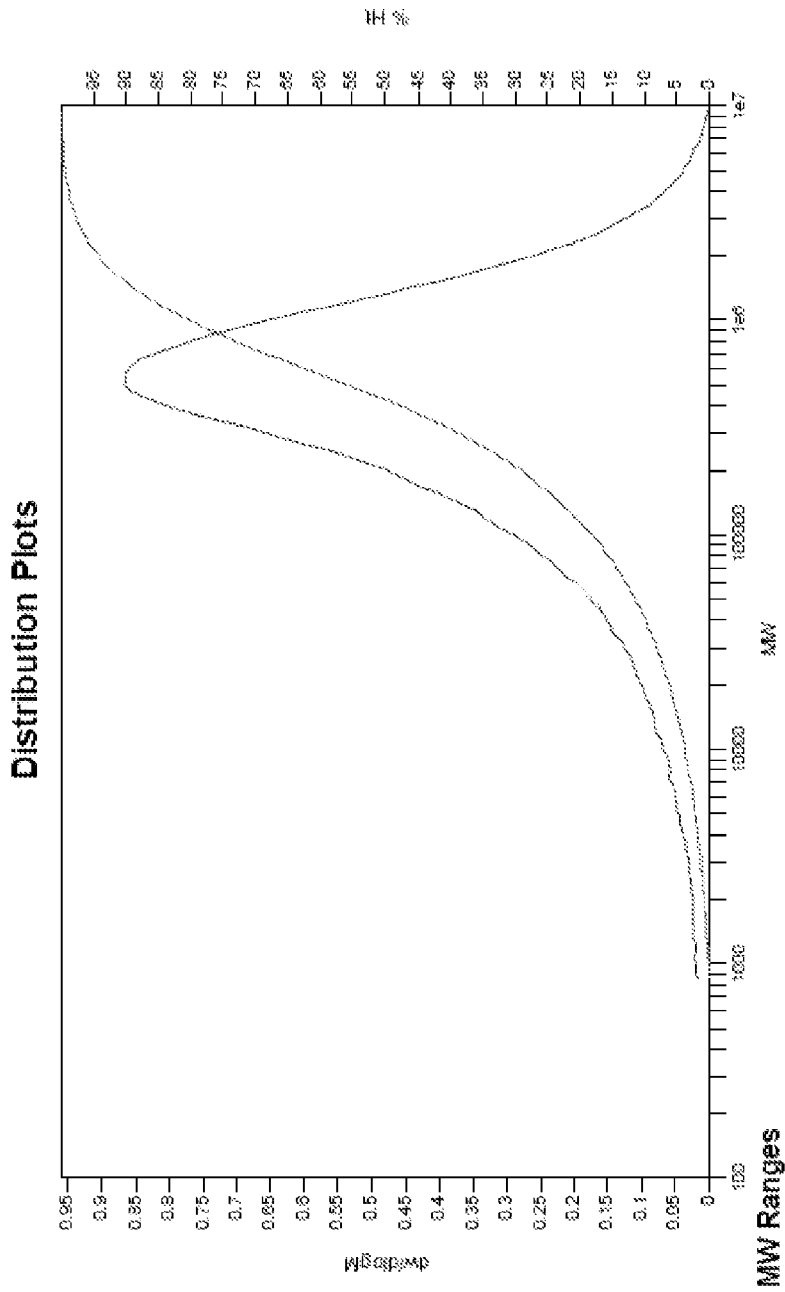
FIG. 9 presents a plot of the molecular weight distribution of the polymer of Example 22.
Figure 10:
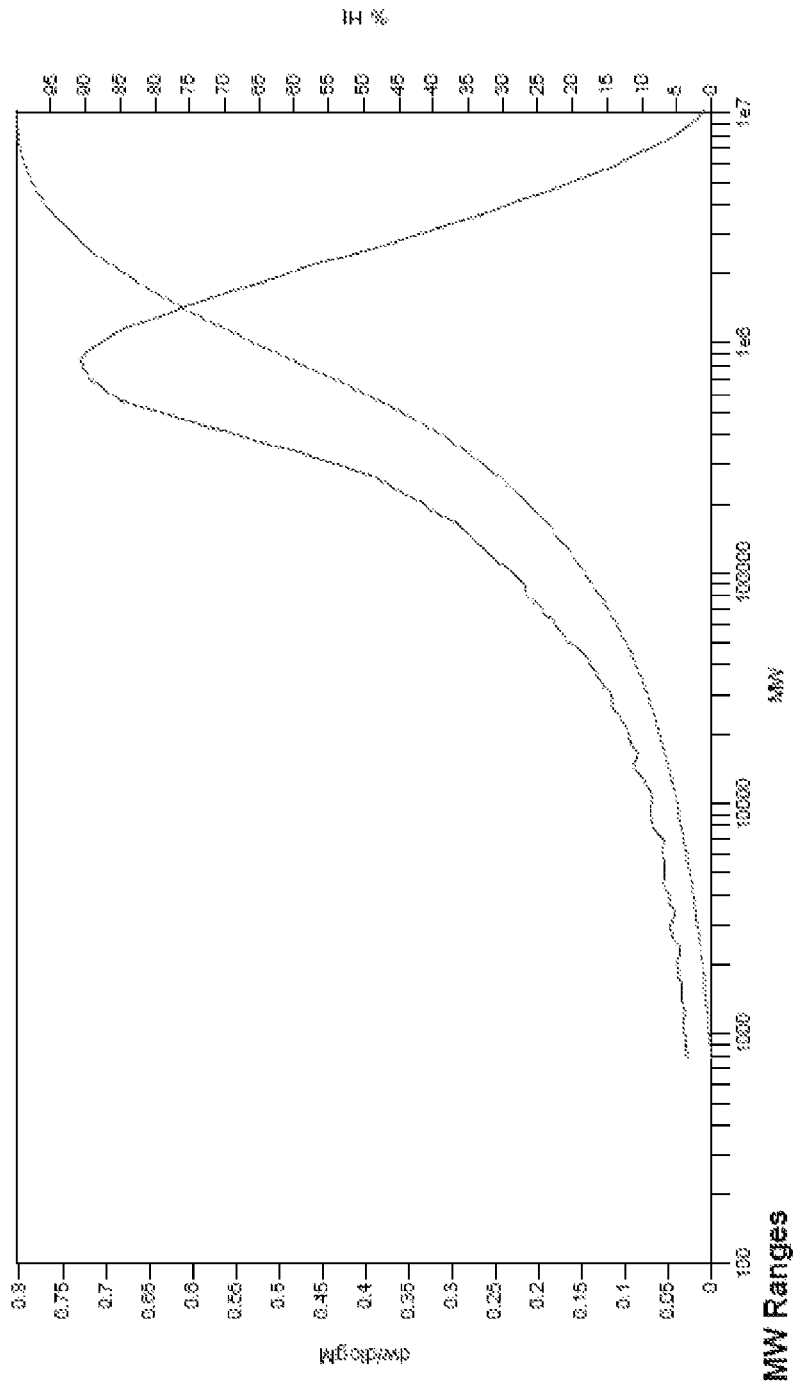
FIG. 10 presents a plot of the molecular weight distribution of the polymer of Example 23.
Figure 11:
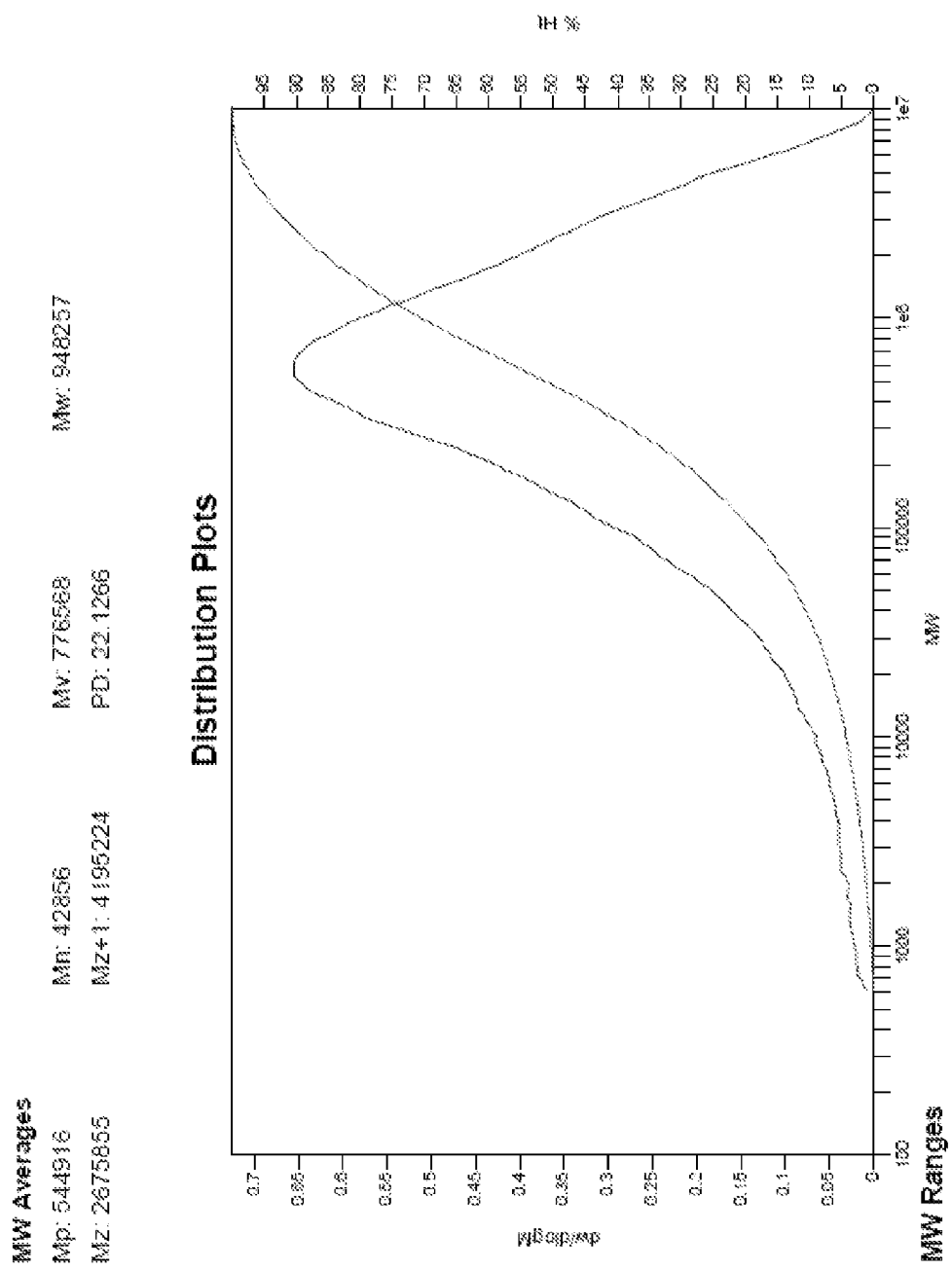
FIG. 11 presents a plot of the molecular weight distribution of the polymer of Example 24.
Figure 12:
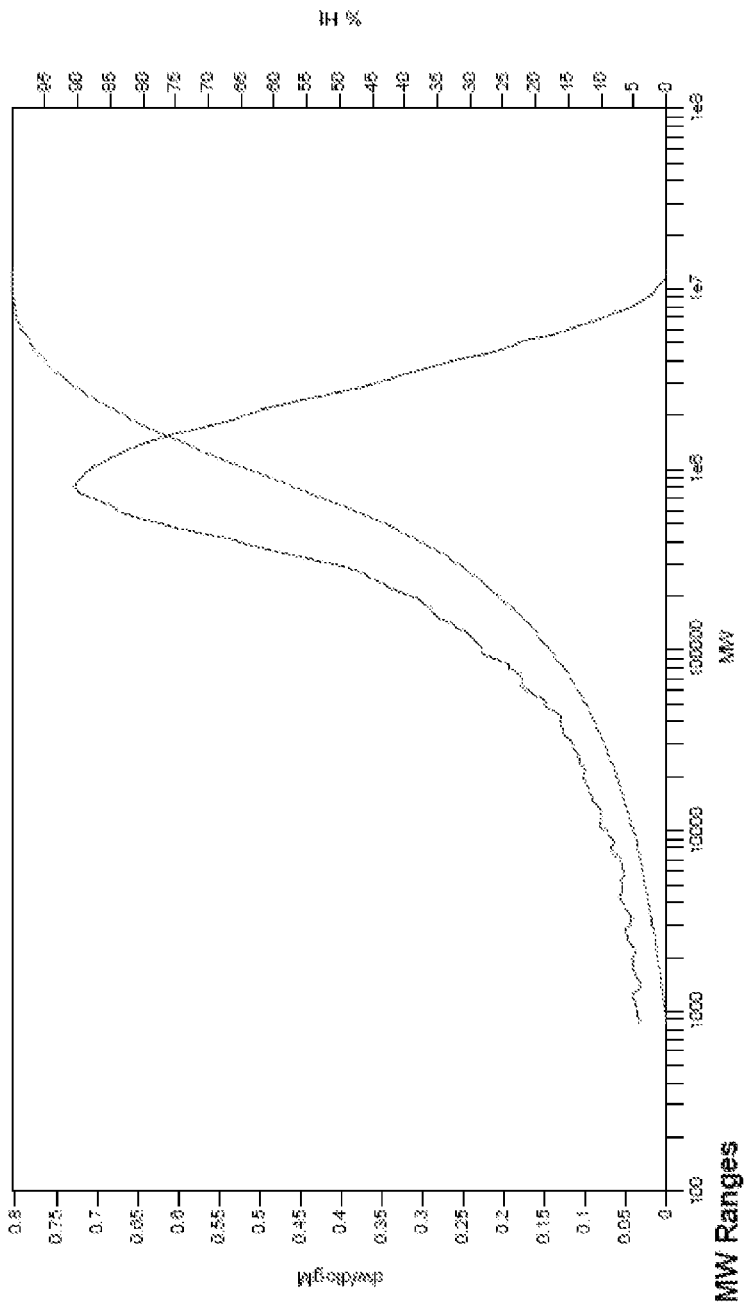
FIG. 12 presents a plot of the molecular weight distribution of the polymer of Example 25.
Figure 13:
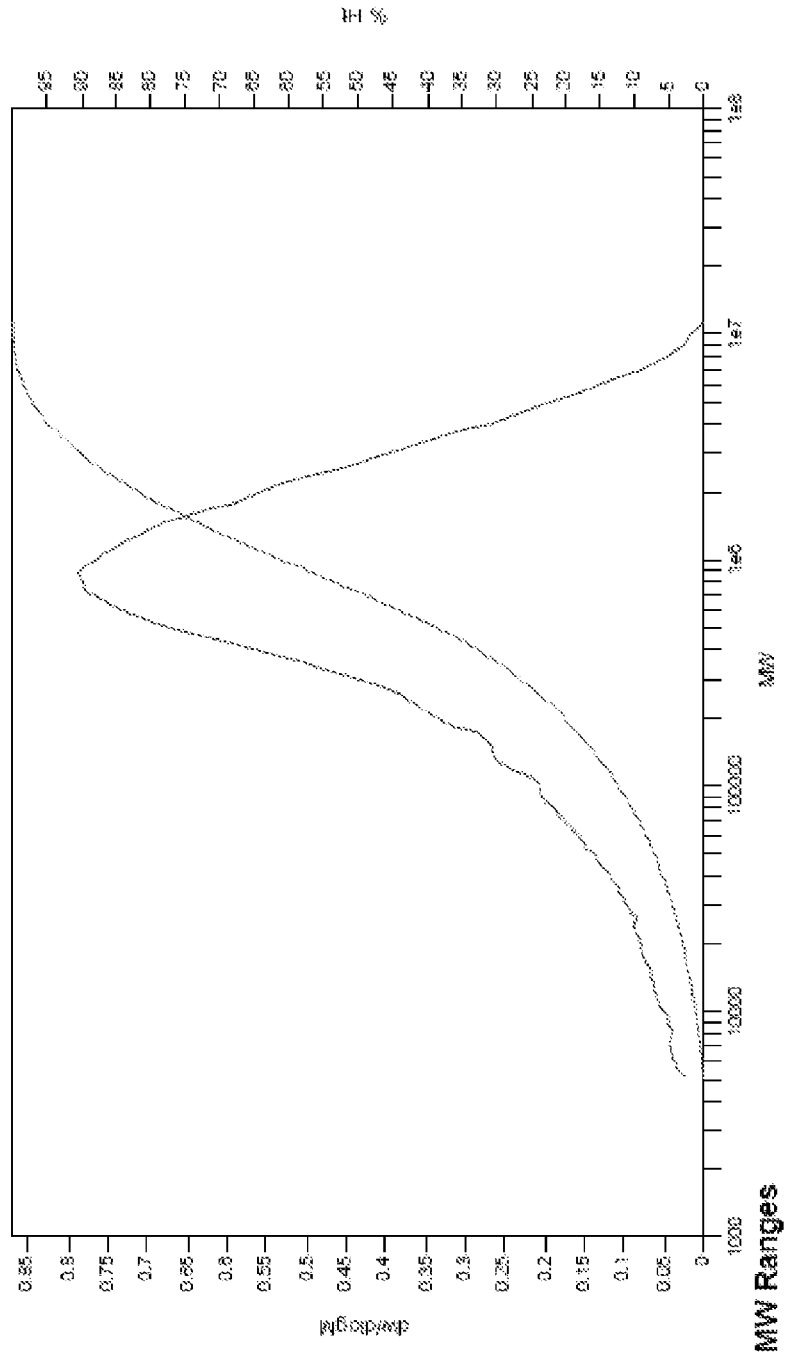
FIG. 13 presents a plot of the molecular weight distribution of the polymer of Example 26.
Figure 14:
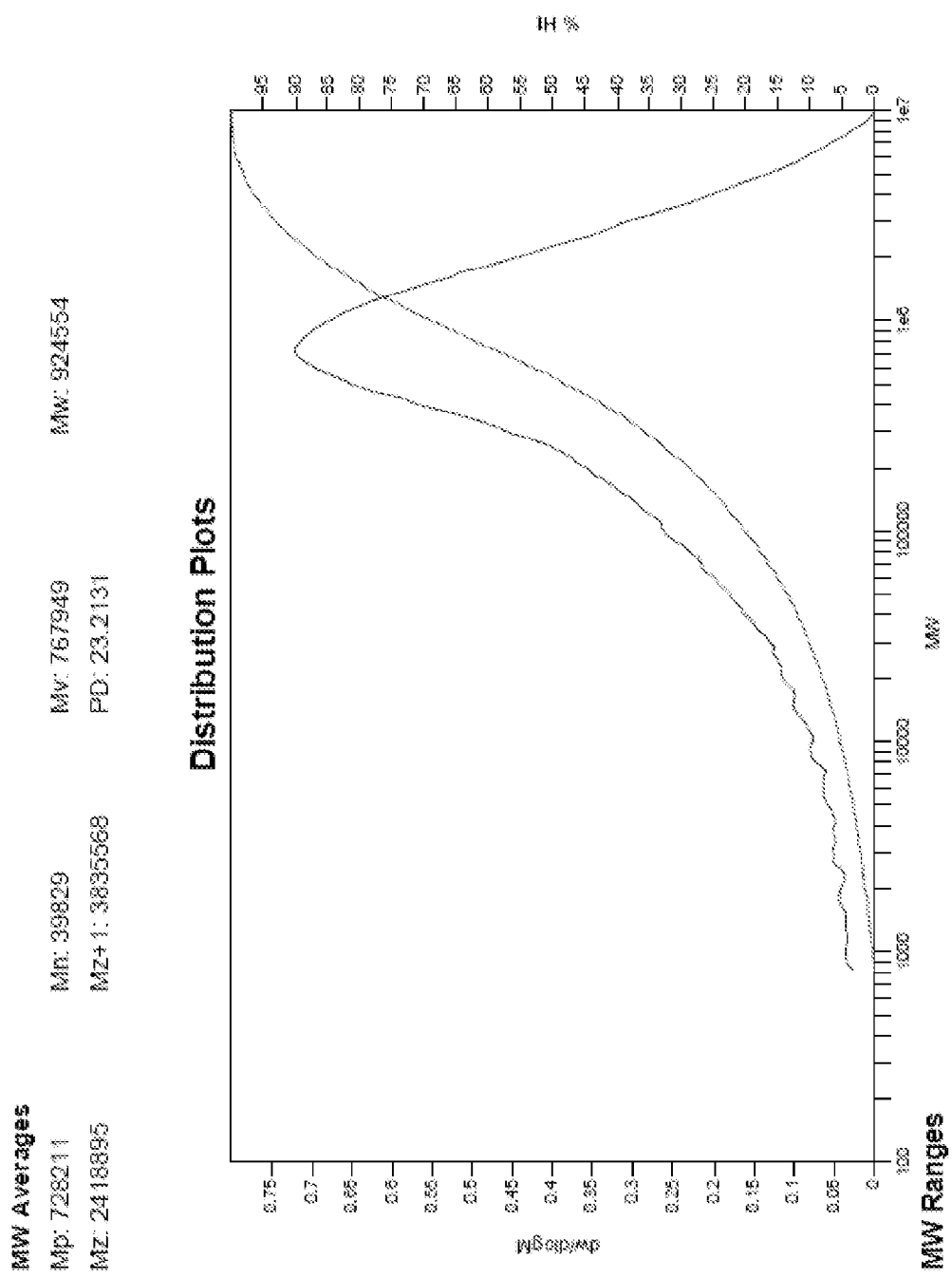
FIG. 14 presents a plot of the molecular weight distribution of the polymer of Example 27.
Figure 15:
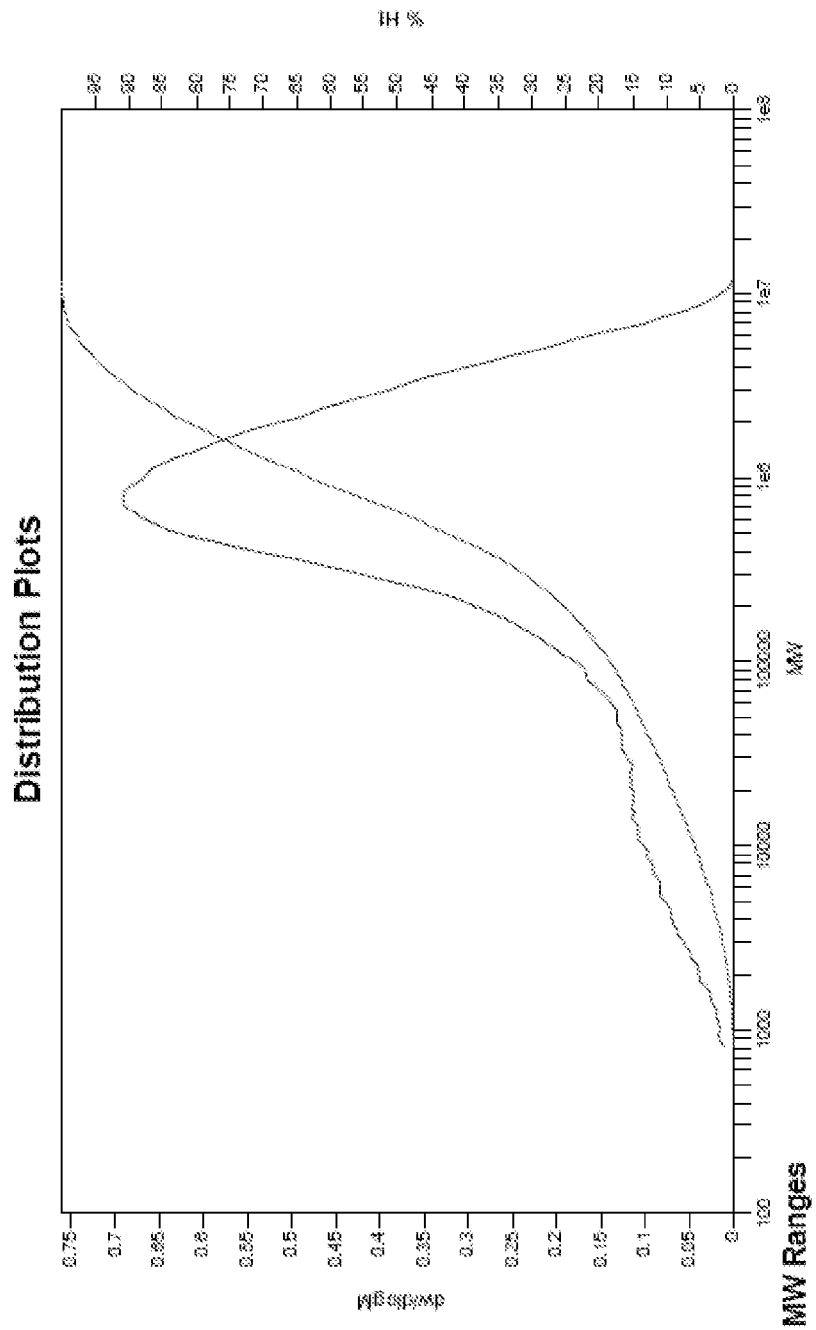
FIG. 15 presents a plot of the molecular weight distribution of the polymer of Example 28.
Figure 16:
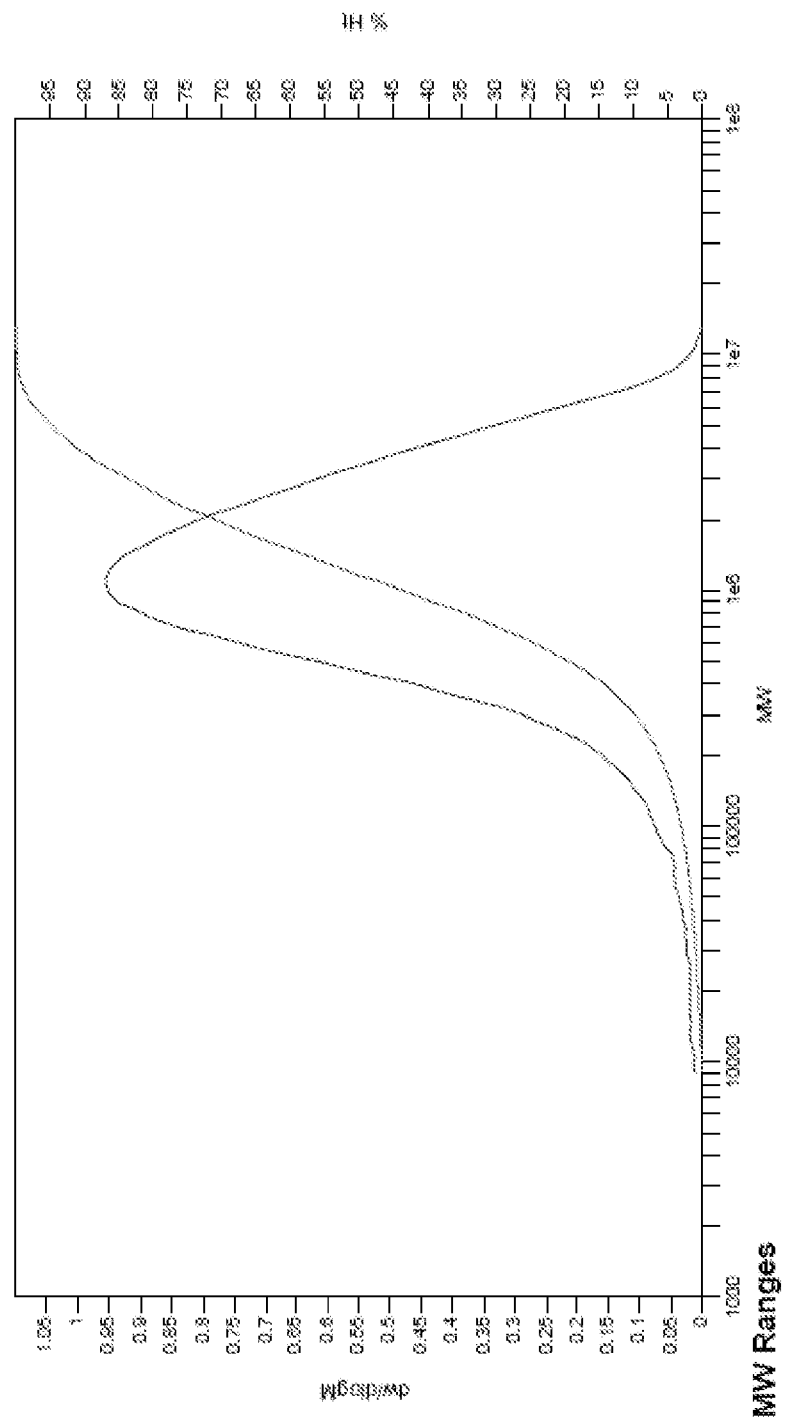
FIG. 16 presents a plot of the molecular weight distribution of the polymer of Example 30.

Compound 10 was synthesized as follows. A 1-mL toluene solution of compound 3a (0.060 g, 0.159 mmol) was added to a toluene (1 mL) solution of $V(=O)(O^iPr)_3$ (0.039 g, 0.159 mmol), forming a red solution. The solution was stirred at ambient temperature overnight, during which time the solution darkened to violet. The volatiles were removed, leaving a violet oil in quantitative yield. $^1$H NMR ($C_6D_6$): δ 7.33 (dd, J=1.2, 8.1 Hz, 2H), δ 7.24 (dd, J=0.9, 6.9 Hz, 2H), δ 6.77 (t, J=8.1 Hz, 2H), δ 5.00 (sept, J=6.0 Hz, 1H, VOCH(CH$_3$)$_2$), δ 1.05 (d, J=6.0 Hz, 6H, VOCH(CH$_3$)$_2$), δ 0.39 (s, 18H, SiMe$_3$). FIG. 6 illustrates the $^1$H-NMR analysis of compound 10.

Examples 9-12

Preparation of Chromium, Manganese, Iron, and Cobalt Combinations with 3a for Direct Use in Polymerization Reactions A 1-mL toluene solution of compound 3a (0.023 g, 0.062 mmol) was added to a toluene (1 mL) solution of M(acac)$_3$ (0.062 mmol), forming a solution. The resultant solution was stirred at ambient temperature overnight and used directly in subsequent polymerization experiments. The metal, M, was Cr for the solution of Example 9, Mn for the solution of Example 10, Fe for the solution of Example 11, and, and Co for the solution of Example 12.

Constructive Example 13

Constructive Synthesis of an Iron Complex with Thiolate Ligands, Compound 15

A general synthesis scheme for compound 15 is shown below:

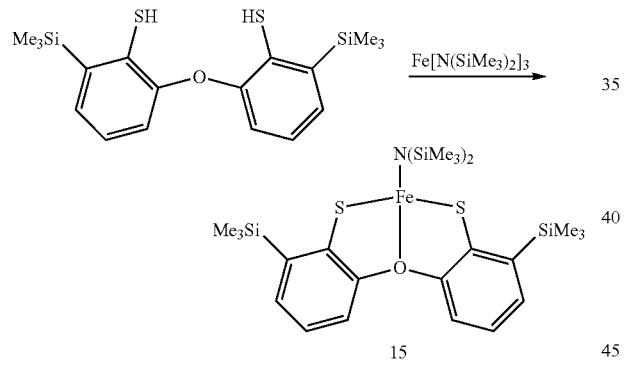

Compound 15 can be synthesized as follows. A 1-mL toluene solution of compound 3a (0.1 mmol) can be added to a toluene (1 mL) solution of Fe[N(SiMe$_3$)$_2$]$_3$ (0.1 mmol). The resultant mixture can be stirred at ambient temperature overnight. The volatiles can be removed, resulting in compound 15, which can be analyzed via $^1$H NMR.

Constructive Example 14

Constructive Synthesis of a Lanthanum Complex with Thiolate Ligands, Compound 16

A general synthesis scheme for compound 16 is shown below:

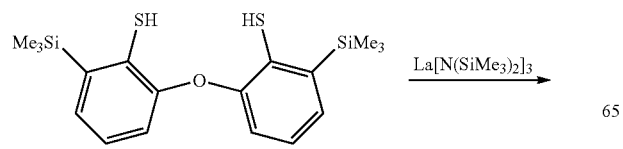

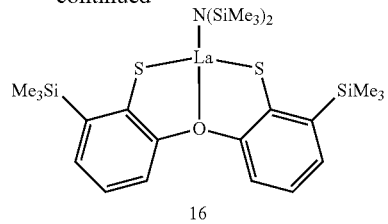

Compound 16 can be synthesized as follows. A 1-mL toluene solution of compound 3a (0.1 mmol) can be added to a toluene (1 mL) solution of La[N(SiMe$_3$)$_2$]$_3$ (0.1 mmol). The resultant mixture can be stirred at ambient temperature overnight. The volatiles can be removed, resulting in compound 16, which can be analyzed via $^1$H NMR.

Constructive Examples 15-16

Constructive Synthesis of a Tantalum Complexes with Thiolate Ligands, Compounds 17-18

A general synthesis scheme for compounds 17-18 is shown below:

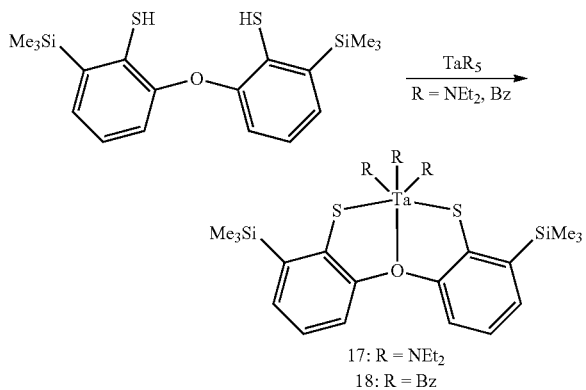

17: R = NEt$_2$
18: R = Bz

Compounds 17-18 can be synthesized as follows. A 1-mL toluene solution of compound 3a (0.1 mmol) can be added to a toluene (1 mL) solution of TaR$_5$ (0.1 mmol). The resultant mixture can be stirred at ambient temperature overnight. The volatiles can be removed, resulting in compounds 17-18, which can be analyzed via $^1$H NMR. In TaR$_5$, R can be NEt$_2$ for compound 17, and R can be Bz for compound 18.

Constructive Example 17

Constructive Synthesis of a Tantalum Complex with Thiolate Ligands, Compound 19

A general synthesis scheme for compound 19 is shown below:

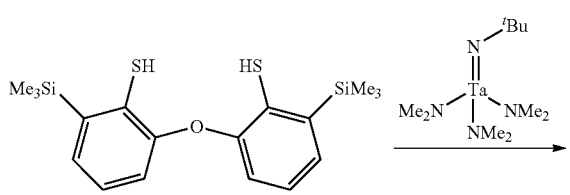

-continued

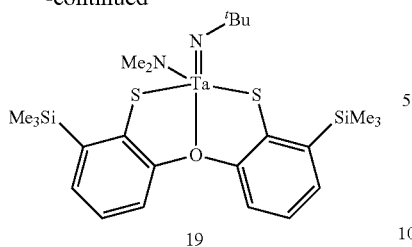

19

Compound 19 can be synthesized as follows. A 1-mL toluene solution of compound 3a (0.1 mmol) can be added to a toluene (1 mL) solution of Ta(NMe$_2$)$_3$(=N-$^t$Bu) (0.1 mmol). The resultant mixture can be stirred at ambient temperature overnight. The volatiles can be removed, resulting in compound 19, which can be analyzed via $^1$H NMR.

Constructive Example 18

Constructive Synthesis of a Tantalum Complex with Thiolate Ligands, Compound 20

A general synthesis scheme for compound 20 is shown below:

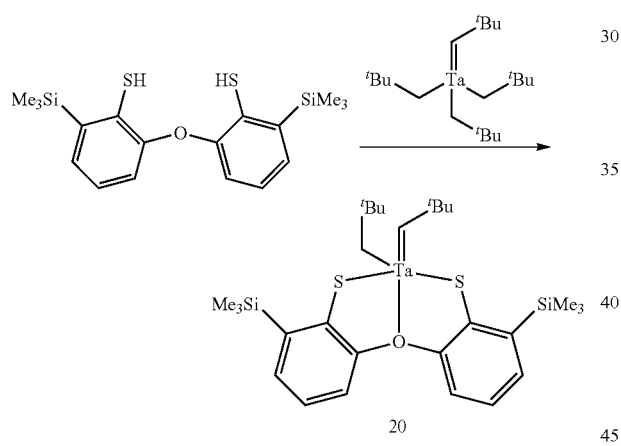

20

Compound 20 can be synthesized as follows. A 1-mL toluene solution of compound 3a (0.1 mmol) can be added to a toluene (1 mL) solution of Ta($^t$Bu)$_3$(=C—$^t$Bu) (0.1 mmol). The resultant mixture can be stirred at ambient temperature overnight. The volatiles can be removed, resulting in compound 20, which can be analyzed via $^1$H NMR.

Examples 19-30

Polymerization Experiments Using Titanium, Zirconium, Hafnium, and Vanadium Complexes Having Thiolate Ligands Table 1 summarizes certain polymerization reaction conditions and polymer properties for Examples 19-30. Catalyst activities listed are in grams of polymer per millimole of transition metal complex per hour per bar (1 bar=0.1 MPa). Example 23 showed a relatively high activity, about 10 times that of the activity of Examples 19-22. However, the activity for Example 23 was less than that of its corresponding free metal precursor, ZrBz$_4$, as shown in Example 25. The vanadium-based transition metal compound proved to be an effective ethylene polymerization catalyst when activated by an organoaluminum compound, namely diethylaluminum chloride, when MgCl$_2$ was employed; see Example 30. The polymer of Example 30 had a relatively narrow molecular weight distribution. The Mw/Mn, or polydispersity, was about 3.6 for the polymer of Example 30.

FIGS. 7-16 illustrate the molecular weight distributions of the polymers of Examples 19, 21-28, and 30 respectively. In these figures, the left side axis represents the molecular weight distribution, and the right side axis represents the cumulative molecular weight distribution. With the exception of Example 30, the polymers produced by the other transition metal complexes had broad molecular weight distributions, with Mw/Mn ratios ranging from 7 to 27. Additionally, the transition metal complexes produced polymers having very high molecular weights. Weight average molecular weights (Mw's) were generally in excess of 1,000,000 g/mol.

Examples 31-43

Polymerization Experiments Chromium, Manganese, Iron, and Cobalt Complexes Having Thiolate Ligands Table 2 summarizes certain polymerization reaction conditions and polymer properties for Examples 31-43, Catalyst activities listed are in grams of polymer per millimole of transition metal complex per hour per bar (1 bar=0.1 MPa). As an ethylene polymerization catalyst, only the chromium-based transition metal complex had appreciable catalyst activity.

Figure 17:
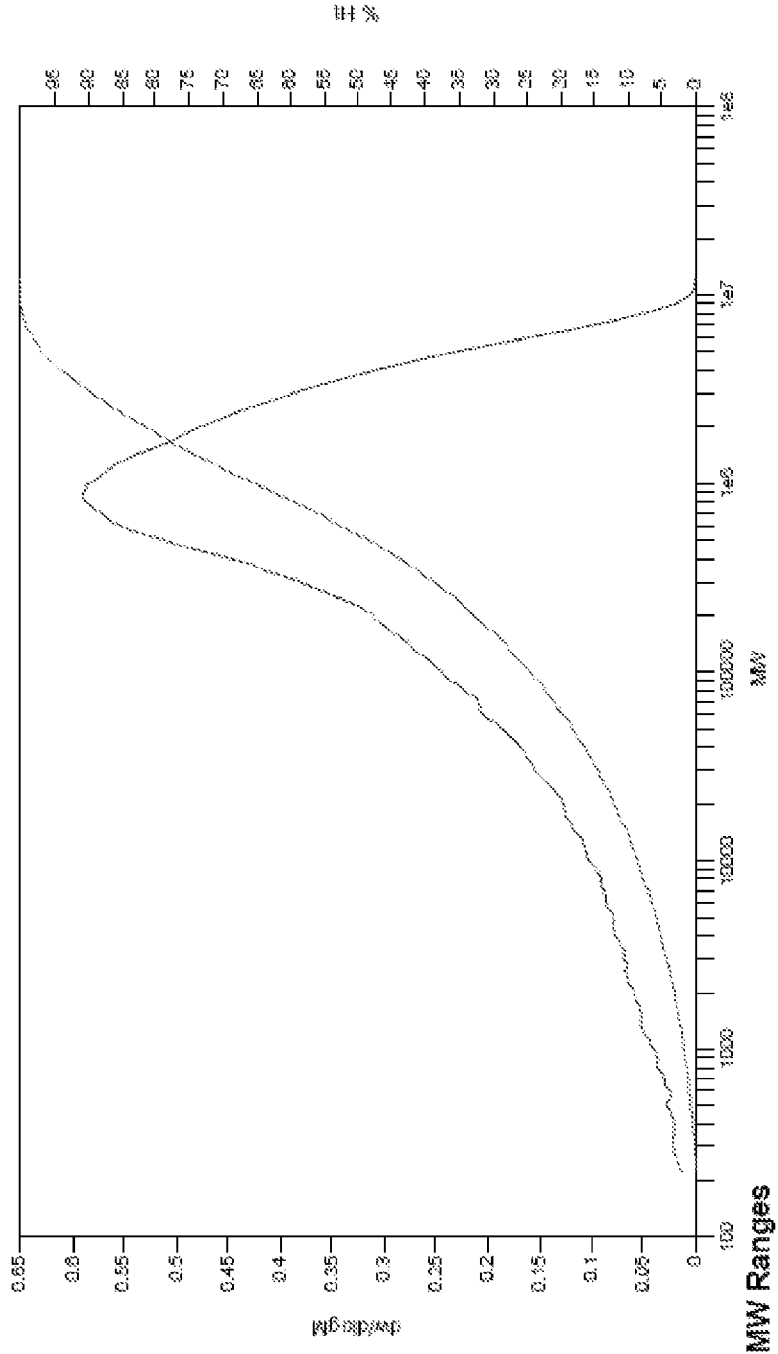
FIG. 17 presents a plot of the molecular weight distribution of the polymer of Example 33.

FIG. 17 illustrates the molecular weight distribution of the polymer of Example 33. The molecular weight of the polymer of Example 33 was in excess of 1,000,000 g/mol. Further, this polymer had a very broad molecular weight distribution, with a Mw/Mn ratio of around 69.

TABLE 1

Polymerization Conditions and Polymer Properties for Examples 19-30.

| Example | Transition Metal Compound (µmol) | Other Catalyst System Components | Catalyst Activity (g/mmol-hr-bar) | Mw/(10$^6$) (g/mol) | Mw/Mn |
|---|---|---|---|---|---|
| 19 | 6 (3.9) | 0.1 g SA<br>0.5 mL 1M TIBA | 29.8 | 1.24 | 7.8 |
| 20 | 6 (3.9) | 1.16 g 20% MAO/SiO$_2$ | 24.4 | insoluble | insoluble |
| 21 | 7a (4.1) | 0.1 g SA<br>0.5 mL 1M TIBA | 12.9 | 1.15 | 9.6 |
| 22 | 7a (4.1) | 2 mL<br>10% MAO in toluene | 23.3 | 0.64 | 11.9 |

TABLE 1-continued

Polymerization Conditions and Polymer Properties for Examples 19-30.

| Example | Transition Metal Compound (μmol) | Other Catalyst System Components | Catalyst Activity (g/mmol-hr-bar) | Mw/($10^6$) (g/mol) | Mw/Mn |
|---|---|---|---|---|---|
| 23 | 8 (4) | 0.1 g SA<br>0.5 mL 1M TIBA | 224.2 | 1.02 | 24.6 |
| 24 | 8 (4.6) | 0.1 g M-SSA<br>0.5 mL 1M TIBA | 79.1 | 0.95 | 22.1 |
| 25 | $ZrBz_4$ (4.4) | 0.1 g SA<br>0.5 mL 1M TIBA | 572.1 | 1.08 | 25.5 |
| 26 | 9 (4.1) | 0.1 g SA<br>0.5 mL 1M TIBA | 88.1 | 1.15 | 7.6 |
| 27 | $HfBz_4$ (3.7) | 0.1 g SA<br>0.5 mL 1M TIBA | 695.5 | 0.92 | 23.2 |
| 28 | 10 (4) | 0.1 g SA<br>0.5 mL 1M TTBA | 22.0 | 1.15 | 26.6 |
| 29 | 10 (4) | 1.16 g 20% $MAO/SiO_2$ | 31.7 | 1.09 | 15.1 |
| 30 | 10 (12) | 0.13 mg $MgCl_2$<br>2.0 mL 1M $Et_2AlCl$ | 30.8 | 1.63 | 3.6 |

Notes on Table 1.
Polymerization conditions for Examples 19-29: 550 psig (3.8 MPa), 80° C., 30 min.
Polymerization conditions for Example 30: 550 psig (3.8 MPa), 50° C., 60 min.

TABLE 2

Polymerization Conditions and Polymer Properties for Examples 31-43.

| Example | Catalyst Composition | Activator | Organoaluminum | Catalyst Activity (g/mmol-hr-bar) |
|---|---|---|---|---|
| 31 | 3.8 μmol of Example 9 | 1.16 g 20% $MAO/SiO_2$ | None | 112 |
| 32 | | 100 mg SA | 0.5 mL 1M TIBA | 79 |
| 33 | | 100 mg M-SSA | 0.5 mL 1M TIBA | 251 |
| 34 | | 100 mg FSA | 0.5 mL 1M TIBA | 37 |
| 35 | 3.8 μmol of Example 10 | 1.16 g 20% $MAO/SiO2$ | None | 0 |
| 36 | | 100 mg SA | 0.5 mL 1M TIBA | 0 |
| 37 | | 100 mg M-SSA | 0.5 mL 1M TIBA | 0 |
| 38 | 3.8 μmol of Example 11 | 1.16 g 20% $MAO/SiO_2$ | None | 0 |
| 39 | | 100 mg SA | 0.5 mL 1M TIBA | 0 |
| 40 | | 100 mg M-SSA | 0.5 mL 1M TIBA | 0 |
| 41 | 3.7 μmol of Example 12 | 1.16 g 20% $MAO/SiO_2$ | None | 0 |
| 42 | | 100 mg SA | 0.5 mL 1M TIBA | 0 |
| 43 | | 100 mg M-SSA | 0.5 mL 1M TIBA | 0 |

Notes on Table 2.
Polymerization conditions for Examples 31-43: 550 psig (3.8 MPa), 80° C., 30 min.

I claim:

1. A catalyst composition comprising an activator and a compound having the formula:

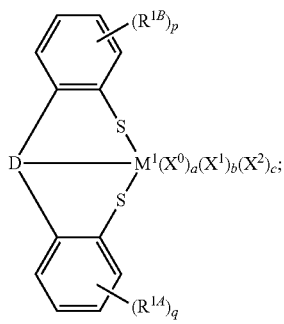

wherein:

$M^1$ is a transition metal;

each $R^{1A}$ and $R^{1B}$ independently is a $C_1$ to $C_{18}$ hydrocarbyl or hydrocarbylsilyl group, wherein p and q independently are 1, 2, 3, or 4;

D is O or $NR^{1C}$, wherein $R^{1C}$ is hydrogen or a $C_1$ to $C_{18}$ hydrocarbyl group;

each $X^0$ independently is a neutral ligand, wherein a is 0, 1, or 2;

each $X^1$ independently is a monoanionic ligand, wherein b is 0, 1, 2, 3, or 4;

$X^2$ is a dianionic ligand, wherein c is 0 or 1; and an oxidation state of $M^1$ is equal to (b+2c+2).

2. The composition of claim 1, wherein:

the activator comprises an aluminoxane compound, an organoboron or organoborate compound, an ionizing ionic compound, or any combination thereof;

$M^1$ is Ti, Zr, Hf, or V;

D is O;

p is 1 and q is 1;

$R^{1A}$ and $R^{1B}$ independently are methyl, ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, phenyl, tolyl, benzyl, naphthyl, trimethylsilyl, triisopropylsilyl, triphenylsilyl, or allyldimethylsilyl;

each $X^0$ independently is tetrahydrofuran, acetonitrile, pyridine, dimethyl amine, diethyl amine, trimethyl amine, trimethylphosphine, or triphenylphosphine;

each $X^1$ independently is hydrogen, a halide, methyl, phenyl, benzyl, an alkoxy, an aryloxy, acetylacetonate, an alkylamino, a dialkylamino, a trihydrocarbylsilyl, or a hydrocarbylaminosilyl; and $X^2$ is =O, =NR$^{2A}$, or =CR$^{2B}$R$^{2C}$, wherein R$^{2A}$, R$^{2B}$, and R$^{2C}$ independently are hydrogen or a $C_1$ to $C_8$ alkyl group.

3. A polymerization process, the process comprising:
contacting the catalyst composition of claim 2 with ethylene and a comonomer comprising 1-butene, 1-hexene, 1-octene, or a combination thereof, to produce an ethylene polymer.

4. The composition of claim 1, wherein:
the catalyst composition further comprises an organoaluminum compound;
the activator comprises fluorided alumina, sulfated alumina, fluorided silica-alumina, sulfated silica-alumina, fluorided silica-coated alumina, sulfated silica-coated alumina, phosphated silica-coated alumina, or any combination thereof;
$M^1$ is Ti, Zr, Hf, or V;
D is O;
p is 1 and q is 1;
$R^{1A}$ and $R^{1B}$ independently are methyl, ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, phenyl, tolyl, benzyl, naphthyl, trimethylsilyl, triisopropylsilyl, triphenylsilyl, or allyldimethylsilyl;
each $X^0$ independently is tetrahydrofuran, acetonitrile, pyridine, dimethyl amine, diethyl amine, trimethyl amine, trimethylphosphine, or triphenylphosphine;
each $X^1$ independently is hydrogen, a halide, methyl, phenyl, benzyl, an alkoxy, an aryloxy, acetylacetonate, an alkylamino, a dialkylamino, a trihydrocarbylsilyl, or a hydrocarbylaminosilyl; and
$X^2$ is =O, =NR$^{2A}$, or =CR$^{2B}$R$^{2C}$, wherein R$^{2A}$, R$^{2B}$, and R$^{2C}$ independently are hydrogen or a $C_1$ to $C_8$ alkyl group.

5. A polymerization process, the process comprising:
contacting the catalyst composition of claim 4 with ethylene and a comonomer comprising 1-butene, 1-hexene, 1-octene, or a combination thereof, to produce an ethylene polymer.

6. A catalyst composition comprising an activator and a compound having the formula:

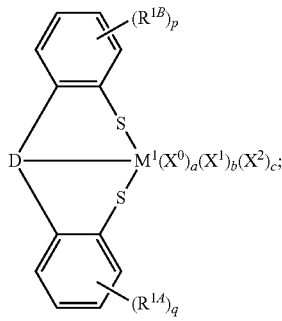

(I)

wherein:
$M^1$ is a transition metal;
each $R^{1A}$ and $R^{1B}$ independently is a $C_1$ to $C_{18}$ hydrocarbyl or hydrocarbylsilyl group, wherein p and q independently are 1, 2, 3, or 4;

D is O or NR$^{1C}$, wherein R$^{1C}$ is hydrogen or a $C_1$ to $C_{18}$ alkyl group;
each $X^0$ independently is a neutral ligand, wherein a is 0, 1, or 2;
each $X^1$ independently is a monoanionic ligand, wherein b is 0, 1, 2, 3, or 4;
$X^2$ is a dianionic ligand, wherein c is 0 or 1; and
an oxidation state of $M^1$ is equal to (b+2c+2).

7. The composition of claim 6, wherein the activator comprises an aluminoxane compound, an organoboron or organoborate compound, an ionizing ionic compound, or any combination thereof.

8. The composition of claim 7, wherein:
$M^1$ is Sc, Y, La, Ti, Zr, Hf, V, Cr, Fe, Ta, or Nb;
each $R^{1A}$ and $R^{1B}$ independently is methyl, ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, phenyl, tolyl, benzyl, naphthyl, trimethylsilyl, triisopropylsilyl, triphenylsilyl, or allyldimethylsilyl, wherein p and q independently are 1 or 2;
D is O;
each $X^0$ independently is an ether, a thioether, an amine, a nitrile, or a phosphine;
each $X^1$ independently is hydrogen, a halide, or a $C_1$ to $C_{18}$ hydrocarbyl group, hydrocarbyloxide group, hydrocarbylamino group, hydrocarbylsilyl group, or hydrocarbylaminosilyl group; and
$X^2$ is =O, =NR$^{2A}$, or =CR$^{2B}$R$^{2C}$, wherein R$^{2A}$, R$^{2B}$, and R$^{2C}$ independently are hydrogen or a $C_1$ to $C_{18}$ hydrocarbyl group.

9. An olefin polymerization process, the process comprising:
contacting the catalyst composition of claim 7 with an olefin monomer and optionally an olefin comonomer under polymerization conditions to produce an olefin polymer.

10. The process of claim 9, wherein:
the catalyst composition is contacted with ethylene and an olefin comonomer comprising 1-butene, 1-hexene, 1-octene, or a combination thereof;
$M^1$ is Sc, Y, La, Ti, Zr, Hf, V, Cr, Fe, Ta, or Nb;
each $R^{1A}$ and $R^{1B}$ independently is methyl, ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, phenyl, tolyl, benzyl, naphthyl, trimethylsilyl, triisopropylsilyl, triphenylsilyl, or allyldimethylsilyl, wherein p and q independently are 1 or 2;
D is O;
each $X^0$ independently is an ether, a thioether, an amine, a nitrile, or a phosphine;
each $X^1$ independently is hydrogen, a halide, or a $C_1$ to $C_{18}$ hydrocarbyl group, hydrocarbyloxide group, hydrocarbylamino group, hydrocarbylsilyl group, or hydrocarbylaminosilyl group; and
$X^2$ is =O, =NR$^{2A}$, or =CR$^{2B}$R$^{2C}$, wherein R$^{2A}$, R$^{2B}$, and R$^{2C}$ independently are hydrogen or a $C_1$ to $C_{18}$ hydrocarbyl group.

11. The process of claim 10, wherein:
$M^1$ is Ti, Zr, Hf, or V;
p is 1 and q is 1;
each $X^0$ independently is tetrahydrofuran, acetonitrile, pyridine, dimethyl amine, diethyl amine, trimethyl amine, trimethylphosphine, or triphenylphosphine;
each $X^1$ independently is hydrogen, a halide, methyl, phenyl, benzyl, an alkoxy, an aryloxy, acetylacetonate, an alkylamino, a dialkylamino, a trihydrocarbylsilyl, or a hydrocarbylaminosilyl; and $X^2$ is =O, =$NR^{2A}$, or =$CR^{2B}R^{2C}$, wherein $R^{2A}$, $R^{2B}$, and $R^{2C}$ independently are hydrogen or a $C_1$ to $C_8$ alkyl group.

12. The composition of claim 6, wherein the activator comprises an activator-support comprising a solid oxide treated with an electron-withdrawing anion.

13. The composition of claim 12, wherein:
the catalyst composition further comprises an organoaluminum compound;
the activator-support comprises fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, sulfated silica-coated alumina, phosphated silica-coated alumina, or any combination thereof;
$M^1$ is Sc, Y, La, Ti, Zr, Hf, V, Cr, Fe, Ta, or Nb;
each $R^{1A}$ and $R^{1B}$ independently is methyl, ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, phenyl, tolyl, benzyl, naphthyl, trimethylsilyl, triisopropylsilyl, triphenylsilyl, or allyldimethylsilyl, wherein p and q independently are 1 or 2;
D is O;
each $X^0$ independently is an ether, a thioether, an amine, a nitrile, or a phosphine;
each $X^1$ independently is hydrogen, a halide, or a $C_1$ to $C_{18}$ hydrocarbyl group, hydrocarbyloxide group, hydrocarbylamino group, hydrocarbylsilyl group, or hydrocarbylaminosilyl group; and
$X^2$ is =O, =$NR^{2A}$, or =$CR^{2B}R^{2C}$, wherein $R^{2A}$, $R^{2B}$, and $R^{2C}$ independently are hydrogen or a $C_1$ to $C_{18}$ hydrocarbyl group.

14. An olefin polymerization process, the process comprising:
contacting the catalyst composition of claim 12 with an olefin monomer and optionally an olefin comonomer under polymerization conditions to produce an olefin polymer.

15. The process of claim 14, wherein:
the catalyst composition is contacted with ethylene and an olefin comonomer comprising 1-butene, 1-hexene, 1-octene, or a combination thereof;
the catalyst composition further comprises an organoaluminum compound;
the activator-support comprises fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, sulfated silica-coated alumina, phosphated silica-coated alumina, or any combination thereof;
$M^1$ is Sc, Y, La, Ti, Zr, Hf, V, Cr, Fe, Ta, or Nb;
each $R^{1A}$ and $R^{1B}$ independently is methyl, ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, phenyl, tolyl, benzyl, naphthyl, trimethylsilyl, triisopropylsilyl, triphenylsilyl, or allyldimethylsilyl, wherein p and q independently are 1 or 2;
D is O;
each $X^0$ independently is an ether, a thioether, an amine, a nitrile, or a phosphine;

each $X^1$ independently is hydrogen, a halide, or a $C_1$ to $C_{18}$ hydrocarbyl group, hydrocarbyloxide group, hydrocarbylamino group, hydrocarbylsilyl group, or hydrocarbylaminosilyl group; and
$X^2$ is =O, =$NR^{2A}$, or =$CR^{2B}R^{2C}$, wherein $R^{2A}$, $R^{2B}$, and $R^{2C}$ independently are hydrogen or a $C_1$ to $C_{18}$ hydrocarbyl group.

16. The process of claim 15, wherein:
$M^1$ is Ti, Zr, Hf, or V;
p is 1 and q is 1;
each $X^0$ independently is tetrahydrofuran, acetonitrile, pyridine, dimethyl amine, diethyl amine, trimethyl amine, trimethylphosphine, or triphenylphosphine;
each $X^1$ independently is hydrogen, a halide, methyl, phenyl, benzyl, an alkoxy, an aryloxy, acetylacetonate, an alkylamino, a dialkylamino, a trihydrocarbylsilyl, or a hydrocarbylaminosilyl; and
$X^2$ is =O, =$NR^{2A}$, or =$CR^{2B}R^{2C}$, wherein $R^{2A}$, $R^{2B}$, and $R^{2C}$ independently are hydrogen or a $C_1$ to $C_8$ alkyl group.

17. A catalyst composition comprising an activator and a compound having the formula:

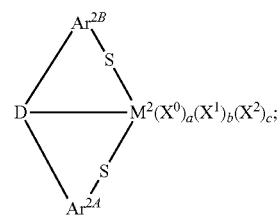

(II)

wherein:
$M^2$ is a Group 3 to Group 8 transition metal, including lanthanides and actinides;
$Ar^{2A}$ and $Ar^{2B}$ independently are an arylene group, wherein any additional substituents on the arylene group independently are a hydrogen atom or a $C_1$ to $C_{18}$ hydrocarbyl or hydrocarbylsilyl;
D is O; S; $NR^{1C}$, wherein $R^{1C}$ is hydrogen or a $C_1$ to $C_{18}$ alkyl group; $PR^{1D}$, wherein $R^{1D}$ is hydrogen or a $C_1$ to $C_{18}$ alkyl group; or one of the following heterocyclic groups:

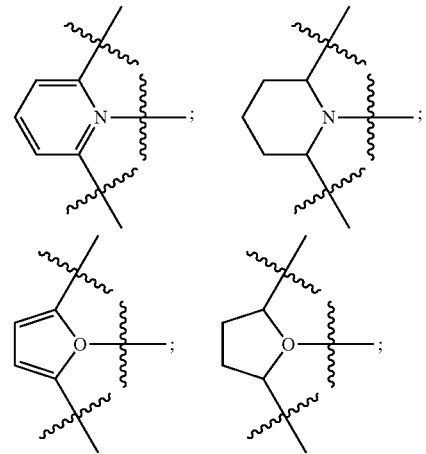

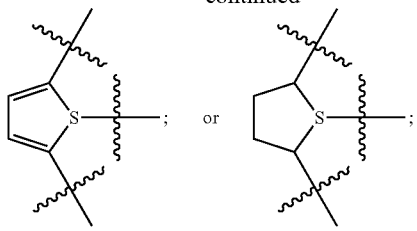

each $X^0$ independently is an ether, a thioether, an amine, a nitrile, or a phosphine, wherein a is 0, 1, or 2;

each $X^1$ independently is hydrogen, a halide, or a $C_1$ to $C_{18}$ hydrocarbyl group, hydrocarbyloxide group, hydrocarbylamino group, hydrocarbylsilyl group, or hydrocarbylaminosilyl group, wherein b is 0, 1, 2, 3, or 4;

$X^2$ is $=O$, $=NR^{2A}$, or $=CR^{2B}R^{2C}$, wherein $R^{2A}$, $R^{2B}$, and $R^{2C}$ independently are hydrogen or a $C_1$ to $C_{18}$ hydrocarbyl group, wherein c is 0 or 1; and an oxidation state of $M^2$ is equal to (b+2c+2).

18. The composition of claim 17, wherein:

the activator comprises an aluminoxane compound, an organoboron or organoborate compound, an ionizing ionic compound, or any combination thereof;

$M^2$ is Sc, Y, La, Ti, Zr, Hf, V, Cr, or Fe; and $Ar^{2A}$ and $Ar^{2B}$ are phenylene groups, wherein the additional substituents on the phenylene groups independently are hydrogen, methyl, ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, phenyl, tolyl, benzyl, naphthyl, trimethylsilyl, triisopropylsilyl, triphenylsilyl, or allyldimethylsilyl.

19. An olefin polymerization process, the process comprising:

contacting the catalyst composition of claim 18 with an olefin monomer and optionally an olefin comonomer under polymerization conditions to produce an olefin polymer.

20. The process of claim 19, wherein:

the catalyst composition is contacted with ethylene and an olefin comonomer comprising 1-butene, 1-hexene, 1-octene, or a combination thereof; and $M^2$ is Ti, Zr, Hf, V, or Cr.

21. The composition of claim 17, wherein:

the activator comprises an activator-support comprising a solid oxide treated with an electron-withdrawing anion;

$M^2$ is Sc, Y, La, Ti, Zr, Hf, V, Cr, or Fe; and $Ar^{2A}$ and $Ar^{2B}$ are phenylene groups, wherein the additional substituents on the phenylene groups independently are hydrogen, methyl, ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, phenyl, tolyl, benzyl, naphthyl, trimethylsilyl, triisopropylsilyl, triphenylsilyl, or allyldimethylsilyl.

22. An olefin polymerization process, the process comprising:

contacting the catalyst composition of claim 21 with an olefin monomer and optionally an olefin comonomer under polymerization conditions to produce an olefin polymer.

23. The process of claim 22, wherein:

$M^2$ is Ti, Zr, Hf, V, or Cr;

the catalyst composition is contacted with ethylene and an olefin comonomer comprising 1-butene, 1-hexene, 1-octene, or a combination thereof;

the catalyst composition further comprises an organoaluminum compound; and the activator-support comprises fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, sulfated silica-coated alumina, phosphated silica-coated alumina, or any combination thereof.

* * * * *